United States Patent
Tee, Jr. et al.

(10) Patent No.: US 8,859,843 B2
(45) Date of Patent: *Oct. 14, 2014

(54) ABSORBENT ARTICLE WITH CONTAINMENT BARRIER

(75) Inventors: Johannson Jimmy Tee, Jr., Mason, OH (US); Olaf Erik Alexander Isele, West Chester, OH (US); Calvin Hoi Wung Cheng, Cincinnati, OH (US); Rajeev Chhabra, Mason, OH (US); DeeAnn Ling Nelson, Mooresville, NC (US); Kemal Vatansever Catalan, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 146 days.

This patent is subject to a terminal disclaimer.

(21) Appl. No.: 13/326,606

(22) Filed: Dec. 15, 2011

(65) Prior Publication Data

US 2012/0150135 A1 Jun. 14, 2012

Related U.S. Application Data

(63) Continuation-in-part of application No. 13/024,826, filed on Feb. 10, 2011, and a continuation-in-part of (Continued)

(51) Int. Cl.
  *A61F 13/15* (2006.01)
  *A61F 13/475* (2006.01)
  *A61L 15/52* (2006.01)
  *A61F 13/494* (2006.01)

(52) U.S. Cl.
  CPC ............. *A61F 13/4753* (2013.01); *A61L 15/52* (2013.01); *A61F 13/4942* (2013.01)
  USPC .......................................... 604/381; 604/378

(58) Field of Classification Search
  USPC .......................... 604/367, 370–372, 378, 381
  See application file for complete search history.

(56) References Cited

U.S. PATENT DOCUMENTS 3,848,594 A 11/1974 Buell
3,860,003 A 1/1975 Buell (Continued)

FOREIGN PATENT DOCUMENTS

WO WO 2008/139427 A1 11/2008

OTHER PUBLICATIONS

"Melt-electrospining Part 1: Processing Parameters and Geometric Properties", Polymers 45 (2004), pp. 7597-7603 (Lyons et al).

(Continued)

*Primary Examiner* — Melanie Hand
*Assistant Examiner* — Aundria Hairell
(74) *Attorney, Agent, or Firm* — Kathleen Y. Carter

(57) ABSTRACT

An absorbent article comprising a chassis comprising a topsheet, a backsheet, an absorbent core disposed between the topsheet and the backsheet, and a pair of longitudinal barrier cuffs attached to the chassis. Each longitudinal cuff is formed of a web of material having first and second opposing surfaces and comprising a nonwoven component layer comprising fibers having a number-average diameter of less than about 1 micron, a mass-average diameter of less than about 1.5 microns, and a ratio of the mass-average diameter to the number-average diameter less than about 2. The absorbent article further comprises a hydrophobic coating disposed on at least one surface of the web of material.

20 Claims, 31 Drawing Sheets

Related U.S. Application Data application No. 13/024,844, filed on Feb. 10, 2011, and a continuation-in-part of application No. 13/024,858, filed on Feb. 10, 2011, and a continuation-in-part of application No. 12/691,929, filed on Jan. 22, 2010, and a continuation-in-part of application No. 12/691,934, filed on Jan. 22, 2010, now Pat. No. 8,313,792.

(60) Provisional application No. 61/303,177, filed on Feb. 10, 2010, provisional application No. 61/303,184, filed on Feb. 10, 2010, provisional application No. 61/303,187, filed on Feb. 10, 2010, provisional application No. 61/156,090, filed on Feb. 27, 2009, provisional application No. 61/156,150, filed on Feb. 27, 2009.

(56) References Cited

U.S. PATENT DOCUMENTS

| | | |
|---|---|---|
| 4,536,361 A | 8/1985 | Torobin |
| 4,610,678 A | 9/1986 | Weisman et al. |
| 4,662,875 A | 5/1987 | Hirotsu et al. |
| 4,673,402 A | 6/1987 | Weisman et al. |
| 4,695,278 A | 9/1987 | Lawson |
| 4,795,454 A | 1/1989 | Dragoo |
| 4,808,178 A | 2/1989 | Aziz et al. |
| 4,834,735 A | 5/1989 | Alemany et al. |
| 4,846,815 A | 7/1989 | Scripps |
| 4,888,231 A | 12/1989 | Angstadt |
| 4,894,060 A | 1/1990 | Nestegard |
| 4,909,803 A | 3/1990 | Aziz et al. |
| 4,940,464 A | 7/1990 | Van Gompel et al. |
| 4,946,527 A | 8/1990 | Battrell |
| 4,988,344 A | 1/1991 | Reising et al. |
| 4,988,345 A | 1/1991 | Reising |
| 5,092,861 A | 3/1992 | Nomura et al. |
| 5,147,345 A | 9/1992 | Young et al. |
| 5,151,092 A | 9/1992 | Buell et al. |
| 5,183,670 A | 2/1993 | Trudeau |
| 5,234,423 A | 8/1993 | Alemany et al. |
| 5,246,433 A | 9/1993 | Hasse et al. |
| 5,569,234 A | 10/1996 | Buell et al. |
| 6,120,487 A | 9/2000 | Ashton |
| 6,120,489 A | 9/2000 | Johnson et al. |
| 6,315,806 B1 | 11/2001 | Torobin et al. |
| 6,382,526 B1 | 5/2002 | Reneker et al. |
| 6,482,191 B1 | 11/2002 | Roe et al. |
| 6,520,425 B1 | 2/2003 | Reneker |
| 6,695,992 B2 | 2/2004 | Reneker |
| 6,713,011 B2 | 3/2004 | Chu et al. |
| 6,949,594 B2 | 9/2005 | Roth et al. |
| 7,585,437 B2 | 9/2009 | Jirsak et al. |
| 7,626,073 B2 | 12/2009 | Catalan |
| 7,628,941 B2 | 12/2009 | Krause et al. |
| 7,666,343 B2 | 2/2010 | Johnson et al. |
| 7,722,347 B2 | 5/2010 | Krause et al. |
| 2005/0177123 A1 | 8/2005 | Catalan |
| 2005/0234411 A1 | 10/2005 | Ashton et al. |
| 2006/0014460 A1 | 1/2006 | Alexander Isele et al. |
| 2006/0189956 A1 | 8/2006 | Catalan |
| 2008/0004591 A1 | 1/2008 | Desai et al. |
| 2008/0195070 A1 | 8/2008 | Ponomarenko et al. |
| 2008/0195071 A1 | 8/2008 | Ponomarenko et al. |
| 2008/0242807 A1* | 10/2008 | Aoki ............................. 525/478 |
| 2009/0148547 A1 | 6/2009 | Petras et al. |
| 2010/0221407 A1 | 9/2010 | Tee, Jr. et al. |
| 2010/0222757 A1 | 9/2010 | Tee, Jr. et al. |
| 2011/0196325 A1 | 8/2011 | Isele et al. |

OTHER PUBLICATIONS

"The Thermal Effects on Electrospinning of Polyactic Acid Melts", Polymers 47 (2006), pp. 7497-7505 (Zhou et al).

"Effects of the Spin Line Temperature Profile and Melt Index of Poly(propylene) on Melt-electrospinning", Polymer Engineering and Science 49 (2009), pp. 391-396 (Kong et al).

"Relation Between Tacticity and Fiber Diameter in Melt-electrospinning of Polypropylene", Fibers and Polymers 10 (2009), pp. 275-279 (Kadomae et al).

"Exploration of Melt-electrospinning Based on the Novel Device", Proceedings of the IEEE International Conference on Properties and Applications of Dielectric Materials (2009), Abstract (Yang et al).

"Modeling of Melt Electrospinning for Semi-Crystalline Polyers", Polymer 51 (2010), pp. 274-290 (Zhmayev et al).

"Electrospinning of Polymer Melts: Phenomenological Observations", Polymers 48 (2007), pp. 6823-6833 (Dalton et al).

International Search Report, PCT/US2011/024327, mailed Apr. 19, 2011, 10 pages.

* cited by examiner

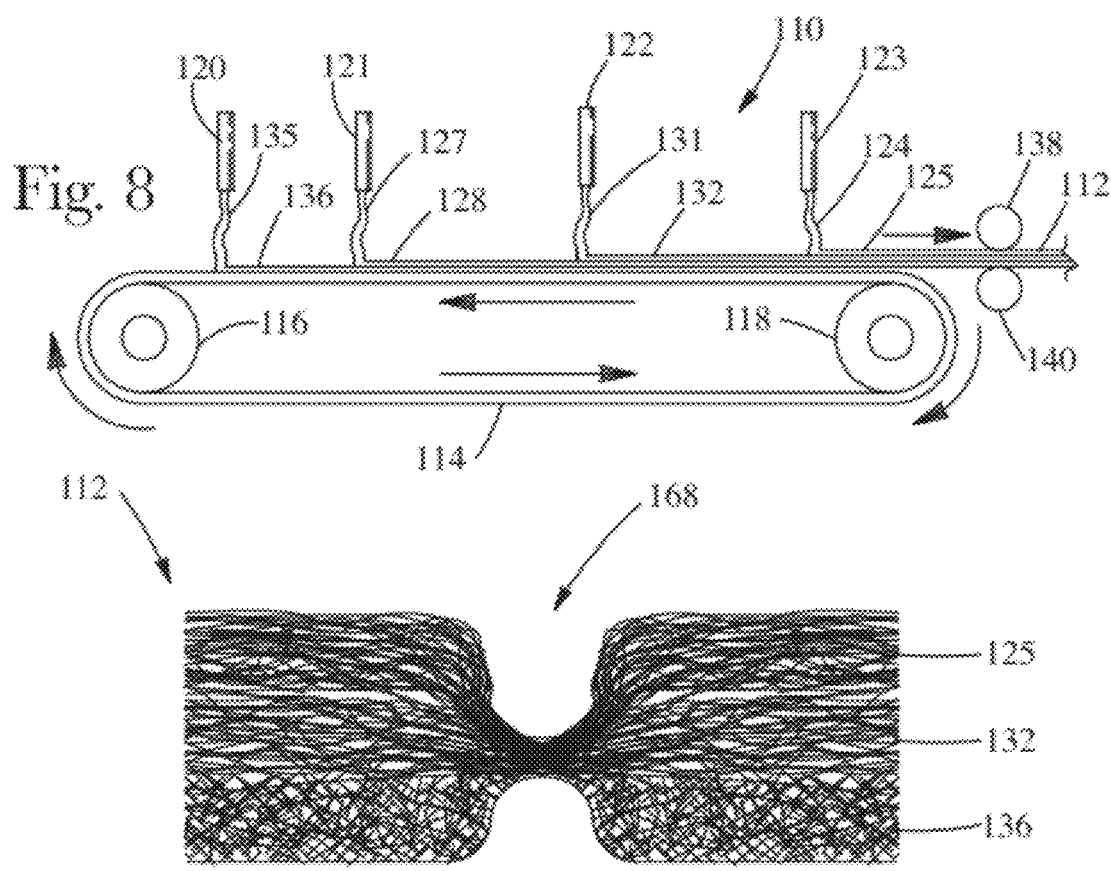
Fig. 8
Fig. 9
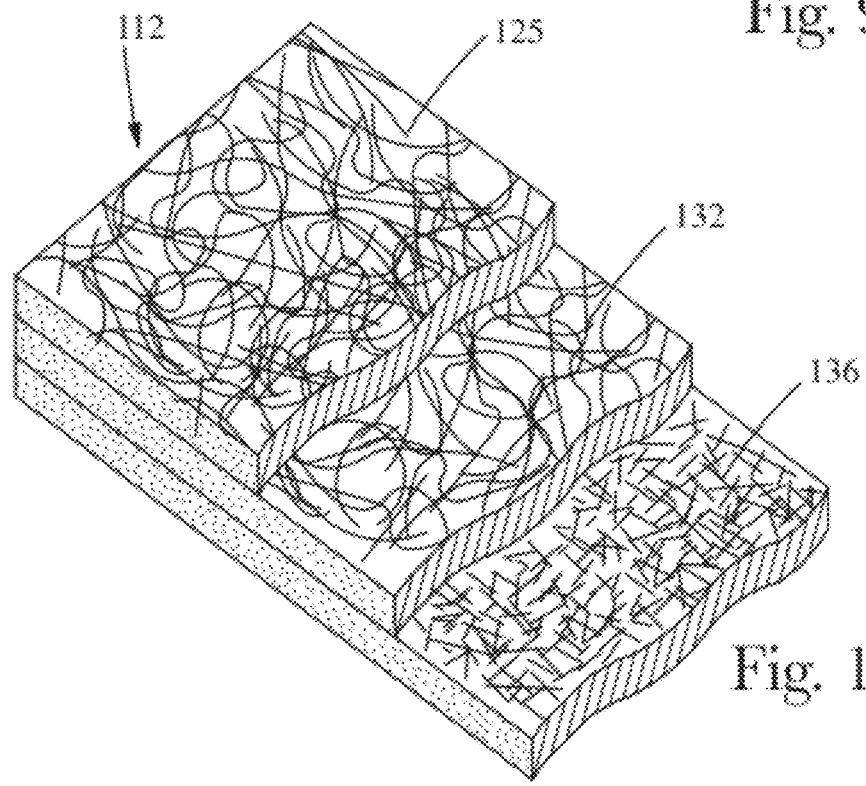
Fig. 10

ABSORBENT ARTICLE WITH CONTAINMENT BARRIER

CROSS REFERENCE TO RELATED APPLICATION

This application is a continuation-in-part of U.S. application Ser. Nos. 13/024,826, 13/024,844, and 13/024,858, all filed on Feb. 10, 2011; which claims the benefit of U.S. Provisional Application Nos. 61/303,177, 61/303,184 and 61/303,187, all filed on Feb. 10, 2010. This application is also a continuation-in-part of U.S. application Ser. Nos. 12/691,929 and 12/691,934, both filed on Jan. 22, 2010; which claims the benefit of U.S. Provisional Application Nos. 61/156,090 and 61/156,150, all filed on Feb. 27, 2009.

FIELD OF THE INVENTION

The present disclosure generally relates to consumer products such as absorbent articles and methods for manufacturing the same, and more particularly relates to absorbent articles having containment barriers with web material configurations and a hydrophobic surface coating, and methods of manufacturing the same.

BACKGROUND OF THE INVENTION

Nonwoven fabric webs may be useful in a wide variety of applications. Various nonwoven fabric webs may comprise spunbond, meltblown, spunbond ("SMS") webs comprising outer layers of spunbond thermoplastics (e.g., polyolefins) and an interior layer of meltblown thermoplastics. Such SMS nonwoven fabric webs may comprise spunbond layers which are durable and an internal meltblown layer which is porous but which may inhibit fast strikethrough of fluids, such as bodily fluids, for example, or the penetration of bacteria through the fabric webs. In order for such a nonwoven fabric web to perform to particular characteristics, it may be desirable for the meltblown layer to have a fiber size and a porosity that assures breathability of the nonwoven fabric web while at the same time inhibiting the strikethrough of fluids.

Absorbent articles such as diapers, training pants, incontinent wear and feminine hygiene products, for example, may also utilize nonwoven fabric webs for many purposes such as liners, transfer layers, absorbent media, barrier layers and cuffs, backings, and other components. For many such applications, the barrier properties of the nonwoven fabric web play an important role in the performance of the fabric webs, such as the performance as a barrier to fluid penetration, for example. Absorbent articles may comprise multiple elements such as a liquid permeable topsheet intended to be placed next to the wearer's skin, a liquid impermeable backsheet which forms, in use, the outer surface of the absorbent article, various barrier cuffs, and an absorbent core disposed between the topsheet and the backsheet.

When absorbent articles are produced, webs of materials, such as nonwoven materials, are bonded to each other. The bonding of these materials can be done for example via a mechanical bonding process. Reducing the manufacturing cost of absorbent articles by reducing the basis weight of the webs while preserving, if not improving, their functionality remains a challenge. For example, it is believed that when the combined basis weight of the webs to be bonded is less than 30 gsm, a reduction in basis weight of currently available spunbond, or SMS nonwoven webs can result in a significantly higher rate of bond defects. Those defects can lead to increased leakage of the absorbent article. There remains a need to provide an absorbent article comprising low basis weight webs that have a high quality of bonds with a low rate of defect when webs are bonded together.

There is also a need for low basis weight nonwoven webs that may be used in the manufacture of absorbent articles at high production rates and packaged under significant compaction for extended periods of time while achieving and maintaining soft, air permeable (i.e. breathable) and liquid barrier materials with good tactile properties and good barrier properties to low surface tension fluid. Structural, mechanical and fluid-handling properties of available nonwoven webs are believed not to be sufficient. Therefore, there is also a need for improved nonwoven web structures.

An additional way to improve the liquid imperviousness of a nonwoven to liquids such as urine, menses, and loose fecal matter is to treat the nonwoven with a composition that renders the nonwoven, or portions thereof, more hydrophobic, for example, by coating the nonwoven with a composition containing one or more silicone polymers. Examples of surface coatings for improving the barrier properties of a nonwoven are disclosed in U.S. Publication Nos. 2005/0177123 and 2006/0189956. Known silicone containing coatings are typically formed as hydrophilic solutions (e.g., an emulsion of a polar liquid component such as water, a non-polar liquid component such as silicone oil, and other optional ingredient(s) such as surfactant(s) and stabilizer(s)).

Accordingly, it would be also desirable to provide an absorbent article that includes a material with improved barrier properties such as a hydrophobic surface coating.

SUMMARY OF THE INVENTION

In one embodiment, the present invention relates generally to an absorbent article to be worn about the lower torso. The absorbent article comprises a chassis comprising a topsheet, a backsheet, an absorbent core disposed between the topsheet and the backsheet, and a pair of longitudinal barrier cuffs attached to the chassis. Each longitudinal cuff is formed of a web of material, the web of material having first and second opposing surfaces. The web of material comprises a nonwoven component layer comprising fibers having a number-average diameter of less than about 1 micron, a mass-average diameter of less than about 1.5 microns, and a ratio of the mass-average diameter to the number-average diameter less than about 2. The absorbent article further comprises a hydrophobic coating disposed on at least one surface of the web of material such that a coated web of material is formed, the hydrophobic surface coating comprising a solventless, multicomponent silicone composition including at least two silicone polymers and being substantially free of amino silicones.

In another embodiment, the present invention relates to an absorbent article comprising a liquid pervious first topsheet, a backsheet joined to at least a portion of the topsheet, an absorbent core disposed between the topsheet and the backsheet, at least one barrier member comprising a web of material, the web of material having first and second opposing surfaces and having a low surface tension fluid strikethrough time of at least about 19 seconds and an air permeability of at least about 20 m$^3$/m$^2$/min. The absorbent article further comprises a hydrophobic coating disposed on at least one surface of the web of material such that a coated web of material is formed, the hydrophobic surface coating comprising a solventless, multicomponent silicone composition including at least two silicone polymers and being substantially free of aminosilicones.

BRIEF DESCRIPTION OF THE DRAWINGS

The above-mentioned and other features and advantages of the present disclosure, and the manner of attaining them, will become more apparent and the disclosure itself will be better understood by reference to the following description of non-limiting embodiments of the disclosure taken in conjunction with the accompanying drawings, wherein:

FIG. 8 is a schematic diagram of a forming machine used to make a nonwoven web of material in accordance with one non-limiting embodiment of the present disclosure.

FIG. 9 is a cross-sectional view of a nonwoven web of material in a three layer configuration in accordance with one non-limiting embodiment of the present disclosure.

FIG. 10 is a perspective view of the web of material of FIG. 9 with various portions of nonwoven component layers cut away to show the composition of each nonwoven component layer in accordance with one non-limiting embodiment of the present disclosure.

FIG. 31 graphically illustrates the low surface tension fluid strikethrough times of various samples of Table 2B of Example 2B compared the number-average diameter of the samples.

FIGS. 33 and 34 graphically illustrate the low surface tension fluid strikethrough times of various SMS webs compared with the low surface tension fluid strikethrough times of the SMNS webs of the present disclosure.

DETAILED DESCRIPTION OF THE INVENTION

Figure 1:
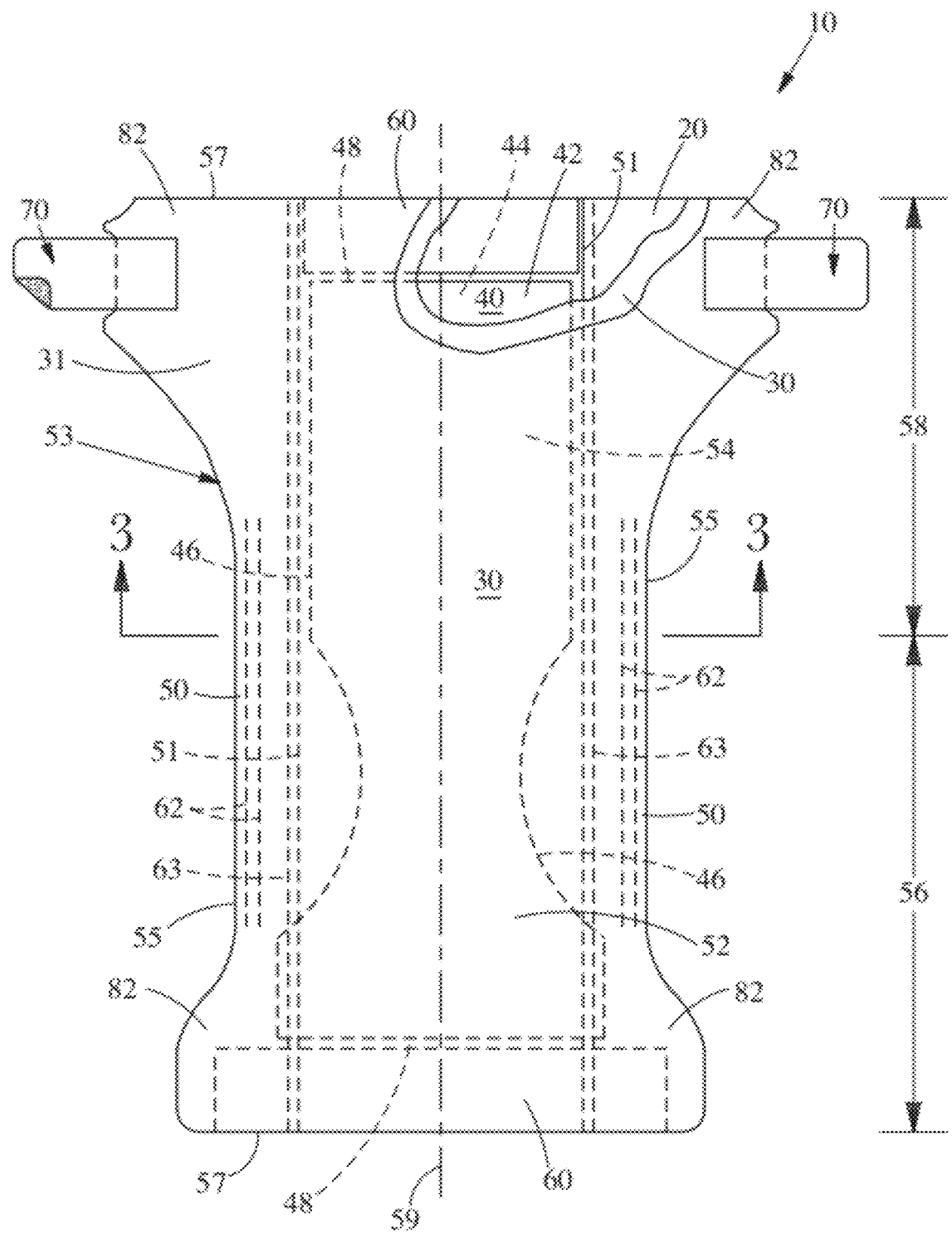
FIG. 1 is a plan view of an absorbent article in accordance with one non-limiting embodiment of the present disclosure.

Various non-limiting embodiments of the present disclosure will now be described to provide an overall understanding of the principles of the structure, function, manufacture, and use of the apparatuses and methods disclosed herein. One or more examples of these non-limiting embodiments are illustrated in the accompanying drawings. Those of ordinary skill in the art will understand that the apparatuses and methods specifically described herein and illustrated in the accompanying drawings are non-limiting example embodiments and that the scope of the various non-limiting embodiments of the present disclosure are defined solely by the claims. The features illustrated or described in connection with one non-limiting embodiment may be combined with the features of other non-limiting embodiments. Such modifications and variations are intended to be included within the scope of the present disclosure.

Definitions:

In this description, the following terms have the following meanings

The term "absorbent article" refers to a device that is placed against or in proximity to a body of a wearer to absorb and contain various exudates discharged from the body. Example absorbent articles comprise diapers, training pants, pull-on pant-type diapers (i.e., a diaper having a pre-formed waist opening and leg openings, such as illustrated in U.S. Pat. No. 6,120,487, issued to Ashton, on Sep. 19, 2000), refastenable diapers, incontinence briefs and undergarments, diaper holders and liners, feminine hygiene garments, panty liners, and absorbent inserts, for example.

The term "air permeability" is defined by the Air Permeability Test set forth below. Air permeability is set forth in $m^3/m^2/minute$ (m/min).

The term "basis weight" is defined by the Basis Weight Test set forth below. Basis weight is set forth in grams/$m^2$ (gsm).

"Body-facing surface" means a surface of the article or component which is intended to be worn toward or adjacent to the body of a wearer.

The term "bond area" refers to the area of an individual bond site. Bond area is set forth in $mm^2$.

The term "bond density" is the number of bonds in an area. Bond density is set forth in bonds per $cm^2$. A relative bond area is the bond density multiplied by the bond area (all converted to same unit area), and given in a percentage.

The term "cross direction" refers to a direction that is generally perpendicular to the machine direction.

The term "defect occurrence rate" is defined by the Defect Occurrence Rate Test set forth below.

The term "denier" refers to a unit of fineness of a fiber that is equal to the weight (in grams) per 9000 m of fiber.

The term "diameter" when referring to fibers is defined by the Fiber Diameter and Denier Test set forth below. Diameter of fibers is set forth in microns.

"Disposable" means articles that are generally not intended to be laundered or otherwise restored or reused. (i.e., they are intended to be discarded after a single use and, preferably, to be recycled, composted or otherwise discarded in an environmentally compatible manner).

"Disposed" means the placement of one element of an article relative to another element of an article. For example, the elements may be formed (joined and positioned) in a particular place or position as a unitary structure with other elements of the diaper or as a separate element joined to another element of the diaper.

The term "elongatable material," "extensible material," or "stretchable material" are used interchangeably and refer to a material that, upon application of a biasing force, can stretch to an elongated length of at least 150% of its relaxed, original length (i.e. can stretch to 50% more than its original length), without complete rupture or breakage as measured by EDANA method 20.2-89. In the event such an elongatable material recovers at least 40% of its elongation upon release of the applied force, the elongatable material will be considered to be "elastic" or "elastomeric." For example, an elastic material that has an initial length of 100 mm can extend to 150 mm, and upon removal of the force retracts to a length of at least 130 mm (i.e., exhibiting a 40% recovery). In the event the material recovers less than 40% of its elongation upon release of the applied force, the elongatable material will be considered to be "substantially non-elastic" or "substantially non-elastomeric". For example, a material that has an initial length of 100 mm can extend at least to 150 mm, and upon removal of the force retracts to a length of 145 mm (i.e., exhibiting a 10% recovery).

The term "elastic strand" or "elastic member" refers to a ribbon or strand (i.e. great length compared to either width and height or diameter of its cross-section) as may be part of the inner or outer cuff gathering component of an article.

The term "fiber" refers to any type of artificial fiber, filament, or fibril, whether continuous or discontinuous, produced through a spinning process, a meltblowing process, a melt fibrillation or film fibrillation process, or an electrospinning production process, or any other suitable process.

The term "film" refers to a polymeric material, having a skin-like structure, and it does not comprise individually distinguishable fibers. Thus, "film" does not include a nonwoven material. For purposes herein, a skin-like material may be perforated, apertured, or micro-porous and still be deemed a "film."

"Flexible" means materials which are compliant and that readily conform to the general shape and contours of a human body.

"Garment-facing surface" means a surface of the article or component which is on the opposite side of the body-facing surface and is intended to be worn toward or placed adjacent to the wearer's undergarments or clothing when the absorbent article is worn.

Figure 19:
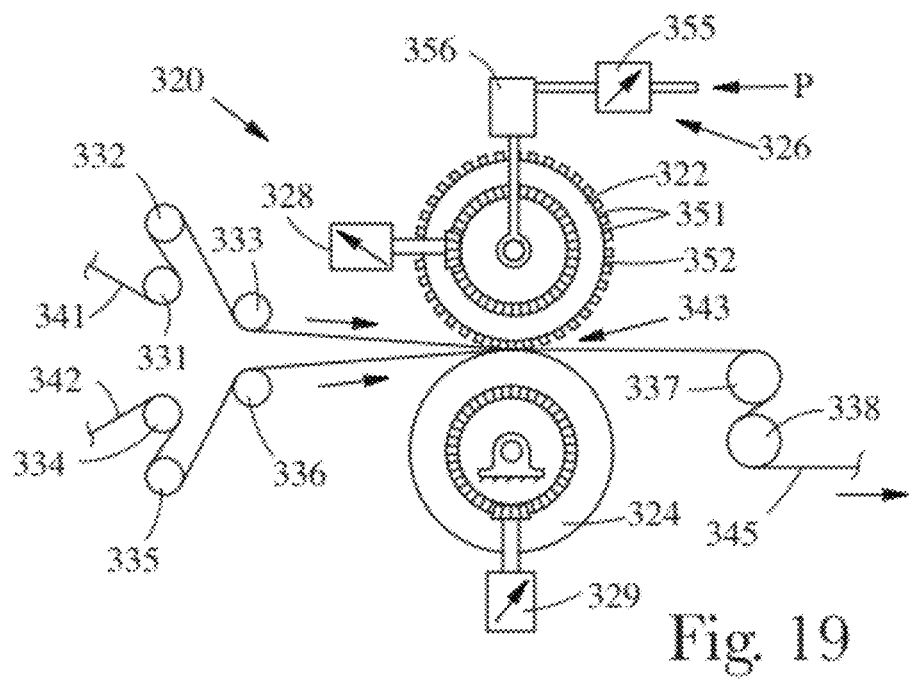
FIG. 19 illustrates a simplified dynamic mechanical bonding apparatus in accordance with one non-limiting embodiment of the present disclosure.

The term "grommet ring", or "grommet", refers to a ring (not necessarily circular or oval) that is formed around the periphery of a mechanical bond site. FIG. 19 shows a bond site 351b with a bottom surface 351bb and a grommet ring 376.

"Hydrophilic" means having a contact angle of less than 90° according to The American Chemical Society Publication "Contact Angle, Wettability, and Adhesion," edited by Robert F. Gould and copyrighted in 1964.

The term "hydrophobic" refers to a material or composition having a contact angle greater than or equal to 90° according to The American Chemical Society Publication "Contact Angle, Wettability, and Adhesion," edited by Robert F. Gould and copyrighted in 1964. In certain embodiments, hydrophobic surfaces may exhibit contact angles greater than 120°, greater than 140°, or even greater than 150°. Hydrophobic liquid compositions are generally immiscible with water. The term "hydrophobic melt additive" refers to a hydrophobic composition that has been included as an additive to a hot melt composition (.i.e., blended into a thermoplastic melt), which is then formed into fibers and/or a substrate (e.g., by spunbonding, meltblowing, or extruding).

The term "hydrophobic surface coating" refers to a composition that has been applied to a surface in order to render the surface hydrophobic or more hydrophobic. "Hydrophobic surface coating composition" means a composition that is to be applied to a surface in order to provide a hydrophobic surface coating.

"Joined" means configurations whereby an element is directly secured to another element by affixing the element directly to the other element and to configurations whereby an element is indirectly secured to another element by affixing the element to intermediate member(s), which in turn are affixed to the other element.

"Laminated structure" or "laminate" means a structure in which one layer, material, component, web, or substrate is joined, at least in part, to another layer, material, component, web, or substrate. As stated elsewhere in this application, a layer, material, component, web, or substrate may be folded over and bonded to itself to form a laminate.

The term "local basis weight variation" is defined by the Local Basis Weight Variation Test set forth below. Local basis weight variation is set forth in percentage.

"Low surface tension fluids" means fluids having a surface tension of less than 72 dynes/cm, 60 dynes/cm, or even less than 45 dynes/cm. For example, from 25 to 55 dynes/cm when measured according to the Interfacial Tension Measurement method below.

The term "low surface tension fluid strikethrough time" is defined by the Low Surface Tension Fluid Strikethrough Time Test set forth below. Low Surface Tension Fluid Strikethrough Time is set forth in seconds.

The term "machine direction" (MD) refers to the direction of material flow through a process.

The term "mass-average diameter" refers to a mass-weighted arithmetic mean diameter of fibers calculated from the fiber diameter, which is measured by the Fiber Diameter and Denier Test set forth below. Mass-average diameter of fibers is calculated by the Fiber Diameter Calculations set forth below. The mass-average diameter of fibers is set forth in microns.

The term "mean-flow pore diameter" in a nonwoven sample refers to a pore diameter corresponding to pressure at which the flow through pores in a "wet sample" is 50% of the flow through pores in a "dry sample". The mean flow pore diameter is measured by the Pore Size Distribution Test set forth below. The mean-flow pore diameter is such that the 50% of flow is through pores larger than the mean-flow pore diameter, and the rest of the flow is through the pores smaller than the mean-flow pore diameter. The mean-flow pore diameter is set forth in microns.

The term "calender bond" or "thermal bond" refers to a bond formed between fibers of a nonwoven by pressure and temperature such that the polymers within the bond melt together to form a continuous film-like material. The term "calendar bond" does not comprise a bond formed using an adhesive nor through the use of pressure only as defined by mechanical bond below. The term "thermal bonding" or "calender bonding" refers to the process used to create the thermal bond.

The term "mechanical bond" refers to a bond formed between two materials by pressure, ultrasonic attachment, and/or other mechanical bonding process without the intentional application of heat. The term mechanical bond does not comprise a bond formed using an adhesive.

The term "mechanical bonding" refers to the process used to create a mechanical bond. As used herein, the term "nonwoven" means a porous, fibrous material made from continuous (long) filaments (fibers) and/or discontinuous (short) filaments (fibers) by processes such as, for example, spunbonding, meltblowing, carding, and the like. "Nonwoven" does not include a film, woven cloth, or knitted cloth.

"Multicomponent," when referring to silicone compositions, means a silicone composition that includes two or more chemically distinct silicone polymers.

"Non-aqueous" means a composition contains little (i.e., less than one weight % by weight of the composition) or no (zero weight %) water.

"Nonwoven" means a manufactured sheet, web, or batt of directionally or randomly oriented fibers, bonded by friction, and/or cohesion, excluding paper and products which are woven, knitted, tufted, stitchbonded, incorporating binding yarns or filament, or felted by wet milling, whether or not additionally needled. The fibers may be of natural or man-made origin. The fibers may be staple or continuous filaments or be formed in situ. The porous, fibrous structure of a nonwoven may be configured to be liquid pervious or impervious, as desired.

The term "nonwoven component layer" refers to one sheet, ply or layer of a web of material.

The term "number-average diameter," alternatively "average diameter", refers to an arithmetic mean diameter of fibers calculated from the fiber diameter, which is measured by the Fiber Diameter and Denier Test set forth below. Number-average diameter of fibers is calculated by the Fiber Diameter Calculations set forth below. The number-average diameter of fibers is set forth in microns.

The term "polydispersity" refers to a measure of the width of a distribution calculated by a ratio of the mass-average diameter to the number-average diameter.

The term "porosity" refers to a measure of void volume of the nonwoven layer with the fibers composed of a material, and is calculated as (1−[basis weight]/[thickness×material density]) with the units adjusted so that they cancel out.

The term "relative standard deviation" (RSD) refers to a measure of precision calculated by dividing the statistic standard deviation for a series of measurements by the statistic average measurement of the series of measurements. This is often also called coefficient of variation or COV.

"Solventless" means the absence of a liquid medium such as water or an organic solvent for carrying the active component(s) of an HSC composition. At least some conventional, non-aqueous surface coatings include organic solvents (e.g., toluene, ethanol, hexane, acetone, methyl acetate, petrol ether, and turpentine), which need to be removed, for example, through evaporation. It is to be understood that even after the evaporation of the solvent such surface coating compositions are still not solventless surface coatings as contemplated herein. Similarly, conventional aqueous surface coatings include more than 1% water by weight of the composition, which is typically removed, for example, through drying.

"Telomer" means an addition polymer, typically of low molecular weight, in which the growth of molecules is terminated by a radical-supplying chain transfer agent or a low molecular weight polymer in which the terminal group on the end of the chain-like molecule is not the same as the side group. "Oligomer" means a polymer comprising relatively few (i.e., two to ten) repeating units.

"Web" means a material capable of being wound into a roll. Webs may be films, nonwovens, laminates, apertured laminates, etc. The face of a web refers to one of its large two dimensional surfaces, as opposed to its edge.

Nonwoven Webs

Nonwoven webs of material, such as nonwoven fabric webs, may comprise sheets of individual nonwoven component layers bonded together using mechanical, thermal, or chemical bonding processes. Nonwoven webs may be formed as flat, porous sheets made directly from individual fibers, from molten plastic, and/or plastic film. Some nonwoven structures may be strengthened or reinforced by a backing sheet, for example. Nonwoven structures may be engineered fabrics that may be a limited life, single-use fabric, or a very durable fabric. In various embodiments, nonwoven webs provide specific functions, such as absorbency, liquid repellency, resilience, stretch, softness, strength. These properties are often combined to create fabrics suited for specific applications, while achieving a good balance between product useful life and cost.

Continuous and discontinuous fiber spinning technologies of molten materials and typically of thermoplastics are commonly referred to as spunmelt technologies. Spunmelt technologies may comprise both the meltblowing process and spunbonding processes. A spunbonding process comprises supplying a molten polymer, which is then extruded under pressure through a large number of orifices in a plate known as a spinneret or die. The resulting continuous fibers are quenched and drawn by any of a number of methods, such as slot draw systems, attenuator guns, or Godet rolls, for example. In the spunlaying or spunbonding process, the continuous fibers are collected as a loose web upon a moving foraminous surface, such as a wire mesh conveyor belt, for example. When more than one spinneret is used in line for forming a multi-layered web, the subsequent nonwoven component layers are collected upon the uppermost surface of the previously formed nonwoven component layer.

The meltblowing process is related to the spunbonding process for forming a layer of a nonwoven material, wherein, a molten polymer is extruded under pressure through orifices in a spinneret or a die. High velocity gas impinges upon and attenuates the fibers as they exit the die. The energy of this step is such that the formed fibers are greatly reduced in diameter and are fractured so that micro-fibers of indeterminate length are produced. This differs from the spunbonding process where the continuity of the fibers are generally preserved. Often meltblown nonwoven structures are added to spunbond nonwoven structures to form spunbond, meltblown ("SM") webs or spunbond, meltblown, spunbond ("SMS") webs, which are strong webs with some barrier properties.

Other methods to produce fine fibers comprise melt fibrillation and electrospinning Melt fibrillation is a general class of making fibers defined in that one or more polymers are molten and are extruded into many possible configurations (e.g., co-extrusion, homogeneous or bicomponent films or filaments) and then fibrillated or fiberized into filaments. Meltblowing is one such specific method (as described herein). Melt film fibrillation is another method that may be used to produce submicron fibers. A melt film is produced from the melt and then a fluid is used to form fibers from the melt film. Examples of this method comprise U.S. Pat. Nos. 6,315,806, 5,183,670, and 4,536,361, to Torobin et al., and U.S. Pat. Nos. 6,382,526, 6,520,425, and 6,695,992, to Reneker et al. and assigned to the University of Akron. The process according to Torobin uses one or an array of co-annular nozzles to form a tube of film which is fibrillated by high velocity air flowing inside this annular film. Other melt film fibrillation methods and systems are described in the U.S. Pat. Publ. No. 2008/0093778, to Johnson, et al., published on Apr. 24, 2008, U.S. Pat. No. 7,628,941, to Krause et al., and U.S. Pat. Publ. No. 2009/0295020, to Krause, et al., published on Dec. 3, 2009 and provide uniform and narrow fiber distribution, reduced or minimal fiber defects such as unfiberized polymer melt (generally called "shots"), fly, and dust, for example. These methods and systems further provide uniform nonwoven webs for absorbent hygiene articles.

Electrospinning is a commonly used method of producing sub-micron fibers. In this method, typically, a polymer is dissolved in a solvent and placed in a chamber sealed at one end with a small opening in a necked down portion at the other end. A high voltage potential is then applied between the polymer solution and a collector near the open end of the chamber. The production rates of this process are very slow and fibers are typically produced in small quantities. Another spinning technique for producing sub-micron fibers is solution or flash spinning which utilizes a solvent.

There is a distinct difference between submicron diameter fibers made with electro-spinning versus those made with melt-fibrillation, namely the chemical composition. Electrospun submicron fibers are made of generally soluble polymers of lower molecular weight than the fibers made by melt-fibrillation. Commercially-viable electro-spinning methods have been described in U.S. Pat. No. 7,585,437, to Jirsak et al., U.S. Pat. No. 6,713,011 to Chu et al., and U.S. Pat. Publ. No. 2009/0148547, to Petras et al. Electro-spinning is recently explored in combination with a molten polymer rather than a polymer solution, as described in a reference by Lyons et al., "Melt-electrospinning Part I: Processing Parameters and Geometric Properties", published in the journal POLYMER 45 (2004) pp. 7597-7603; and by Zhou et al., "The Thermal Effects on Electrospinning of Polylactic Acid Melts", published in the journal POLYMER 47 (2006) pp. 7497-7505. The researchers in these studies have observed that electrospun fibers have average diameters generally greater than 1 micron as compared to solution electrospun fibers that are submicron (i.e., less than 1 micron). With motivation to reduce the fiber diameter, researchers have more recently started optimizing process and polymer parameters. Generally, the goal of the researchers has been to reduce the number-average diameter, but not reduce the mass-average diameter, and narrow the fiber diameter distribution. Improvements in melt electrospinning show that fiber diameter may be decreased, though to a limited extent but still above 1 micron (generally, in the range of 2 micron to 40 micron for polypropylene with molecular weights in the range of 12,000 to 200,000 Daltons) by the research works of Kong et al., "Effects of the Spin Line temperature Profile and Melt Index of Poly(propylene) on Melt-electrospinning", published in the journal POLYMER ENGINEERING AND SCIENCE 49 (2009) pp. 391-396 (average fiber diameter of 20 micron using polypropylene of melt flow index of 1500); by Kadomae et al., "Relation Between Tacticity and Fiber Diameter in Melt-electrospinning of Polypropylene", published in the journal FIBERS AND POLYMERS 10 (2009) pp. 275-279 (fiber diameters in the range of 5-20 microns using polypropylene with 12,000 and 205,000 molecular weight), and by Yang et al., "Exploration of Melt-electrospinning Based on the Novel Device", published in the Proceedings of the IEEE International Conference on Properties and Applications of Dielectric Materials, 2009, pp. 1223-1226 (finest fiber diameter of 5 micron). Most recently, the melt electrospinning has been modeled by Zhmayev et al., "Modeling of Melt Electrospinning for Semi-crystalline Polymers", published in the journal POLYMER 51 (2010) pp. 274-290. Even their models show that the fiber diameter of melt electrospun Nylon 6 (with a melt flow index of 3) is 2 microns, similar to that obtained by experiments. A prior work by Dalton et al., "Electrospinning of Polymer Melts: Phenomenological Observations", showed that fiber diameter of melt electrospun high molecular weight polypropylene fibers (with MFI in the range of 15 $cm^3/10$ min to 44 $cm^3/10$ min) may be significantly reduced to submicron by adding 1.5% of viscosity reducing additive, such as Irgatec CR 76 (from Ciba Specialty Chemicals, Switzerland). However, viscosity reducing additives, such as Irgatec CR 76, for example, significantly reduce the molecular weight of the polymer, as described in U.S. Pat. No. 6,949,594 to Roth et al., and by Gande et al., "Peroxide-free Vis-breaking Additive for Improved Qualities in Meltblown Fabrics", in the conference proceedings of the International Nonwovens Technical Conference, 2005, St. Louis, Mo., USA. Therefore, melt electrospun fibers have fiber diameters generally above 1 micron, or a high standard deviation leading to a broad fiber diameter distribution using commercial-grade high molecular weight polymers. Also, the polymer used in successful electrospinning of polymer melts uses a polymer of low molecular weight, e.g., in the case of PLA starting from 186,000 Dalton and degrading to actually 40,000 Dalton in the spun fibers used by Zhou et al., and use of viscosity reducing additive Irgatec CR 76 by Dalton et al. to reduce the melt viscosity by reducing the molecular weight. This compares to PLA used in melt-fibrillation processes of where e.g. the Natureworks 6202D resin starts at a molecular weight Mw of 140,000 Dalton and 'degrades' only to a molecular weight of 130,000 to 135,000 Dalton compared to the 40,000 of the melt-electrospun fibers. Also other grades of PLA (e.g. with Mw of 95,000 or 128,000) drop in molecular weight from neat resin to fiber form by less 10,000 or even less than 1,000 Dalton (less than 10% or less than 1%). Therefore, not only is the electrospinning process including the melt-electrospinning process at present still low in throughput, but it is structurally and chemically distinct from the fine fibers (i.e., the second nonwoven component layer) of the present disclosure. However, it is desirable to develop the electrospinning method towards making fine fibers at higher throughput and a narrow submicron diameter distribution as described herein.

In various embodiments, the fibers of the nonwoven structure may be made of polyesters, including PET and PBT, polylactic acid (PLA), and alkyds, polyolefins, including polypropylene (PP), polyethylene (PE), and polybutylene (PB), olefinic copolymers from ethylene and propylene, elastomeric polymers including thermoplastic polyurethanes (TPU) and styrenic block-copolymers (linear and radial di- and tri-block copolymers such as various types of Kraton), polystyrenes, polyamides, PHA (polyhydroxyalkanoates) and e.g. PHB (polyhydroxubutyrate), and starch-based compositions including thermoplastic starch, for example. The above polymers may be used as homopolymers, copolymers, e.g., copolymers of ethylene and propyelene, blends, and alloys thereof.

A variety of mass-produced consumer products such as diapers, paper towels, feminine care products, incontinence products and similar materials, employ nonwoven webs, such as SMS webs, in their manufacture. One of the largest users of SM and SMS webs is the disposable diaper and feminine care products industry. When the nonwoven webs are incorporated in an absorbent article, however, achieving a barrier against fluids that have a surface tension on a similar level of the surface energy of the SMS structure is sometimes difficult. For example, some SMS webs may have a surface energy level of approximately 30 mN/m, e.g., when made of PP, while the fluids sought to be blocked (i.e., infant urine or runny feces) may have surface tensions of 40-50 mN/m, or in some cases as low as 32 to 35 mN/m.

Further to the above, a number of undesirable holes extending through the nonwoven webs, such as SMS webs, for example, may be created during the mechanical bonding process of various structures. Current equipment and processes are not sufficient to bond combinations of SMS and spunbond (S, SS, SSS) materials at total basis weights below 25 gsm using a pressure/shear bonding without an increase in the number of holes created by the process. Holes are created from the bonding nub punching through thin areas of the SMS or SS web. Increased holes through the bonded materials result in higher product failure rates (i.e., leakage). When an absorbent article that incorporates such a nonwoven web is subsequently worn by a user, the presence of the holes may result in undesirable leaks.

In view of the above, low cost nonwoven webs having low basis weights, adequate air permeability, (i.e., breathable), adequate tactile characteristics, and low surface tension fluid strikethrough times exceeding certain parameters are desired. It is also desirable for the nonwoven materials to have more structural uniformity (i.e., less local basis weight variation), especially at lower basis weights (e.g., less than 25 gsm, alternatively, less than 15 gsm, alternatively, less than 13 gsm, and, alternatively, less than 10 gsm). An increased structural uniformity in nonwoven webs of 25 gsm or less reduces the amount of defects (e.g., holes) created during mechanical bonding processes. With specific regard to barrier cuff materials, in one embodiment, it is desired to have soft low basis weight webs with an improved barrier against low surface tension body exudates to give the absorbent core more time to absorb the fluid, especially with recent and future trend of more "body-fitting" diaper designs and thinner absorbent cores.

As described in more detail below, a nonwoven component layer having fine fibers ("N-fibers") with an average diameter of less than 1 micron (an "N-fiber layer") may be added to, or otherwise incorporated with, other nonwoven component layers to form a nonwoven web of material. In some embodiments, the N-fiber layer may be used to produce a SNS nonwoven web or SMNS nonwoven web, for example. The N-fibers may be comprised of a polymer, e.g., selected from polyesters, including PET and PBT, polylactic acid (PLA), alkyds, polyolefins, including polypropylene (PP), polyethylene (PE), and polybutylene (PB), olefinic copolymers from ethylene and propylene, elastomeric polymers including thermoplastic polyurethanes (TPU) and styrenic block-copolymers (linear and radial di- and tri-block copolymers such as various types of Kraton), polystyrenes, polyamides, PHA (polyhydroxyalkanoates) and e.g. PHB (polyhydroxubutyrate), and starch-based compositions including thermoplastic starch, for example. The above polymers may be used as homopolymers, copolymers, e.g., copolymers of ethylene and propylene, blends, and alloys thereof. The N-fiber layer may be bonded to the other nonwoven component layers by any suitable bonding technique, such as the calender bond process, for example, also called thermal point bonding.

The use of the N-fiber layer may also provide a soft and breathable (i.e., air permeable) nonwoven material that, at least in some embodiments, may be used in single web layer configurations in applications which previously used double web layer configurations. Furthermore, in some embodiments, the use of the N-fiber layer may at least reduce the undesirable migration of hydrophilic surfactants toward the web and, therefore, may ultimately result in better leak protection for an associated absorbent article. Also, when compared to an SMS web having a similar basis weight, the use of a nonwoven web comprising the N-fiber layer may decrease the number of defects (i.e., holes or pinholes through the mechanical bond site) created during the mechanical bonding process.

In addition to the use of an N-fiber layer in a nonwoven web, for various components of absorbent articles, such as barrier leg cuffs, for example, in order to achieve a desired fluid barrier, hydrophobic surface coatings, described in more detail below, may be applied to the webs. While intuitive that the N-fiber layer in a nonwoven web used in combination with a hydrophobic surface coating could increase the nonwoven's ability to be an effective fluid barrier, the present inventors have unexpectedly discovered a surprising synergistic effect from the combination.

Without being bound to a particular theory, it has been found that liquid flow-through or barrier properties of a nonwoven (porous substrate) can be controlled in three ways. First, an increase in contact angle (i.e. making the substrate more hydrophobic by a substrate surface energy that is below the surface tension of the liquid) can be achieved with additives or coatings onto the substrate. The higher contact angle makes it harder for the liquid to wet out the nonwoven and enter and penetrate through the pores. Second, the pores in the substrate can be made smaller by using smaller diameter fibers, which increases the capillary pressure. Under conditions with a contact angle above 90 degrees (i.e. when the substrate is hydrophobic and water or urine is not spontaneously wetting the substrate and getting absorbed), smaller pores increase the capillary pressure required to push liquid through the pores. (An alternate option for achieving smaller pores and barrier advantages is a compression of the fibrous substrate which leads to squeezing out void space and getting denser substrate—however with a significant loss in air permeability and breathability.) A third approach is to make a barrier substrate (complete nonwoven or a component layer of it) thicker and higher in basis weight, which then requires higher pressures (or/and longer times) for a liquid to penetrate.

Based on a desire to achieve breathable and cost-effective barrier nonwovens, the inventors believe that the most beneficial way to control liquid flow through a nonwoven (barrier) is via pore size and surface energy. Specifically beneficial is a nonwoven comprising a fiber layer with very fine fiber diameters so that a small pore size can be achieved. The pore size of the substrate of this disclosure is providing particular advantage because it exhibits are a narrower pore size distribution (smaller sized pores) based on having a smaller number-average fiber diameter and a small mass-average diameter (i.e. narrow fiber diameter distribution leading to a narrow pore size distribution). Further, the inventors have found that combining this substrate with a hydrophobic surface coating, such as a crosslinked polydimethylsiloxane coating, results in a lower surface energy of the fiber and achieves a synergistic barrier effect. The lower surface energy from the coating increases resistance to wet out on the fiber surfaces and inhibits flow thru the pores in the substrate, and then the smaller pore size creates a greater barrier for the liquid to penetrate. Overall this leads to a synergistically higher capillary pressure gradient in which fluid has to overcome to penetrate through the nonwoven, thus leading to higher strikethrough times.

Hydrophobic Surface Coating

In some embodiments, it may be desirable for the webs to comprise a hydrophobic surface coating on at least one surface or surface portion of the lightweight nonwoven laminate material. The hydrophobic surface coating may increase the low surface tension fluid strikethrough time of the SNS web and/or the SMNS web, while not significantly decreasing the air permeability.

Hydrophobic additive formulations and methods for incorporating them in nonwoven webs are described by Catalan in US applications publication Nos. 2006/0189956 filed on Feb. 18, 2005 and 2005/0177123 filed on Feb. 10, 2005, and in U.S. application Ser. No. 12/691,929 filed on Jan. 22, 2010, and U.S. application Ser. No. 12/691,934 filed on Jan. 22, 2010 both to J J Tee et al. that are all assigned to The Procter and Gamble Company.

The hydrophobic surface coating (HSC) may be provided by applying as a non-aqueous or aqueous, solventless, multicomponent, silicone composition to a surface or surface portion of the material, for example, a composition that includes a reactive vinyl functional siloxane polymer; a solvent free, silicone polymer cross-linker; and a reactive catalyst (e.g., organo-platinum) dispersed in polysiloxane. The HSC composition may be in liquid form during application to a material and/or fiber surface; however, the HSC composition, in some embodiments, should be substantially free of water or other aqueous media at the time of coating. It is believed, without being limited by theory, that a non-aqueous and solventless HSC composition provides a more uniform distribution of the silicone polymers (i.e., "actives") on the material and/or fiber surface. In certain embodiments, the HSC composition may desirably be hydrophobic to facilitate delivery of the HSC composition to a hydrophobic surface, resulting in a more uniform distribution of the HSC. In certain embodiments, the multicomponent HSC composition may include more than 95% by weight of silicone polymers (i.e., the HSC is composed almost entirely of actives), based on the weight of the HSC composition. Suitable silicone polymers include silicone MQ resins, polydimethysiloxanes, silicone liquid elastomers, and combinations thereof. Suitable polydimethylsiloxanes include vinyl-terminated polydimethylsiloxanes, methyl hydrogen dimethylsiloxanes, hydroxyl-terminated polydimethylsiloxanes, organo-modified polydimethylsiloxanes, and combinations thereof. In certain embodiments (e.g., when coating a substrate that includes cotton), an HSC that includes fluorinated polymers may be used. Suitable fluorinated polymers include telomers and polymers containing tetrafluoroethylene and/or perfluorinated alkyl chains. For example, fluorinated polymers, which are commercially available from DuPont under the tradename Zonyl® (e.g., Zonyl® 321, 329, 8740, 9027, and 9360) may be suitable.

At least some of the silicone polymers that are present in the HSC composition may be cross-linked after the HSC composition is applied to the surface of a substrate, such as a nonwoven or fiber. The polymers may be cross-linked by any suitable cross-linking process known in the art, for example, during a curing process in which a cross-linking inhibitor from the silicone composition with heat in the presence of a catalyst. During cross-linking, inter-molecular covalent bonds are formed between the silicone polymer molecules. It is believed, without being limited by theory, that the cross-linked molecules may cause the HSC composition, which is typically applied to the substrate in a liquid state, to behave more like a solid (i.e., not exhibit the tendency to flow or migrate, which is typically associated with a liquid). Thus, the cross-linked silicone polymers may help to keep the HSC composition in a desired location. The molecular weight of the silicone polymers prior to cross-linking is typically less than or equal to 4000 MW. After cross-linking, the molecular weight of the cross-linked silicone polymers on the coated surface may be more than 4000 MW; 10,000 MW; 15,000 MW; 20,000 MW; or even more than 25,000 MW. The HSC may be present on the surface of a substrate (e.g., a lightweight nonwoven laminate) in amounts of at least 1 microgram of coating per 1 gram of substrate ("µg/g"). For example, the HSC may be present on the laminate in amounts of at least about 100 µg/g; 200 µg/g; 300 µg/g or even at least 400 µg/g, as determined by a suitable silicon analysis.

The HSC compositions may be delivered to a substrate and/or fiber surface by any means commonly known in the art. One particularly suitable method of delivery is described in copending U.S. Application Ser. No. 61/156,150, filed by Tee, et al. on Feb. 27, 2009. Without being limited by theory, it is believed that the HSC compositions disclosed herein, when topically applied to the surface of a fibrous substrate (e.g., nonwoven surface), tend to envelope or at least partially coat one or more fibers and/or fibrous structures of the nonwoven in such a way that a cohesive, uniform film-like network is formed around the fiber and/or fibrous structures, and partially fills the pore network of the nonwoven. This film-like network serves to increase the barrier properties of the component, particularly when exposed to low surface energy fluids. In certain embodiments, HSC compositions may be included as an additive to a hot melt composition (e.g., blended into a thermoplastic melt), which is then formed into fibers and/or a substrate (e.g., by spunbonding, meltblowing, or extruding); however, such embodiments are generally not desirable due to the lack of a suitable film-like network being formed on the fibrous structures. The resulting fibers may exhibit suitable hydrophobic properties, but a nonwoven formed from such fibers may not exhibit the desired barrier properties. Those minute additions of hydrophobic materials (chemical components) may increase the contact angle of the fibers with liquid to some degree; namely for 1000 µg/g the contact angle for water increases from 100 to 110 degrees.

Figure 6:
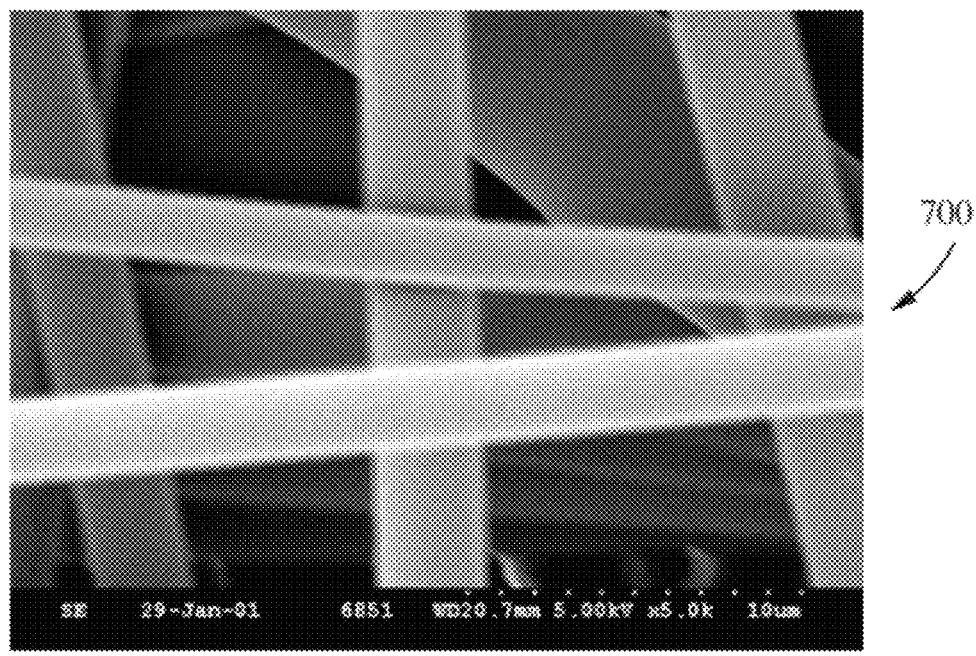
FIG. 6 is a micrograph of a nonwoven.
Figure 7:
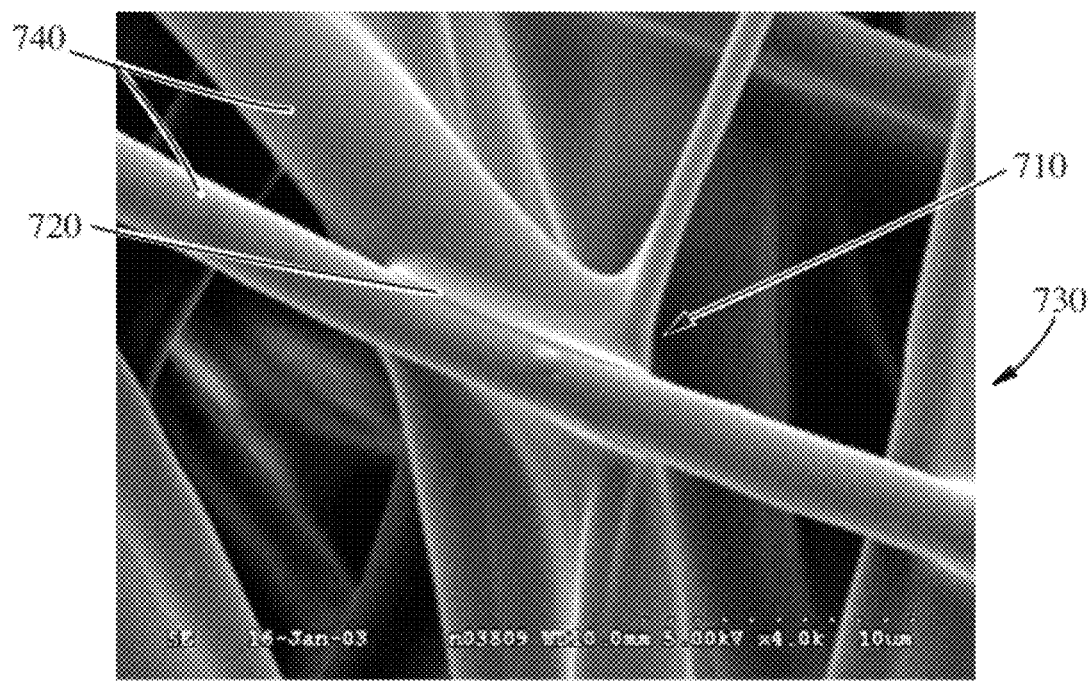
FIG. 7 is a micrograph of a nonwoven treated with a hydrophobic surface coating.

FIG. 6 shows a micrograph of an uncoated 15 gsm melt-blown nonwoven 700. In FIG. 7, the nonwoven 700 of FIG. 6 is treated with an HSC 710 to form a coated nonwoven 730, which includes a non-aqueous, solventless, multicomponent, silicone composition. Here, the film-like network 720 is formed between the fibrous structures 740 of the coated nonwoven 730. In certain embodiments, the HSC 710 may be elastomeric. Accordingly, when deposited onto one or more surfaces of an absorbent article component, the HSC 710 may provide at least some elastic properties to the article component when stretched.

It is believed that the HSC composition disclosed herein may provide improved distribution of the actives as compared to an aqueous coating composition that includes a hydrophobic active component (e.g., provides a more uniform HSC). Improved distribution of the actives means that the treated component and/or component portion exhibits improved barrier properties, as evidenced by a higher strike-through time. Suitable strike-through times include strike-through times of greater than 12 seconds, when measured according to the Liquid Strike-through Test described below. For example, strike-through time of between 12 and 20 seconds, 14 and 18 seconds, or even between 15 and 17 seconds. Further, the HSC compositions described herein do not include the additional additives (e.g., surfactants and stabilizers) that are typically included in aqueous compositions, and therefore may demonstrate reduced, and ideally no, migration of actives, as compared to conventional coating compositions.

Table 1 below illustrates the strike-through time for a lightweight nonwoven laminate coated with an HSC as disclosed herein. The laminate is a 15 gsm nonwoven available from Polymer Group, Inc., Charlotte, N.C. The nonwoven is a polypropylene, SMS trilaminate configured such that the layers have a basis weight of 7 gsm; 1 gsm; 7 gsm, respectively. The strike-through times are measured on an uncoated sample, a sample coated with an aqueous composition that includes a hydrophobic active component, and an HSC as disclosed herein. The aqueous composition is a 10.4% by weight total actives solution, based on the total weight of the composition. The composition is a mixtures of 25% by weight of SM3200 brand 40% emulsion; 0.5% by weight of SM3010 brand 40% emulsion with catalyst; and 74% water. The SM3200 and SM3010 brand 40% active emulsions are available from Momentive Chemicals. The HSC composition is a 100% active, multicomponent, silicone composition of 92% SylOFF 9110 brand silicone polymer, 5% SylOFF 7682-0000 brand silicone polymer cross-linker and 3% SylOFF 4000 brand catalyst, all available from Dow Corning Corp. The strike-through times are measured according to the Liquid Strike-Through Test described below.

TABLE 1

| 15 gsm PGI nonwoven | Uncoated | Aqueous Composition | HSC Composition |
|---|---|---|---|
| Strikethrough time (s) | 6.61 | 10.92 | 15.96 |

As can be seen from Table 1, an HSC suitable for use herein provides improved strike-through times over the uncoated sample and the sample treated with the aqueous composition.

Table 2 illustrates the strikethrough times for various nonwoven laminates, with varying basis weights, and with or without the hydrophobic surface coating. The 15 gsm SMS nonwoven laminate's strikethrough time is increased when there is a hydrophobic surface coating. For a lower basis weight, 13 gsm, nonwoven laminate that is SMNS, the addition of the hydrophobic surface coating results in an increase of the strikethrough time is even more pronounced. The data demonstrates the synergistic effect of combining a nonwoven component layer having fine fibers ("N-fibers") (smaller pore size) with the disclosed hydrophobic surface coatings (lower surface energy).

TABLE 2

| Sample # | Substrate Type | Low ST Strikethrough (2 ply) Large Head |
|---|---|---|
| 1 | 15 gsm SMS | 6-8 s |
| 2 | 15 gsm SMS w/ HSC Gen 2 | 15-18 s |
| 3 | 13 gsm SMNS | 11-15 s |
| 4 | 13 gsm SMNS w/ HSC Gen 2 | 26-30 s |
| 5 | 17 gsm SMS | 10-15 s |

Figure 5:
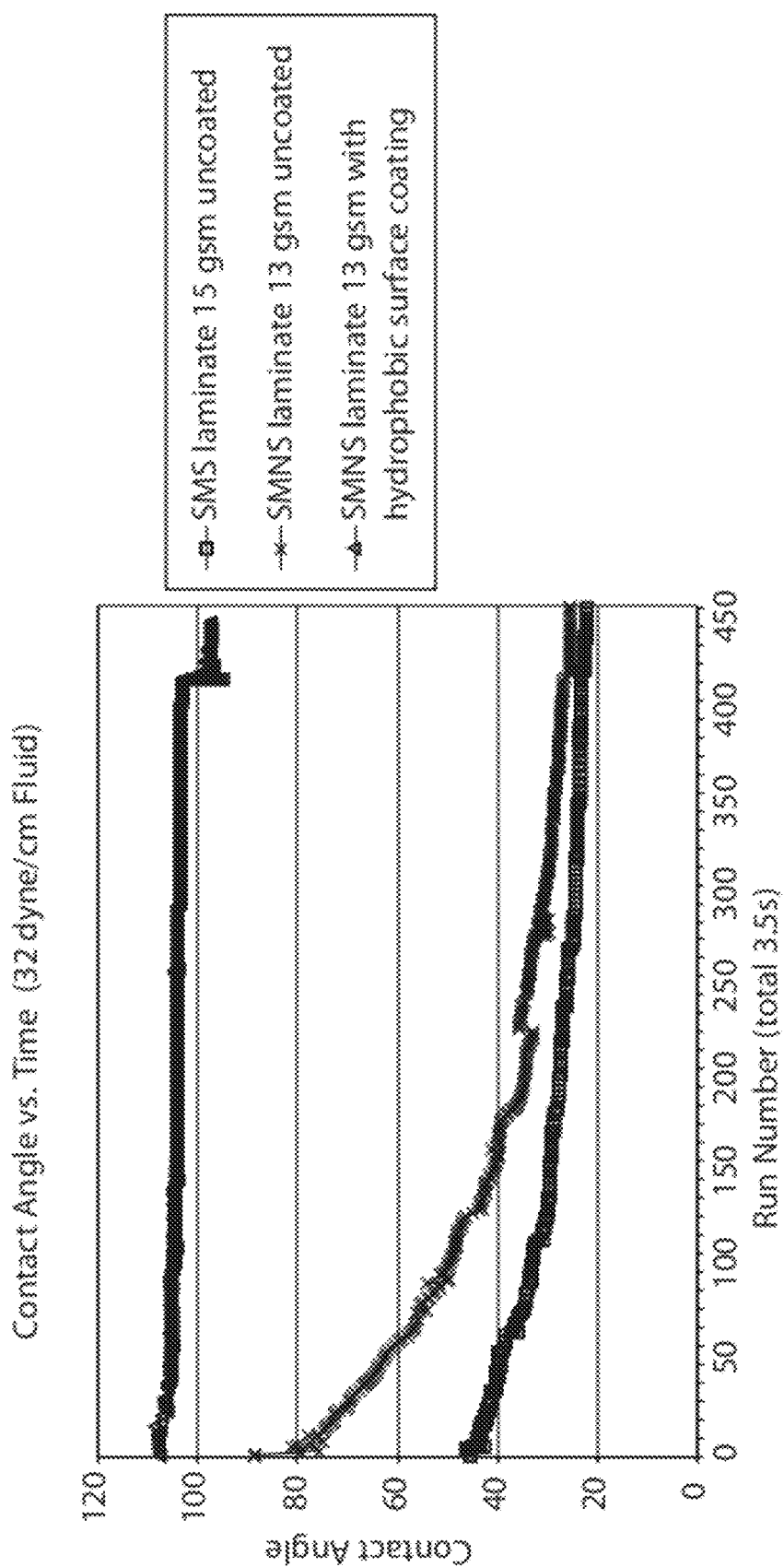
FIG. 5 is a graph of contact angle vs. time for a low surface tension fluid on various nonwoven laminates.

FIG. 5 illustrates the contact angles of a low surface tension fluid (32 dynes/cm) on various nonwoven laminates with varying basis weights and with or without the hydrophobic surface coating. The lowest line represents the performance of a 15 gsm SMS laminate that is uncoated. It has the lowest contact angle over time meaning that fluid can flow and penetrate easier into the substrate. The addition of N fiber layer as represented by the middle line, a SMNS laminate at lower basis weight of 13 gsm, results in a higher initial contact angle which improves barrier but decreases over time. The addition of the hydrophobic surface coating on the 13 gsm SMNS laminate, as represented by the top line, shows the highest contact angle over time, meaning that the low surface tension fluid will have significant less spreading and penetration unto the substrate. The synergistic effect of lower pore size distribution by the N fiber layer with the surface energy reduction provided by the hydrophobic surface coatings enhances barrier properties of the SMNS laminate with hydrophobic surface coating.

In some embodiments, these hydrophobic surface coatings may be deposited onto the surface of the SNS web and/or the SMNS web in amounts of from at least 1 μg of coating per 1 g of a web. A suitable amount of silicone polymer present on the surface may be at least 100 μg/g. In certain embodiments, the amount of silicone polymer present on the surface may be at least 200 μg/g. In other embodiments, the amount of silicone polymer present on the surface may be at least 300 μg/g, alternatively, at least 400 μg/g or, alternatively, in the range of 1000 μg/g to 10,000 μg/g, for example.

In one embodiment, a web of material comprising a hydrophobic surface coating and/or a hydrophobic melt additive, such as an SNS web or an SMNS web comprising these materials, for example, may have a total basis weight of less than 30 gsm, alternatively, less than 15 gsm, e.g., 13 gsm, alternatively, less than 10 gsm, and alternatively, in the range of 7 gsm to 15 gsm. In such an embodiment, the web of material may not comprise a film and may have an air permeability of at least 1 $m^3/m^2$/min, alternatively, at least 10 $m^3/m^2$/min, alternatively, at least 20 $m^3/m^2$/min, and alternatively, at least 40 $m^3/m^2$/min but less than 100 $m^3/m^2$/min. In one embodiment, the web of material may have a local basis weight variation of less than 10%, alternatively, less than 8%, and alternatively, less than 6% and a 32 mN/m low surface tension fluid strikethrough time of at least 30 seconds, alternatively, at least 35 seconds, alternatively, at least 40 seconds, alternatively, at least 47 seconds, alternatively, at least 50 seconds, alternatively, at least 55 seconds, alternatively, at least 60 seconds, alternatively, at least 65 seconds, and alternatively, at least 70 seconds.

In one embodiment, the webs of the present disclosure, for example, the SNS or the SMNS webs, and in the relevant comparisons, e.g., with SMS, all have a porosity (% void fraction) of over 80% (e.g., 85%). The porosity of 85% arises since the M and N fiber layers have 80% to 85% porosity and the first nonwoven component layers 132 have 85% to 92% porosity. A lower porosity may be achieved by flat calendering and reducing the breathability or by referring to a film, e.g., a microporous film, however the desired air permeabilities listed above then may become unachievable.

Absorbent Articles

As discussed in more detail below, the webs of materials incorporating the N-fiber layer may be used in the construction of various absorbent articles. In one embodiment, the absorbent articles of the present disclosure may comprise a liquid pervious topsheet, a backsheet attached or joined to the topsheet, and an absorbent core disposed between the topsheet and the backsheet. Absorbent articles and components thereof, including the topsheet, backsheet, absorbent core, and any individual layers of these components, generally have an interior surface (or wearer-facing surface) and an exterior surface (or garment-facing surface).

The following description generally discusses a suitable absorbent core, a topsheet, and a backsheet that may be used in absorbent articles, such as disposable diapers, for example. It is to be understood that this general description applies to the components of the specific absorbent article shown in FIGS. 1, 2, and 3A-3C, which are further described below, and to other absorbent articles which are described herein.

Figure 2:
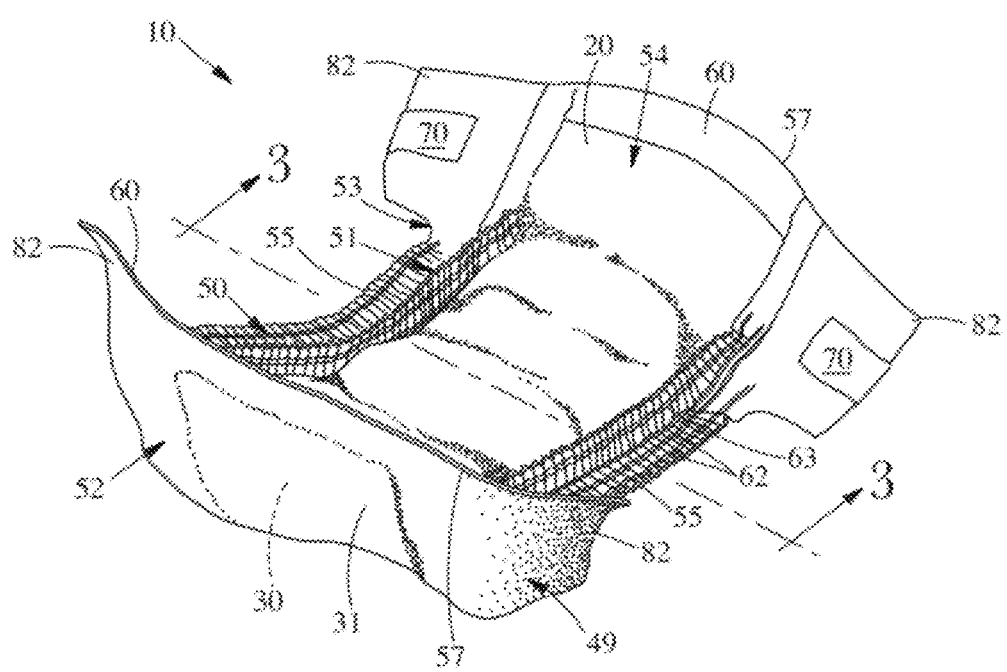
FIG. 2 is a perspective view of the absorbent article of FIG. 1.

FIG. 1 is a plan view of an absorbent article 10 in accordance with one non-limiting embodiment of the present disclosure. The absorbent article 10 is illustrated in its flat, uncontracted state (i.e., with its elastic induced contraction removed for illustration and with portions of the absorbent article 10 being cut-away to more clearly show the construction of the absorbent article 10. A portion of the absorbent article 10 which faces away from the wearer is oriented towards the viewer. FIG. 2 is a perspective view of the absorbent article 10 of FIG. 1 in a partially contracted state. As shown in FIG. 1, the absorbent article 10 may comprise a liquid pervious first topsheet 20, a liquid impervious backsheet 30 joined with the topsheet 20, and an absorbent core 40 positioned between the topsheet 20 and the backsheet 30. The absorbent core 40 has an exterior surface (or garment-facing surface) 42, an interior surface (or a wearer-facing surface) 44, side edges 46, and waist edges 48. In one embodiment, the absorbent article 10 may comprise gasketing barrier cuffs 50 and longitudinal barrier cuffs 51. The longitudinal barrier cuffs 51, in some embodiments, may extend generally parallel to a central longitudinal axis 59. For example, the longitudinal barrier cuffs 51 may extend substantially between the two end edges 57. The absorbent article 10 may comprise an elastic waist feature multiply designated as 60 (also referred to herein as a waistband or a belt) and a fastening system generally multiply designated as 70.

In one embodiment, the absorbent article 10 may have an outer surface 52, an inner surface 54 opposed to the outer surface 52, a first waist region 56, a second waist region 58, and a periphery 53 which is defined by longitudinal edges 55 and the end edges 57. (While the skilled artisan will recognize that an absorbent article, such as a diaper, is usually described in terms of having a pair of waist regions and a crotch region between the waist regions, in this application, for simplicity of terminology, the absorbent article 10 is described as having only waist regions comprising a portion of the absorbent article which would typically be designated as part of the crotch region). The inner surface 54 of the absorbent article 10 comprises that portion of the absorbent article 10 which is positioned adjacent to the wearer's body during use (i.e., the inner surface 54 is generally formed by at least a portion of the first topsheet 20 and other components that may be joined to the topsheet 20). The outer surface 52 comprises that portion of the absorbent article 10 which is positioned away from the wearer's body (i.e., the outer surface 52 is generally formed by at least a portion of the backsheet 30 and other components that may be joined to the backsheet 30). The first waist region 56 and the second waist region 58 extend, respectively, from the end edges 57 of the periphery 53 to the lateral centerline (cross-sectional line 3-3) of the absorbent article 10.

FIG. 2 shows a perspective view of the absorbent article 10 which comprises a pair of longitudinal barrier cuffs 51 in accordance with one non-limiting embodiment of the present disclosure. FIG. 3 depicts a cross-sectional view taken along line 3-3 of FIG. 1.

Figures 1, 3A:
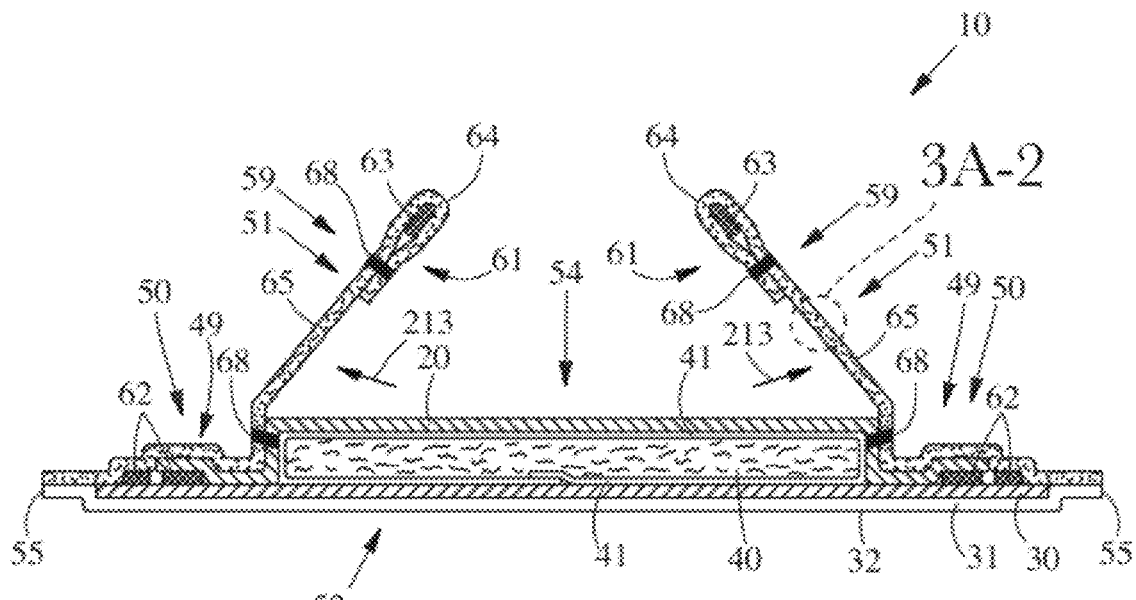
FIG. 3A is a cross-sectional view of an exemplary absorbent article through sectional line 3-3.
Figures 2, 3A:
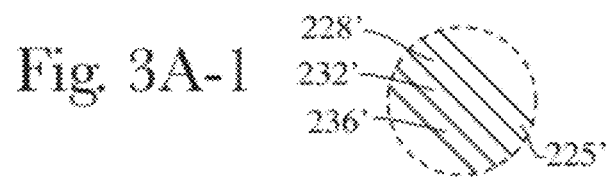
Figure 3B:
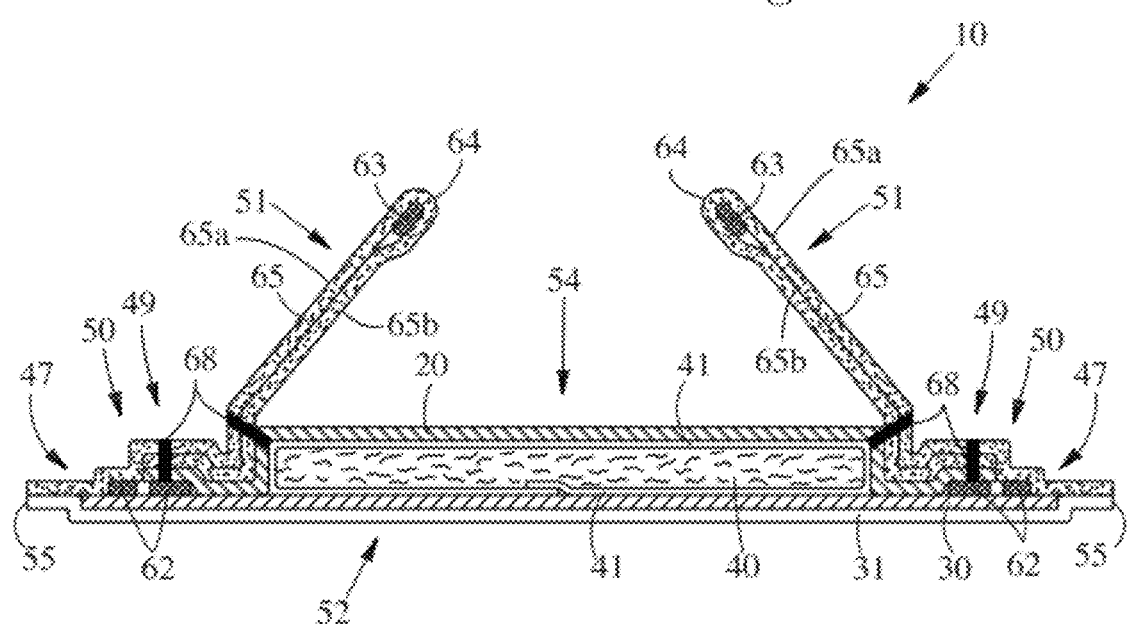
FIG. 3B is a cross-sectional view of an exemplary absorbent article through sectional line 3-3.

In one embodiment, the absorbent core 40 may take on any size or shape that is compatible with the absorbent article 10. In one embodiment, the absorbent article 10 may have an asymmetric, modified T-shaped absorbent core 40 having a narrowing of the side edge 46 in the first waist region 56, but remaining generally rectangular-shaped in the second waist region 58. Absorbent core construction is generally known in the art. Various absorbent structures for use as the absorbent core 40 are described in U.S. Pat. Nos. 4,610,678, issued to Weisman et al., on Sep. 9, 1986, 4,673,402, issued to Weisman, et al., on Jun. 16, 1987, 4,888,231, issued to Angstadt, on Dec. 19, 1989, and 4,834,735, issued to Alemany et al., on May 30, 1989. In one embodiment, the absorbent core 40 may comprise a dual core system containing an acquisition/distribution core of chemically stiffened fibers positioned over an absorbent storage core as described in U.S. Pat. Nos. 5,234,423, issued to Alemany, et al., on Aug. 10, 1993, and 5,147,345, issued to Young et al., on Sep. 15, 1992. The absorbent core 40 may also comprise a core cover 41 (as shown in FIGS. 3A-B and as described in detail below) and a nonwoven dusting layer that is disposed between the absorbent core 40 and the backsheet 30.

In one embodiment, the topsheet 20 of the absorbent article 10 may comprise a hydrophilic material that promotes rapid transfer of fluids (e.g., urine, menses, and/or runny feces) through the topsheet 20. The topsheet 20 may be pliant, soft feeling, and non-irritating to the wearer's skin. Further, the topsheet may be fluid pervious, permitting fluids (e.g., menses, urine, and/or runny feces) to readily penetrate through its thickness. In one embodiment, the topsheet 20 may be made of a hydrophilic material or at least the upper surface of the topsheet may be treated to be hydrophilic so that fluids will transfer through the topsheet more rapidly and enter the absorbent core 40. This diminishes the likelihood that body exudates will flow off of the topsheet 20 rather than being drawn through the topsheet 20 and being absorbed by the absorbent core 40. The topsheet 20 may be rendered hydrophilic by treating it with a surfactant, for example. Suitable methods for treating the topsheet 20 with a surfactant comprise spraying the topsheet 20 with the surfactant and immersing the topsheet 20 into the surfactant. A more detailed discussion of such a treatment is contained in U.S. Pat. Nos. 4,988,344, issued to Reising, on Jan. 29, 1991, and 4,988,345, issued to Reising, on Jan. 29, 1991.

In one embodiment, the backsheet 30 may be impervious, or at least partially impervious, to low surface tension fluids (e.g., menses, urine, and/or runny feces). The backsheet 30 may be manufactured from a thin plastic film, although other flexible fluid impervious materials may also be used. The backsheet 30 may prevent, or at least inhibit, the exudates absorbed and contained in the absorbent core 40 from wetting articles which contact the absorbent article 10, such as bedsheets, clothing, pajamas, and undergarments, for example. The backsheet 30 may comprise a woven or a nonwoven web, polymeric films such as thermoplastic films of polyethylene or polypropylene, and/or composite materials such as a film-coated nonwoven material or a film-nonwoven laminate. In one embodiment, a suitable backsheet 30 may be a polyethylene film having a thickness of from 0.012 mm (0.5 mils) to 0.051 mm (2.0 mils). Exemplary polyethylene films are manufactured by Clopay Corporation of Cincinnati, Ohio, under the designation P18-1401 and by Tredegar Film Products of Terre Haute, Ind., under the designation XP-39385. The backsheet 30 may be embossed and/or matte finished to provide a more cloth-like appearance. Further, the backsheet 30 may permit vapors to escape from the absorbent core 40 (i.e., the backsheet 30 is breathable and has an adequate air permeability), while still preventing exudates from passing through the backsheet 30. The size of the backsheet 30 may be dictated by the size of the absorbent core 40 and the exact absorbent article design selected. In one embodiment, the backsheet 30 may comprise an SNS and/or an SMNS web, as described in greater detail below.

Other optional elements of the absorbent article 10 may comprise a fastening system 70, elasticized side panels 82, and a waist feature 60. The fastening system 70 allows for the joining of the first waist region 56 and the second waist region 58 in an overlapping configuration such that lateral tensions are maintained around the circumference of the absorbent article 10 to maintain the absorbent article 10 on the wearer. Exemplary fastening systems 70 are disclosed in U.S. Pat. Nos. 4,846,815, issued to Scripps, on Jul. 11, 1989, 4,894,060, issued to Nestegard, on Jan. 16, 1990, 4,946,527, issued to Battrell, on Aug. 7, 1990, 3,848,594, issued to Buell, on Nov. 19, 1974, 4,662,875, issued to Hirotsu et al., on May 5, 1987, and 5,151,092, issued to Buell et al., on Sep. 29, 1992. In certain embodiments, the fastening system 70 may be omitted. In such embodiments, the waist regions 56 and 58 may be joined by the absorbent article manufacturer to form a pant-type diaper having a preformed waist opening and leg openings (i.e., no end-user manipulation of the diaper is needed to form the waist opening and leg openings). Pant-type diapers are also commonly referred to as "closed diapers," "prefastened diapers," "pull-on diapers," "training pants," and "diaper-pants". Suitable pants are disclosed in U.S. Pat. Nos. 5,246,433, issued to Hasse et al., on Sep. 21, 1993, 5,569,234, issued to Buell et al., on Oct. 29, 1996, 6,120,487, issued to Ashton, on Sep. 19, 2000, 6,120,489, issued to Johnson et al., on Sep. 19, 2000, 4,940,464, issued to Van Gompel et al., on Jul. 10, 1990, and 5,092,861, issued to Nomura et al., on Mar. 3, 1992. Generally, the waist regions 56 and 58 may be joined by a permanent or refastenable bonding method.

In certain embodiments, the absorbent article 10 may comprise at least one barrier member. In one embodiment, barrier members are physical structures joined to, applied to, and/or formed with the absorbent article 10 to improve the barrier properties of the absorbent article 10. In one embodiment, barrier members may comprise structures such as a core cover, an outer cover, a longitudinal barrier cuff, a gasketing cuff, an elasticized topsheet, and combinations thereof. It may be desirable that a barrier member comprise the SNS web and/or the SMNS web, as described in further detail below.

In one embodiment, the absorbent article 10 may comprise one or more longitudinal barrier cuffs 51 which may provide improved containment of fluids and other body exudates. The longitudinal barrier cuffs 51 may also be referred to as leg cuffs, barrier leg cuffs, longitudinal leg cuffs, leg bands, side flaps, elastic cuffs, or "stand-up" elasticized flaps. Elasticity may be imparted to the longitudinal barrier cuffs 51 by one or more elastic members 63. Elastic members 63 may provide elasticity to the longitudinal barrier cuff 51 and may aid in keeping longitudinal barrier cuff 51 in a "stand-up" position. U.S. Pat. No. 3,860,003, issued to Buell, on Jul. 14, 1975, describes a disposable diaper that provides a contractible leg opening having a side flap and one or more elastic members to provide an elasticized leg cuff. U.S. Pat. Nos. 4,808,178 and 4,909,803 issued to Aziz et al. on Feb. 28, 1989 and Mar. 20, 1990, respectively, describe absorbent articles comprising "stand-up" elasticized flaps that improve the containment at the leg regions of the absorbent article 10. Additionally, in some embodiments, the one or more longitudinal barrier cuffs 51 may be intergral with one or more gasketing cuffs 50. For example, the longitudinal barrier cuffs 51 and the gasketing cuffs 50 may be formed from a single web of material, as illustrated in FIGS. 3A-3B. As with the longitudinal barrier cuffs 51, the gasketing cuffs 50 may comprises one or more elastic members 62.

In certain embodiments, the absorbent article 10 may comprise an outer cover 31. The outer cover 31 may cover all of, or substantially all of, the exterior surface of the absorbent article 10. In some embodiments, the outer cover 31 may be coterminous with the backsheet 30. The outer cover 31 may be bonded to a portion of the backsheet 30 to form a laminate structure. Bonding may be performed by any conventional methods, such as adhesive bonding, mechanical bonding, and thermal bonding, for example. The outer cover 31 may be utilized to provide extra strength or bulk to the absorbent article 10. Outer covers 31 are often used to improve the aesthetic quality of the exterior surface of the absorbent article 10. It is also desirable that the exterior surface of the absorbent article 10 exhibit a cloth-like look and feel, as such features are pleasing to consumers. Various materials are suitable for use as the outer cover 31. Such materials comprise woven webs, foams, scrims, films, and loose fibers. However, in certain embodiments, the outer cover 31 may be constructed to provide increased barrier protection. In certain embodiments, the outer cover 31 may comprise an SNS web and/or an SMNS web.

Figure 3C:
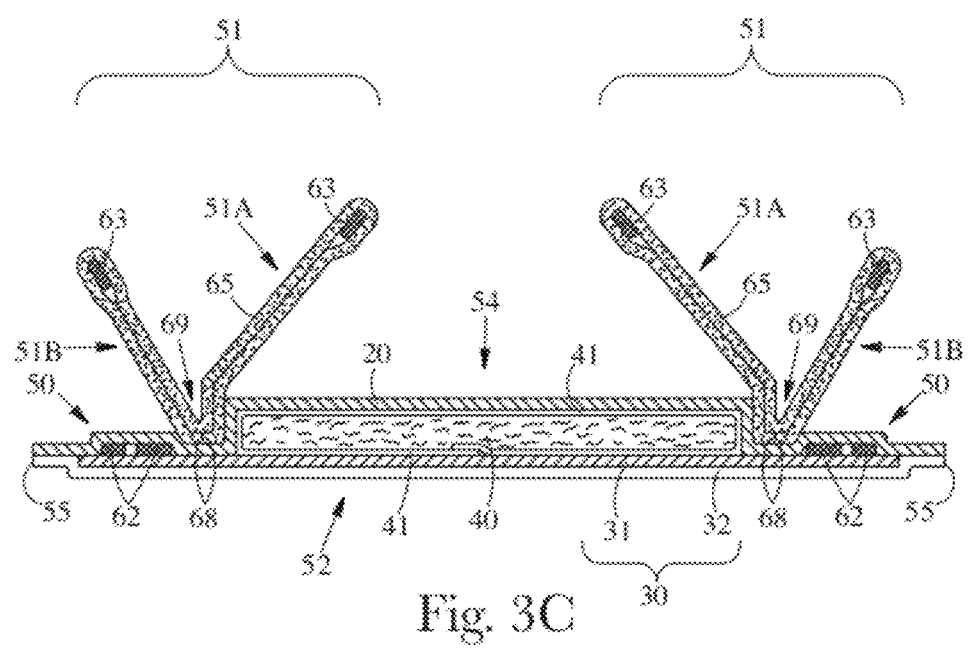
FIG. 3C is a cross-sectional view of an exemplary absorbent article through sectional line 3-3.

FIGS. 3A-C each depict a cross-sectional view of an exemplary cuff configuration along line 3-3 of FIGS. 1 and 2. A gasketing cuff 50 and a barrier cuff 51 are both shown in FIGS. 3A-C, but a single cuff design is equally feasible. FIG. 3A illustrates an exemplary gasketing cuff 50 and barrier cuff 51 configuration. Both cuffs 50 and 51 may share a common substrate 65 along one of their interior and/or exterior surfaces. Barrier cuff 51 is shown in a single layer configuration where a substantial portion of the lateral width the cuff 51 comprises a single ply of the substrate 65. FIG. 3B illustrates an exemplary gasketing cuff 50 and barrier cuff 51 configuration with the barrier cuff 51 in a multiple layer configuration. In the multiple layer configuration, at least two plies of the web (such as an SNS web or an SMNS web, for example) exist over a substantial portion of the lateral width of the cuff 51. One or more elastic members 62, 63 may be used in each gasketing cuff 50 and/or barrier cuff 51. A variety of suitable materials may be used as the web 65 in the cuffs described above. Suitable embodiments may have the web 65 comprising a plurality of layers, such as two spunbond layers and at least one N-fiber layer disposed between the two spunbond layers, for example, as described in greater detail below.

FIG. 3C illustrates an exemplary dual barrier cuff 51 design having a first barrier cuff 51A and a second barrier cuff 51B. The barrier cuff 51 may include a substrate 65 that forms portions of both the first barrier cuff 51A and the second barrier cuff 51B. The first barrier cuff 51A may be positioned nearer to the longitudinal centerline 59 (shown in FIG. 1) than the second barrier cuff 51B, which may be positioned nearer to the longitudinal edges 55 of the diaper 10. The substrate 65 may envelop an elastic member 63 that may be present in the first barrier cuff 51A and/or the second barrier cuff 51B. Generally, the first barrier cuff 51A and the second barrier cuff 51B contain at least one elastic member 63 enveloped by the substrate 65. The substrate 65 may include two edges 68 joined together at a bond site 69. The edges 68 may be configured in an abutting manner as shown in FIG. 3C; however, other configurations are contemplated herein including configuring the edges 68 in an overlapping manner. In certain embodiments of the dual cuff design, the substrate 65 may be continuous. Dual barrier cuffs 51 made from a continuous or discontinuous substrate 65 are more fully described in U.S. Publication No. 2005/0234411, filed on Apr. 14, 2004, by Ashton, et al. A continuous substrate 65 is shown in FIG. 3C. The substrate 65 forms a continuous path between the opposing edges 68. Along the continuous path, the structure of the first barrier cuff 51A and the second barrier cuff 51B may be formed and the elastic members 63 may be enveloped. The edges 68 may be attached to each other and/or to the diaper 10 at a common bond site 69.

As shown in FIGS. 3A-C, a core cover 41 may be included in certain embodiments of the diaper 10. The core cover 41 may provide structural integrity to the absorbent core assembly 40. The core cover 41 may contain the core 40 components such as cellulosic material and absorbent gelling material, both of which may tend to migrate, move, or become airborne without a physical barrier. The core cover 41 may entirely envelop the absorbent core assembly 40, as shown in FIGS. 3A-B, or may only partially cover the absorbent core assembly 40. The core cover 41 may include a suitable nonwoven, for example, a lightweight nonwoven laminate.

Figure 4:
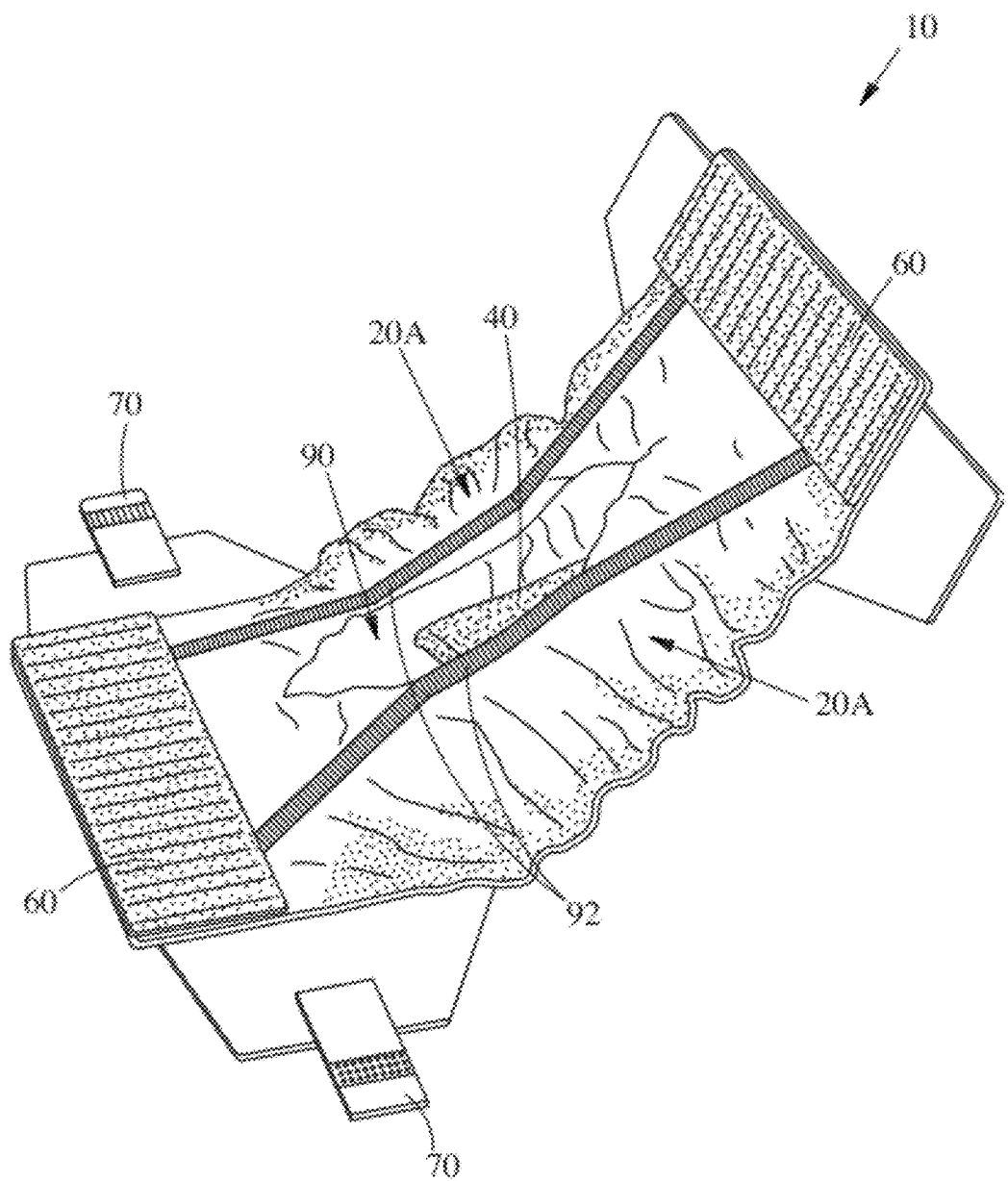
FIG. 4 shows a perspective view of an exemplary absorbent article.

In certain embodiments, the diaper 10 may comprise an elasticized topsheet 21A to provide one or more compartments for receiving and storing body exudates, particularly bowel movements. FIG. 4 shows an exemplary elasticized topsheet 20A. Elasticized topsheets 21A and articles containing them are described in U.S. Pat. No. 6,482,191. FIG. 4 shows the elasticized topsheet 21A with an elongate slit opening 90 and a pair of elastic members 92. The elongate slit opening 90 is provided to allow passage of body exudates into the interior of the diaper 10. The elastic members 92 may provide sufficient tension to the elasticized topsheet 21A so that the topsheet 21A will not sag while in use. While the elasticized topsheet 21A may include any of the material listed above in regard to traditional topsheets, it may be desirable that the elasticized topsheet 21A exhibit some degree of hydrophobicity (e.g., by including a lightweight nonwoven laminate coated with an HSC in the elasticized topsheet 21A). A hydrophobic elasticized topsheet 21A may prevent body exudates stored within the diaper 10 from seeping through the elasticized topsheet 21A and contacting the wearer's skin.

FIG. 8 shows a schematic diagram of a forming machine 110 used to make a nonwoven web 112, such as an SNS web or an SMNS web, for example, in accordance with one embodiment. To make an SMNS web, the forming machine 110 is shown as having a first beam 120 for producing first coarse fibers 135, an optional second beam 121 for producing intermediate fibers 127 (e.g., meltblown fibers), a third beam 122 for producing fine fibers 131 (e.g., N-fibers), and a fourth beam 123 for producing second coarse fibers 124. The forming machine 110 may comprise an endless forming belt 114 which travels around rollers 116, 118 so the forming belt 114 is driven in the direction as shown by the arrows 114. In various embodiments, if the optional second beam 121 is utilized, it may be positioned intermediate the first beam 120 and the third beam 122 (as illustrated), or may be positioned intermediate the third beam 122 and the fourth beam 124, for example.

In one embodiment, the first beam 120 may produce first coarse fibers 135, such as by use of a conventional spunbond extruder with one or more spinnerets which form continuous fibers of polymer. Forming spunbond fibers and the design of such a spunbond forming first beam 120 is within the ability of those of skill in the art. Spunbond machines may be acquired from Reicofil GmbH in Troisdorf, Germany, for example. Suitable thermoplastic polymers comprise any polymer suitable for spunbonding such as polyesters, including PET and PBT, polylactic acid (PLA), and alkyds, polyolefins, including polypropylene (PP), polyethylene (PE), and polybutylene (PB), olefinic copolymers from ethylene and propylene, elastomeric polymers including thermoplastic polyurethanes (TPU) and styrenic block-copolymers (linear and radial di- and tri-block copolymers such as various types of Kraton), polystyrenes, polyamides, PHA (polyhydroxyalkanoates) and e.g. PHB (polyhydroxubutyrate), and starch-based compositions including thermoplastic starch, for example. The above polymers may be used as homopolymers, copolymers, e.g., copolymers of ethylene and propyelene, blends, and alloys thereof. The polymer is heated to become fluid, typically at a temperature of 100-350° C., and is extruded through orifices in the spinneret. The extruded polymer fibers are rapidly cooled and attenuated by air streams to form the desired denier fibers. The first coarse fibers 135 resulting from the first beam 120 may be dispensed or laid onto the forming belt 114 to create a first nonwoven component layer 136. The first nonwoven component layer 136 may be produced from multiple beams or spinnerets of the type of the first beam 120, but still creates one nonwoven component layer when the fibers produced from the multiple beams or spinnerets are of the same diameter, shape, and composition. The first beam 120 may comprise one or more spinnerets depending upon the speed of the process or the particular polymer being used. The spinnerets of the first beam 120 may have orifices with a distinct shape that imparts a cross-sectional shape to the first coarse fibers 135. In one embodiment, the spinnerets may be selected to yield fibers with cross-sectional shapes including, but not limited to, circular, oval, rectangular, square, triangular, hollow, multi-lobal, irregular (i.e., nonsymmetrical), and combinations thereof.

In one embodiment, the second beam 121, if used, may produce intermediate diameter fibers 127, such as meltblown fibers, for example. The meltblown process results in the extrusion of a thermoplastic polymer through a die 119 containing a plurality of orifices. In some embodiments, the die 119 may contain from 20 to 100, or even more, orifices per inch of die width. As the thermoplastic polymer exits the die 119, high pressure fluid, usually hot air may attenuate and spread the polymer stream to form the intermediate fibers 127. The intermediate fibers 127 resulting from the second beam 121 may be dispensed or laid onto the first nonwoven component layer 136 carried by the forming belt 114, to create a fourth nonwoven component layer 128. The forth nonwoven component layer 128 may be produced from multiple, adjacent beams of the type like the second beam 121.

In one embodiment, the third beam 122 may produce the fine fibers 131 (i.e., N-fibers). In some embodiments, the N-fibers may be produced using systems and melt film fibrillation methods described in U.S. Pat. Nos. 6,315,806, 5,183, 670, and 4,536,361, to Torobin et al., and U.S. Pat. Nos.

6,382,526, 6,520,425, and 6,695,992, to Reneker et al. and assigned to the University of Akron. Other melt film fibrillation methods and systems are described in the U.S. Pat. Publ. No. 2008/0093778, to Johnson, et al., published on Apr. 24, 2008, U.S. Pat. No. 7,628,941, to Krause et al., and U.S. Pat. Publ. No. 2009/0295020, to Krause, et al., published on Dec. 3, 2009 and provide uniform and narrow fiber distribution, reduced or minimal fiber defects such as unfiberized polymer melt (generally called "shots"), fly, and dust, and further provide uniform N-fibers layer 132 for absorbent articles, such as those described by the present disclosure. The improvements in the melt film fibrillation method, specifically the design of converging-diverging gas passage specifications and the fluid curtain, described by the Johnson et al. and Krause et al., respectively, may provide the N-fibers of desired structural attributes such as number-average fiber diameter distribution, mass-average fiber diameter distribution, pore-size distribution, and structural uniformity (i.e., less local basis weight variation) for the embodiments of the present disclosure as described herein. Generally, in one embodiment, a pressurized gas stream flows within a gas passage confined between first and second opposing walls, which define respective upstream converging and downstream diverging wall surfaces. A polymer melt is introduced into the gas passage to provide an extruded polymer film on the heated wall surfaces that is impinged by the gas stream flowing within the gas passage, effective to fibrillate the polymer film into sub-micron diameter fibers or fibers. The fine fibers 131 may then be dispensed or laid onto the first nonwoven component layer 136 to create the second nonwoven component layer 132. In some embodiments, such as during the production of an SMNS web, for example, the fine fibers 131 may be dispensed or laid onto the fourth nonwoven component layer 128, which is carried on the forming belt 114. Alternatively, in some embodiments, the fine fibers 131 may be laid onto the first nonwoven component layer 136 and subsequently the intermediate fibers 127, such as meltblown fibers, may be laid onto the layer of fine fibers 131. The fine fiber layer 132 may be produced from more than one beam of the type of the third beam 122.

In one embodiment, the fourth beam 123 (or multiple beams like 120) may produce the second coarse diameter fibers 124 that are similar to the first coarse fibers 135. The second coarse fibers 124 may be dispensed or laid onto the second nonwoven component layer 132 of the web 112, such as during the production of an SNS web, for example. The resulting web 112 may be fed through thermal bonding rolls 138, 140. The bonding rolls 138, 140 are commonly referred to as a calender. The surfaces of one or both of the bonding rolls 138, 140 may be provided with a raised pattern or portions such as spots, grids, pins, or nubs, for example. In one embodiment, the bonding rolls 138, 140 may be heated to the softening temperature of the polymer used to form the nonwoven component layers of the web 112. As the web 112 passes between the heated bonding rolls 138, 140, the nonwoven component layers may be embossed by the bonding rolls 138, 140 in accordance with the pattern on the bonding rolls 138, 140 to create a pattern of discrete areas, such as calender bond 168 shown in FIG. 9. The discrete areas are bonded from nonwoven component layer to nonwoven component layer with respect to the particular fibers within each layer. Such discrete area, or calender bond site, may be carried out by heated rolls or by other suitable techniques. Another thermal fiber bonding technique comprises blowing hot air through the web 112. Air-through bonding techniques may generally be used with low melting point matrix fibers, biocomponent fibers, and powders. While a nonwoven web is described herein as comprising three to four nonwoven component layers, any suitable number of nonwoven component layers may be used and are within the scope of the present disclosure.

FIG. 9 illustrates a cross-sectional view of an SNS web at a calender bond site 168 in accordance with one non-limiting embodiment. A three layer nonwoven web 112 is illustrated that was produced by the forming machine 110 described above without the optional second beam 121 (e.g., the meltblown layer). The nonwoven web 112 may comprise a first nonwoven component layer 125 which itself may be comprised of coarse fibers, such as spunbond fibers, for example. In one embodiment, the first nonwoven component layer 125 may comprise fibers having an average diameter, alternatively, number-average diameter, in the range of 8 microns to 30 microns and, alternatively, in the range of 10 microns to 20 microns, with a relative standard deviation in the range of 4% to 10%. Stated another way, the first nonwoven component layer 125 may comprise fibers having an average denier in the range of 0.4 to 6.0, with a relative standard deviation in the range of 8% to 15%. The mass-average fiber diameter in the same embodiment may be in the range of 8 microns to 30 microns and, alternatively, in the range of 10 microns to 20 microns, with a relative standard deviation in the range of 4% to 10%. In one embodiment, the first nonwoven component layer 125 may have a basis weight in the range of 1 gsm to 10 gsm and, alternatively, in the range of 2 gsm to 7 gsm, e.g., 5.5 gsm. In certain embodiments, the fibers in the first nonwoven component layer 125 may have non-circular cross-sections, such as trilobal cross-sections, for example, or may be bicomponent fibers, such as sheath-core or side by side, for example.

In one embodiment, the nonwoven web 112 may comprise a second nonwoven component layer 132 which itself may be comprised of fine fibers, such as N-fibers. In one embodiment, the second nonwoven component layer 132 may comprise fine fibers having a number-average diameter (alternatively "average diameter") less than 1 micron, alternatively, in the range of 0.1 microns to 1 micron, alternatively in the range of 0.2 microns to 0.9 microns, alternatively in the range of 0.3 microns to 0.8 microns and, alternatively, in the range of 0.5 microns to 0.7 microns, with a relative standard deviation of less than 100%, alternatively less than 80%, alternatively less than 60%, alternatively less than 50%, such as in the range of 10% to 50%, for example; and with over 80%, such as over 90%, or 95 to 100%, for example, of the fibers having less than 1 micron diameter, i.e. submicron. The mass-average diameter of fibers in the second nonwoven component layer 132 may be less than 2 microns, alternatively, in the range of 0.1 micron to 2 microns, alternatively, in the range of 0.1 microns to 1.5 microns, alternatively, in the range of 0.1 microns to 1 micron, alternatively, in the range of 0.2 microns to 0.9 microns, alternatively, in the range of 0.3 microns to 0.8 microns and, alternatively, in the range of 0.5 microns to 0.7 microns, with a relative standard deviation of less than 100%, alternatively less than 80%, alternatively less than 60%, alternatively less than 50%, such as in the range of 10% to 50%, for example. Stated another way, the second nonwoven component layer 132 may comprise fine fibers having an average denier in the range of 0.00006 to 0.006, alternatively, in the range of 0.0002 to 0.005, alternatively, in the range of 0.0016 to 0.005, and alternatively, in the range of 0.002 to 0.004, with a relative standard deviation in the range of less than 200%, alternatively, less than 150%, and alternatively, less than 120%; and with over 80%, alternatively, over 90%, and alternatively, 95 to 100% of the fibers less than 0.006 denier.

In an embodiment with the mass-average fiber distribution of less than 1 micron, almost all the fibers must have a diameter less than 1 micron. Even with very few fibers above 1 micron, it would make the mass-average fiber diameter greater than 1 micron. Thicker fibers have larger mass; thus, the presence of thicker fibers with larger mass increases the mass-average fiber diameter more than the number-average fiber diameter as described in the Fiber Diameter Calculations set forth below. For example, a fiber with a diameter of 3 microns (a typical meltblown fiber) has 36 times more mass than a submicron N-fiber of the same length and with a typical diameter of 0.5 microns because the 3 micron fiber has a cross-sectional area 36 times larger than that of a 0.5 micron diameter fiber. Alternatively, a single 3 micron fiber diameter fiber may take the place of 36 fibers of 0.5 micron diameter, and increase the mass-average fiber diameter of the second component layer. Conversely, to reduce the mass-average fiber diameter, it is critical to reduce the number of fibers with diameter greater than 1 micron. In one embodiment, the second nonwoven component layer may comprise fibers having a number-average diameter of less than 1 micron, a mass-average diameter of less than 1.5 microns, and a ratio of the mass-average diameter to the number-average diameter less than 2. In some embodiments, the second nonwoven component layer may comprise fibers having a number-average diameter of less than 1 micron, a mass-average diameter of less than 1 micron, and a ratio of the mass-average diameter to the number-average diameter less than 1.5, for example.

Without intending to be bound by any particular theory, it is believed that the finer fibers make finer pores in the nonwoven web. As set forth herein, the finer pores provide greater fluid strikethrough performance of the nonwoven web. Therefore, it is desirable to have as many fine fibers as possible in the nonwoven web to improve low surface tension fluid strikethrough times. By reducing the number of thicker fibers and increasing the number of fine fibers less than 1 micron in the N-layer, the embodiments of the present disclosure achieve finer pore sizes and higher low surface tension fluid strikethrough times than conventional webs. In one embodiment, the mean-flow pore diameter in the second component layer 132 may be less than 20 micron, alternatively less than 15 micron, alternatively less than 10 micron, and alternatively less than 5 micron. The mean-flow pore diameter corresponds to the pressure (called mean-flow pressure) below which half the flow happens, while the rest half of the flow happens above that pressure. Since pore diameter and pressure are inversely related, smaller mean-flow pore diameter suggests higher mean-flow pressure or flow resistance that slows down the flow, and increases the fluid strikethrough time. Because the mean-flow pore diameter is a flow attribute of a structure it is distinct from the average pore diameter that is just a statistical number average of pore diameter distribution, and the average pore diameter may not correlate to any fixed flow attribute. Alternatively, the average pore diameter may not necessarily become smaller as the mean-flow pore diameter becomes smaller, e.g, as the fiber diameter is reduced. It is believed that it is critical for an embodiment of the present disclosure to have the mean-flow pore diameter in the second component layer 132 less than 20 micron, alternatively less than 15 micron, alternatively less than 10 micron, and alternatively less than 5 micron.

The pore size distribution of the nonwoven web of the present disclosure may have one or more peaks or modes (where the mode of a pore size distribution is defined as the pore size value with highest frequency) corresponding to the multiple component layers. In one embodiment, the pore size corresponding to the lowest or the first mode of the pore size distribution corresponds to the second component layer 132 comprising N-fibers. In such embodiment, the lowest or the first mode of the pore size distribution may be less than 15 micron, alternatively less than 10 micron, and alternatively 5 micron or less. As described above, smaller pore diameter suggests higher resistance to the flow, and accordingly greater fluid strikethrough time. In some embodiments, the diameter corresponding to the lowest mode (corresponding to the smallest fibers) blocks the last 20% or more of the fluid flow (that is the pore diameters larger than the lowest mode allow the 80% or less of the fluid flow). Therefore, it is believed that the smallest pores, the higher their number the better, provide the highest resistance to the flow, and increase fluid strikethrough time.

The porosity of the second component layer 132 may be greater than 50%, alternatively greater than 70%, and alternatively greater than 80%. Since porosity corresponds to the void volume through which flow may happen, lower porosity resists the flow, and accordingly increases the liquid strikethrough time. The second component layer 132 may have at least 50% fibers with the number-average diameter less than 1 micron, alternatively at least 70% fibers with the number-average diameter less than 1 micron, alternatively at least 80% fibers with the number-average diameter less than 1 micron, and alternatively at least 90% fibers with the number-average diameter less than 1 micron. Nonwoven structures with a significant number of fibers of diameter less than 1 micron have been described by Isele et al. in U.S. Pat. Publ. Nos. 2006/0014460 published on Jan. 1, 2006, and 2005/0070866 published Mar. 31, 2005, both assigned to The Procter and Gamble Company, using the methods described by Torobin et al. and Reneker et al. However, having even more than 90% fibers with diameter less than 1 micron in the second nonwoven component layer 132 is not sufficient (but necessary) to have the mass-average diameter less than 1 micron, even though the number-average diameter may be less than 1 micron as described herein. In one embodiment, the second nonwoven component layer 132 may have at least 99% of fibers with the number-average diameter less than 1 micron. Therefore, in an embodiment of the present disclosure with the second nonwoven component layer 132 comprising fibers with the mass-average diameter less than 1 micron and the number-average fiber diameter less than 1 micron, almost all the fibers may have a diameter less than 1 micron, alternatively all the fibers of the second nonwoven component layer 132 in such an embodiment are submicron.

The polydispersity of fiber diameter distribution, defined as the ratio of the mass-average diameter to the number-average diameter, of the fibers comprising the second nonwoven component layer 132 may be less than 2, alternatively less than 1.8, alternatively less than 1.5, alternatively less than 1.25, alternatively less than 1.1, and alternatively 1.0. The polydispersity of fiber diameter distribution measures the width of fiber distribution. The higher the value of the polydispersity of the distribution, the wider is the distribution. In one embodiment, as the polydispersity approaches 1, that is, the mass-average and number-average fiber diameters are the same, the second nonwoven component layer 132 may have an extremely uniform and narrow fiber distribution. The arithmetic difference between the mass-average diameter and the number-average diameter may be less than one standard deviation of the number-average diameter, alternatively, the difference may be less than three-fourths of one standard deviation of the number-average diameter, alternatively, the difference may be less than one-half of one standard deviation of the number-average diameter. Because of the above-mentioned fiber diameter averages and polydispersity of fiber diameter distribution, the N-fibers in the second nonwoven component layer 132 of the present disclosure differ from typical ultra-fine meltblown fibers that may also have the number-average diameter less than 1 micron, but typically have the mass-average diameter greater than 1 micron, and even greater than 2 microns or higher due to presence of a finite number of fibers with the diameter greater than 1 micron. As mentioned above, even with significantly large percentage of fibers, alternatively greater than 90% of fibers, having a diameter less than 1 micron, the ultra-fine meltblown fibers may not have the mass-average diameter near or less than 1 micron. The difference between the mass-average and the number-average diameters of the ultra-fine fibers may be greater than one-half of one standard deviation of the number-average diameter, more typically, the difference may be greater than one standard deviation of the number-average diameter, alternatively, the difference may be greater than two standard deviations of the number-average diameter of the ultra-fine meltblown fibers. In one embodiment, the second nonwoven component layer 132 may have a basis weight in the range of 0.1 gsm to 10 gsm, alternatively, in the range of 0.2 gsm to 5 gsm, alternatively, in the range of 0.5 to 3 gsm, and, alternatively 1 to 1.5 gsm.

In one embodiment, the nonwoven web 112 may comprise a third nonwoven component layer 136 which itself is comprised of coarse fibers, such as spunbond fibers, and may be similar to the first nonwoven component layer 125.

If the fourth nonwoven component layer 128 is used, such as a meltblown layer, these intermediate diameter fibers may comprise fibers having an average diameter, alternatively number-average diameter, in the range of 0.7 microns to 8 microns, alternatively in the range of 1 micron to 8 microns, and, alternatively, in the range of 1 micron to 5 microns, with a relative standard deviation in the range of 20% to over 100%. The mass-average diameter of the fourth nonwoven component layer 128, such as a meltblown layer, may be in range of 0.7 microns to 8 microns, alternatively in the range of 1 micron to 8 microns, and, alternatively, in the range of 1 micron to 5 microns, and alternatively in the range of 2 to 5 micron, with a relative standard deviation in the range of 20% to over 100%. In addition, the polydispersity of the fiber diameters in the intermediate fiber layer is in the range from 1 to 10, alternatively from 2 to 8, alternatively from 2 to 6, alternatively from 1.5 to 5. Stated another way, the fourth nonwoven component layer 128 may comprise fibers having an average denier in the range of 0.003 to 0.4, alternatively, in the range of 0.006 to 0.3, with a relative standard deviation of in the range of 50% to 600%, alternatively in the range of 150% to 300%. In one embodiment, the meltblower layer may have a basis weight in the range of 0.1 gsm to 10 gsm, alternatively, in the range of 0.2 gsm to 5 gsm, and, alternatively, in the range of 0.5 gsm to 3 gsm and, alternatively, in the range of 1 to 1.5 gsm.

Also, the intermediate and fine diameter fibers may be of a bicomponent or polymer blend type, for example.

In one embodiment, referring to FIGS. 1-3, the absorbent article 10 may be configured to be worn about a lower torso of a wearer. In various embodiments, the absorbent article 10 may comprise a chassis 47 comprising a topsheet 20, a backsheet 30, and an absorbent core 40 disposed between, or at least partially between, the topsheet 20 and the backsheet 30. A pair of longitudinal barrier cuffs 51 may be attached to and/or formed with a portion of the chassis 47, such as the topsheet 20, for example. Each longitudinal barrier cuff 51 may be formed of a web of material, such as an SNS web or an SMNS web. In one embodiment, the web of material may be formed of a plurality of nonwoven component layers arranged in various combinations and permutations of a plurality of spunbond, meltblown, and N-fiber layers, including but not limited to SMN, SMNMS, SMMNMS, SSMMNS, SSNNSS, SSSNSSS, SSMMNNSS, SSMMNNMS, and the like. The webs of material disclosed herein exhibit exceptional, unexpected properties when compared to related webs of material as described in further detail below.

In one embodiment, referring to FIGS. 9 and 10, a web of material 112 may comprise a first nonwoven component layer 125 comprising fibers having an average diameter in the range of 8 microns to 30 microns, a second nonwoven component layer 132 comprising fibers having a number-average diameter of less than 1 micron, a mass-average diameter of less than 1.5 micron, and a polydispersity ratio less than 2, and a third nonwoven component layer 136 comprising fibers having an average diameter in the range of from 8 microns to 30 microns. Stated another way, the web of material 112 may comprise the first nonwoven component layer 125 comprising fibers having an average denier in the range of 0.4 to 6, the second nonwoven component layer 132 comprising fibers having an average denier in the range of 0.00006 to 0.006, and a third nonwoven component layer 136 comprising fibers having an average denier in the range of 0.4 to 6. In such an embodiment, the second nonwoven component layer 132 may be disposed intermediate the first nonwoven component layer 125 and the third nonwoven component layer 136. Also, the first nonwoven component layer 125, the second nonwoven component layer 132, and the third nonwoven component layer 136 may be intermittently bonded to each other using any suitable bonding process, such as a calendering bonding process, for example. In one embodiment, the web of material 112 does not comprise a film. In various embodiments, the web of material 112 may comprise a spunbond layer, which may correspond to the first nonwoven component layer 125, an N-fiber layer, which may correspond to the second nonwoven component layer 132, and a second spunbond layer, which may correspond to the third nonwoven component layer 136, together referred to herein as an "SNS web."

Figure 11:
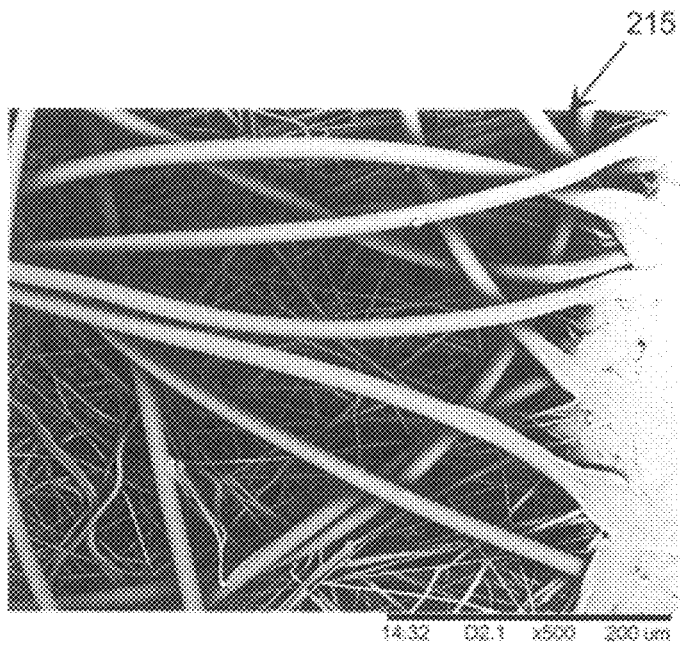
FIG. 11 is a top view photograph of a web of material.
Figure 12:
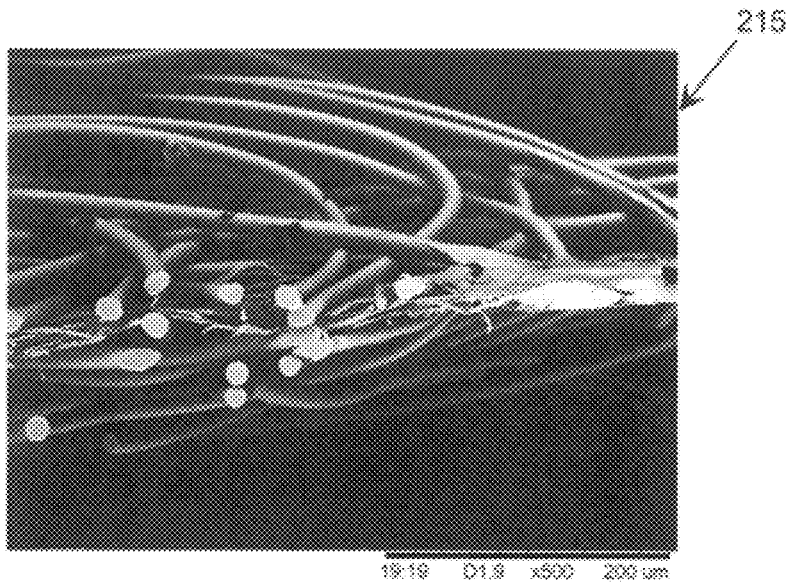
FIG. 12 is a cross-sectional photograph of the web of material of FIG. 11 taken through a calendering bond.
Figure 13:
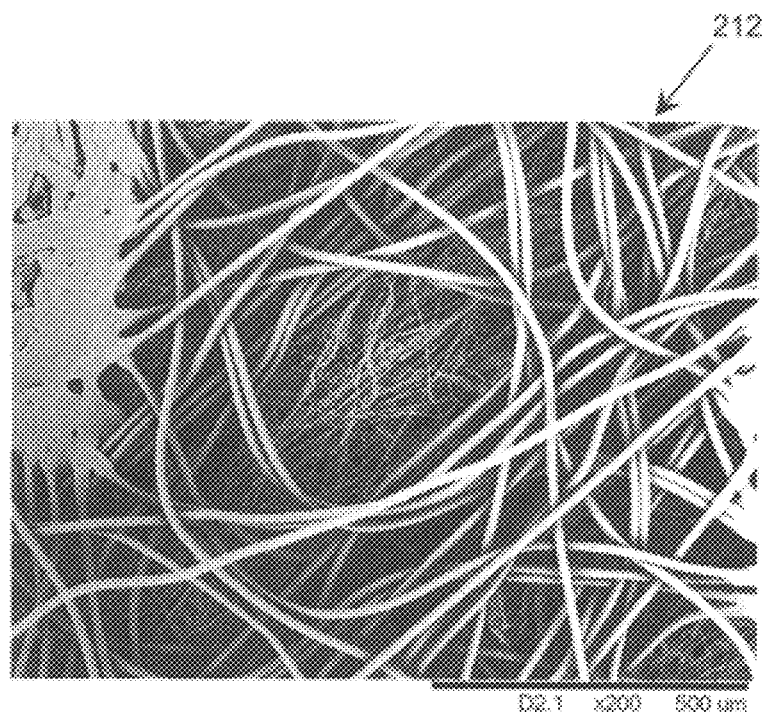
FIG. 13 is a top view photograph of a web of material in accordance with one non-limiting embodiment of the present disclosure.
Figure 14:
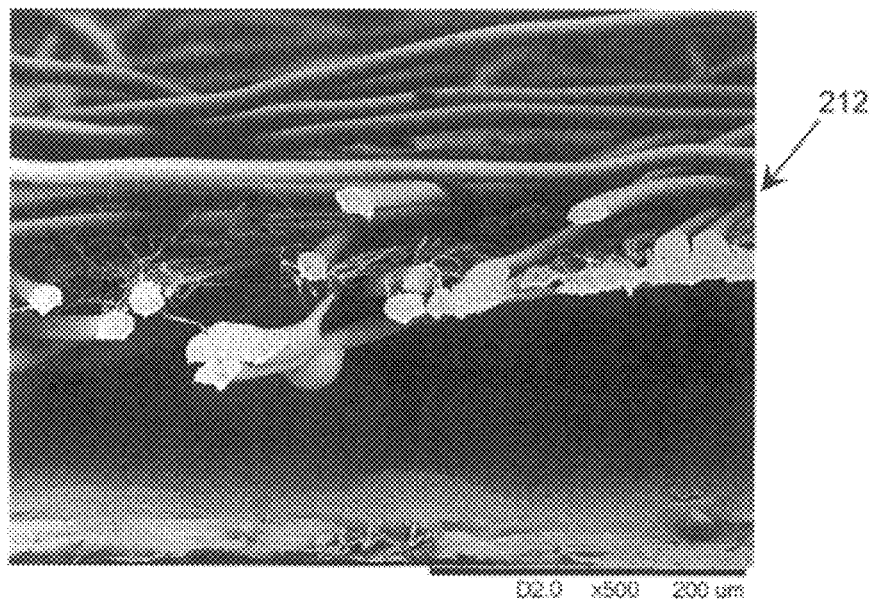
FIG. 14 is a cross-sectional photograph of the web of material of FIG. 13 taken through a calendering bond in accordance with one non-limiting embodiment of the present disclosure.

SMS (spunbond-meltblown-spunbond) webs may have pore sizes which sometimes allow low surface tension fluids to penetrate therethrough after a particular increment of time. Some photographs of such SMS webs are illustrated in FIGS. 11 and 12. FIG. 11 is a top view of an 13 gsm SMS web 215 at 500 times magnification. FIG. 12 is a cross-sectional view of the SMS web 215 of FIG. 11 taken through a calendering bond site in the SMS web at 500 times magnification. Non-limiting example photographs, which are taken using a scanning electron microscope (SEM), of an 15 gsm SNS web 212 are illustrated in FIGS. 13 and 14. FIG. 13 is a top view of the SNS web 212 at 200 times magnification. FIG. 14 is a cross-sectional view of the SNS web 212 of FIG. 13 taken through a calendering bond site in the SNS web 212 at 500 times magnification. In one embodiment, other configurations (i.e., layering patterns) of the web of material 212 are envisioned and are within the scope of the present disclosure, such as a web of material comprising a spunbond layer, an N-fiber layer, a second spunbond layer, and a third spunbond layer of different composition or fiber cross-section, for example.

In one embodiment, a web of material, such as the SNS web 212, for example, may have a total basis weight of less than 30 gsm, alternatively, less than 15 gsm, alternatively, e.g., 13 gsm, alternatively, less than 10 gsm, and alternatively, in the range of 7 gsm to 15 gsm. In such an embodiment, the web of material may not comprise a film and has an air permeability of at least 1 $m^3/m^2/min$, alternatively, at least 10 $m^3/m^2/min$, alternatively, at least 20 $m^3/m^2/min$, and alternatively, at least 40 m³/m²/min but less than 100 m³/m²/min. In one embodiment, the web of material may have a local basis weight variation of less than 10%, alternatively, less than 8%, and alternatively, less than 6%, and a 32 mN/m low surface tension fluid strikethrough time of at least 19 seconds, alternatively, at least 23 seconds, alternatively, at least 30 seconds, alternatively, at least 35 seconds, alternatively, at least 40 seconds, alternatively, at least 45 seconds, and alternatively, at least 50 seconds.

Figure 15:
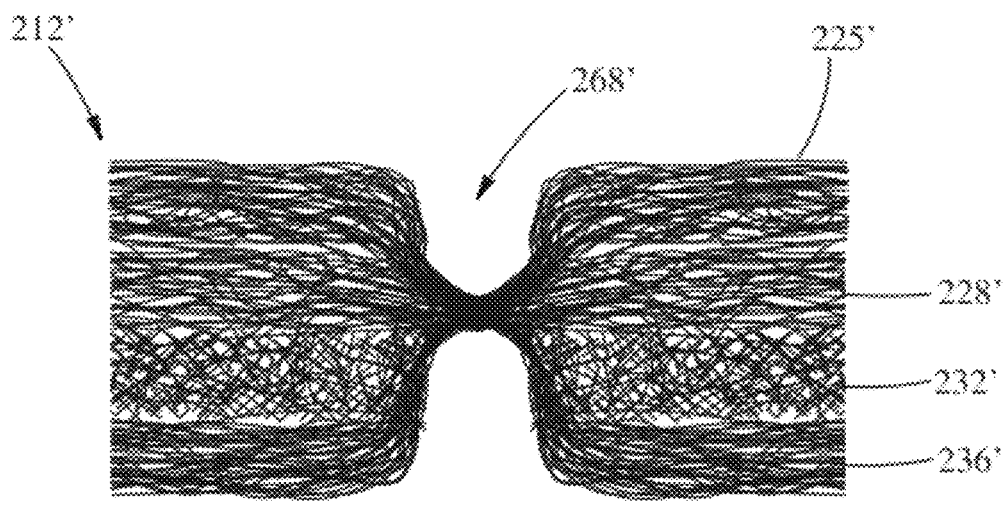
FIG. 15 is a cross-sectional view of a web of material in a four layer configuration in accordance with one non-limiting embodiment of the present disclosure.
Figure 16:
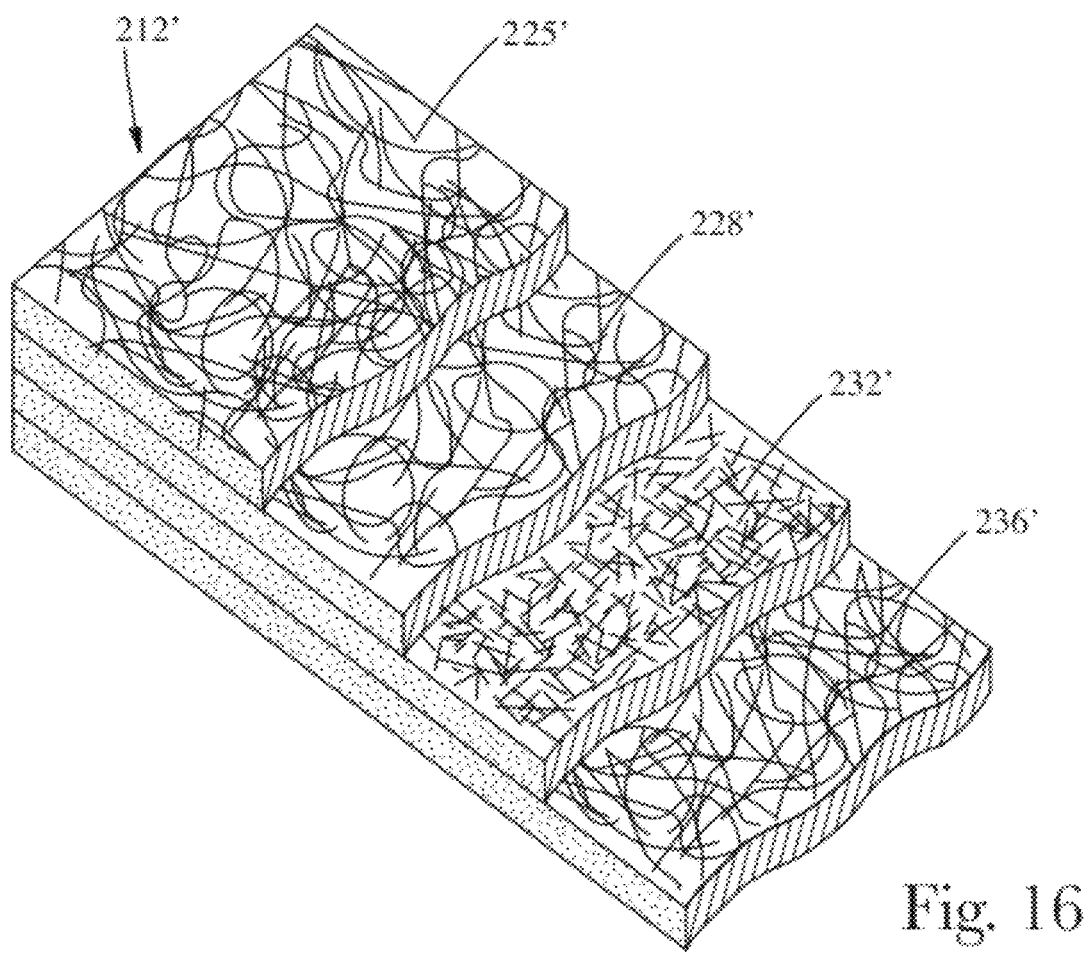
FIG. 16 is a perspective view of the web of material of FIG. 15 with various portions of nonwoven component layers cut away to show the composition of each nonwoven component layer in accordance with one non-limiting embodiment of the present disclosure.
Figure 17:
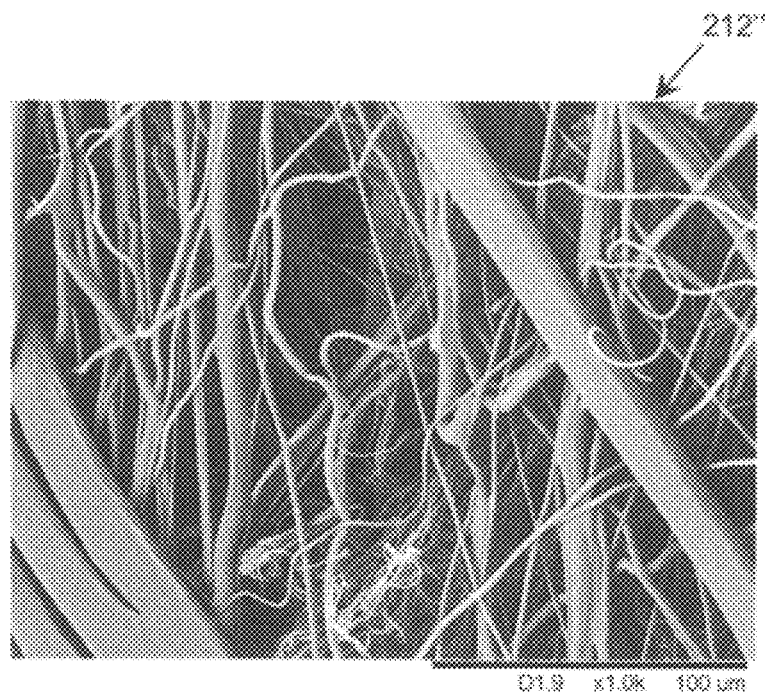
FIG. 17 is a top view photograph of a web of material in accordance with one non-limiting embodiment of the present disclosure.
Figure 18:
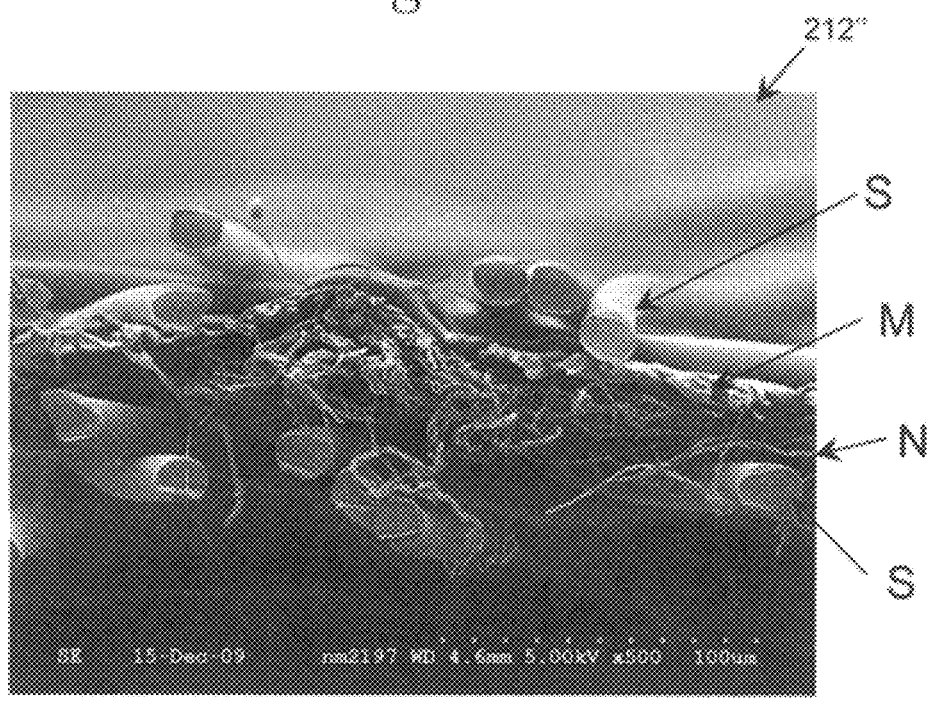
FIG. 18 is a cross-sectional photograph of the web of material of FIG. 17 in accordance with one non-limiting embodiment of the present disclosure.

In one embodiment, referring to FIGS. 15 and 16, a web of material 212' may comprise a first nonwoven component layer 225' comprising fibers having an average diameter in the range of 8 microns to 30 microns, a second nonwoven component layer 232' comprising fibers having a number average diameter of less than 1 micron, a mass-average diameter of less than 1.5 micron, and a polydispersity ratio less than 2, a third nonwoven component layer 236' comprising fibers having an average diameter in the range of 8 microns to 30 microns, and a fourth nonwoven component layer 228' comprising fibers having an average diameter in the range of 1 micron to 8 microns. Stated another way, the web of material 212' may comprise the first nonwoven component layer 225' comprising fibers having an average denier in the range of 0.4 to 6, the second nonwoven component layer 232' comprising fibers having an average denier in the range of 0.00006 to 0.006, a third nonwoven component layer 236' comprising fibers having an average denier in the range of 0.4 to 6, and a fourth nonwoven component layer 228' comprising fibers having an average denier in the range of 0.006 to 0.4. In such an embodiment, the second nonwoven component layer 232' and the fourth nonwoven component layer 228' may be disposed intermediate the first nonwoven component layer 225' and the third nonwoven component layer 236'. Also, the first nonwoven component layer 225', the second nonwoven component layer 232', the third nonwoven component layer 236', and the fourth nonwoven component layer 228' may be intermittently bonded to each other using any bonding process, such as a calendering bonding process, for example. In one embodiment, the web of material 212' does not comprise a film. In various embodiments, the web of material 212' may comprise a spunbond layer, which may correspond to the first nonwoven component layer 225', a meltblown layer, which may correspond to the fourth nonwoven component layer 228', an N-fiber layer, which may correspond to the second nonwoven component layer 232' and a second spunbond layer, which may correspond to the third nonwoven component layer 236', together referred to herein as an "SMNS web." Non-limiting example photographs, which are taken using a scanning electron microscope, of an SMNS web 212" are illustrated in FIGS. 17 and 18. FIG. 17 is a top view of the SMNS web 212" at 1000 times magnification. FIG. 18 is a cross-sectional view of the SMNS web 212" of FIG. 17 at 500 times magnification. In one embodiment, other configurations of webs of material are envisioned and are within the scope of the present disclosure, such as a web of material comprising a spunbond layer, a meltblown layer, an N-fiber layer, a second spunbond layer, and a third spunbond layer of different structure or composition, for example.

In one embodiment, referring to FIG. 1, the chassis 47 may define the two end edges 57, and the central longitudinal axis 59 may be defined in the chassis 47 and extend from one midpoint of an end edge 57 to the midpoint of the other end edge 57. In various embodiments, referring to FIGS. 1, 3A, 15 and 16, the third nonwoven component layer 236' may be positioned most proximal to the central longitudinal axis 59, the first nonwoven component layer 225' may be positioned most distal from the central longitudinal axis 59, and the second nonwoven component layer 232' may be disposed intermediate the third nonwoven component layer 236' and the fourth nonwoven component layer 228'. FIG. 3A comprises an exploded portion of the web 212' which illustrates this configuration. In certain other embodiments, the fourth nonwoven component layer 228' may be disposed intermediate the third nonwoven component layer 236' and the second nonwoven component layer 232', for example. It is possible to determine where the second nonwoven component layer 232' and/or the fourth nonwoven component layer 228' are positioned within a web using an SEM. In general, low surface tension fluid strikethrough times appear to improve by 10% to 15%, for example, when the second nonwoven component layer 232' is positioned closer to the skin of the wearer (i.e., closer to the central longitudinal axis 59 of the absorbent article 10). This is referred to as "sidedness."

In one embodiment, by positioning the second nonwoven component layer 232' closer to the central longitudinal axis 59 than the fourth nonwoven component layer 228', the second nonwoven component layer 232' is positioned closer to the skin of the wearer when the absorbent article 10 is positioned about the lower torso of the wearer. Without intending to be bound by any particular theory, applicants believe that the SMNS web exhibits more desirable properties and/or characteristics (e.g., low surface tension fluid strikethrough time) when the second nonwoven component layer 232' is positioned closer to the skin of the wearer and the source of the fluid insult into the absorbent article (and prior to use, closer to the central longitudinal axis 59) than the fourth nonwoven component layer 228'. The arrow 213 of FIG. 3A illustrates the direction of flow of a body exudates or fluid relative to the positioning of the various nonwoven component layers.

In one embodiment, a web of material, such as the SMNS web 212', may have the same or similar properties as the properties as that described above with regard to an SNS web 212. For example, the SMNS web 212' may have a total basis weight of less than 30 gsm, alternatively, less than 15 gsm, alternatively, e.g., 13 gsm, alternatively, less than 10 gsm, and alternatively, in the range of 7 gsm to 15 gsm. In such an embodiment, the web of material may not comprise a film and may have an air permeability of at least 1 m³/m²/min, alternatively, at least 10 m³/m²/min, alternatively, at least 20 m³/m²/min, and alternatively, at least 40 m³/m²/min but less than 100 m³/m²/min. In one embodiment, the web of material may have a local basis weight variation of less than 10%, alternatively, less than 8%, and alternatively, less than 6% and a 32 mN/m low surface tension fluid strikethrough time of at least 19 seconds, alternatively, at least 23 seconds, alternatively, at least 30 seconds, alternatively, at least 35 seconds, alternatively, at least 40 seconds, alternatively, at least 45 seconds, and alternatively, at least 50 seconds.

In one embodiment, the webs described herein, such as the SNS web and/or the SMNS web, for example, may exhibit the specified properties even without comprising a hydrophobic material, such as a hydrophobic melt additive or a hydrophobic surface coating, for example. Such features provide the webs of the present disclosure significant cost-saving advantages over related webs as adding hydrophobic materials leads to additional manufacturing cost and complexity. The inclusion of the N-fiber layer within the webs allows the webs to maintain a desirable low surface tension fluid strikethrough time and air permeability without any hydrophobic materials or films. Without intending to be bound by any particular theory, applicants believe that the N-fiber layer reduces the pore size of the webs by filing in voids within the spunbond and meltblown layers. By creating webs with smaller pore sizes when compared to the pore sizes of related webs, the webs of the present disclosure may have higher capillary drag forces to fluid penetration and, thereby, a longer low surface tension fluid strikethrough time, even without comprising a hydrophobic material or a film. Still, when looking at the structure of the SNS or the SMNS webs, the efficacy of the N-fiber layer in boosting the barrier performance of the web was not expected.

As referenced above, some absorbent articles comprise hydrophilic surfactants or materials on topsheets and/or central portions thereof, for example, and also may comprise hydrophobic materials on barrier cuffs thereof. The hydrophilic surfactants or materials may be used to draw bodily fluids toward an absorbent core of an absorbent article, while the hydrophobic materials restrict the flow of bodily fluids through the barrier cuffs. In some instances, the hydrophilic surfactants or materials may naturally migrate toward other materials prior to use of the absorbent articles. When the hydrophilic surfactants or materials come into contact with the barrier cuffs formed of webs of materials, they reduce the web's ability to hinder low surface tension bodily fluid flow through the barrier cuffs. However, the applicants have found that the webs provided herein, such as the SNS web and/or the SMNS web, for example, may reduce the degradation of barrier properties of the web after hydrophilic surfactant's or material's migration from the topsheet or other central portion of an absorbent article to the barrier cuffs, owing perhaps to the fact that the webs of the present disclosure have higher surface areas and dilute the migrating hydrophilic surfactants when used as the barrier cuffs, or used as a portion of the barrier cuffs. In that, in one embodiment, no hydrophobic material may be present on the barrier cuffs, the hydrophilic surfactants or materials may not spread out fully on the barrier cuffs and, therefore, may not reduce the barrier cuff's ability to restrict the flow of low surface tension bodily fluids therethrough.

Mechanical Bonding

During construction of an absorbent article, such as absorbent article 10, for example, a web, such as an SNS web and/or an SMNS web, for example, may need to be attached to another component of the absorbent article 10. In some embodiments, as described in more detail below, a first portion of the web may be mechanically bonded to a second portion of the web, thereby creating a hem, for example. The components of the absorbent article sought to be mechanically bonded may be passed through a mechanical bonding apparatus.

FIG. 19 illustrates a simplified dynamic mechanical bonding apparatus 320 in accordance with one non-limiting embodiment of the present disclosure. The mechanically bonding apparatus 320 may comprise a patterned cylinder 322, an anvil cylinder 324, an actuating system 326 for adjustably biasing cylinders 322 and 324 towards each other with a predetermined pressure within a predetermined range of pressures, and drivers 328 and 329 for rotating the cylinders 322 and 324, respectively, at independently controlled velocities to provide an optional predetermined surface velocity differential therebetween. In one embodiment, the cylinders 322 and 324 may be biased towards each other at approximately 10,000 psi, for example.

A web 341, a web 342, and a laminate 345 are also shown in FIG. 19. In various embodiments, the web 341 may be various webs of nonwoven material, such as a 13 gsm polypropylene SNS web and/or SMNS web, for example, and the web 342 may be, for example, a 12 gsm, 1.5 denier polypropylene spunbond topsheet, or other component of an absorbent article. Additionally, the apparatus 320 may comprise a frame, not shown, and drivers, not shown, for driving rolls 331 through 338 for controllably forwarding the web 341 and the web 342 through the nip 343 defined between the patterned cylinder 322 and the anvil cylinder 324, and for enabling forwarding the resulting laminate (laminate 345) to a downstream apparatus, such as a roll winder or web converting apparatus: for example, a disposable diaper converter. As used herein, "laminate" refers to at least two components of an absorbent article sharing at least one mechanical bond. Generally, the driving rolls 331 through 338, inclusive, may be provided for guiding and advancing the webs or the web 341 and the web 342, and the laminate 345 through and away from nip the 343. These rolls 331 through 338 may be driven at surface velocities which maintain predetermined levels of tension or stretch so that neither slack web conditions nor excessively tensioned/stretched webs and/or laminate precipitate undesirable deleterious consequences.

For the purposes of clarity, neither the upstream ends or sources of the web 341 and the web 342, nor the downstream destination or user of the laminate 345 are shown. In some embodiments, the mechanically bonding apparatus 320 may received more than two laminates for bonding, and the laminates to be mechanically bonded may comprise, for example, thermoplastic films, nonwoven materials, woven materials, and other webs in roll form; and to provide upstream unwinding and splicing devices to enable forwarding continuous lengths of such laminate through the mechanical bonding apparatus 320 and/or other converters to make products comprising laminated and/or other web elements at controlled velocities and under controlled tension. Furthermore, for simplicity and clarity, the mechanical bonding apparatus 320 is described herein as comprising the cylinders 322 and 324. However, the cylinders 322 and 324 are but one embodiment of nip defining members as stated. Accordingly, it is not intended to thereby limit the present disclosure to an apparatuses comprising cylinders. Similarly, the use of the term "pattern element" is not intended to limit the present disclosure to bonding patterns comprising only discrete, spaced pattern elements to the exclusion of other patterns: e.g., reticulated patterns or patterns comprising continuous or elongate lines of bonding.

In one embodiment, the actuating system 326 for biasing the patterned cylinder 322 towards the anvil cylinder 324 may comprise a pressure regulator 355, and a pneumatic actuator 356, for example. The pressure regulator 355 may be adapted to have its inlet connected to a supply source "P" of pressurized air, and to have its outlet connected to the pneumatic actuator 356 in order to adjust and control the pneumatic actuator means loading of the cylinders 322 and 324 towards each other. Although only one pneumatic actuator 356 is illustrated in FIG. 19, additional actuators may connected to each end journal of the patterned cylinder 322; and each end journal may be supported by frame members and ancillary hardware (not shown) to be vertically moveable so that, in fact, the pressure biasing mechanism may be effective.

In one embodiment, the drivers 328 and 329, are provided to independently drive the cylinders 322 and 324, respectively. Thus, they may rotate the cylinders 322 and 324 so that there is a predetermined but adjustable relationship between the surface velocities of the cylinders 322 and 324. In various embodiments, the rotation may be synchronous, or asynchronous: equal surface velocities; or with a predetermined surface velocity differential with either of the cylinders 322 and 324 being driven faster than the other. In one embodiment that is integrated into a disposable diaper converter, the patterned cylinder 322 is driven by a converter line drive through a gear train so that its surface velocity is essentially matched to the line velocity of the converter; and, the anvil cylinder 324 is powered by an independently speed controlled DC (direct current) drive. This implementation may enable adjustment of the surface velocity of the anvil cylinder 324 to be equal to, or less than, or greater than the surface velocity of the patterned cylinder 322 by predetermined amounts or percentages.

Figure 20:
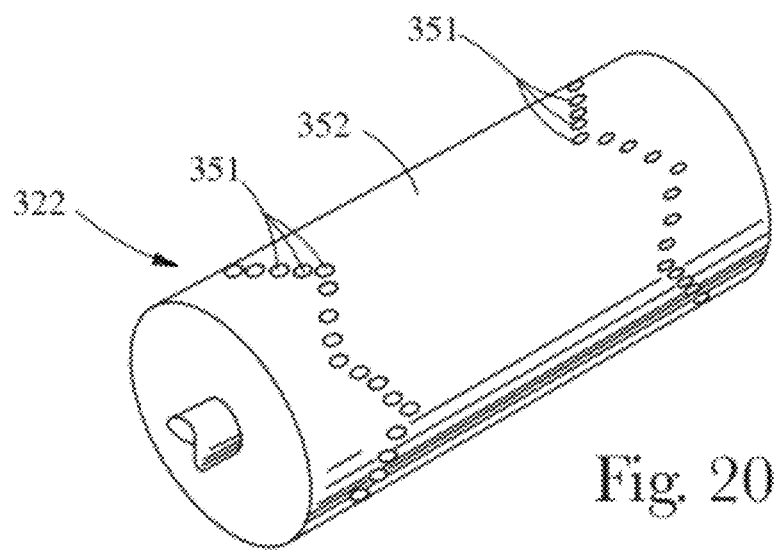
FIG. 20 illustrates a patterned cylinder in accordance with one non-limiting embodiment of the present disclosure.

Referring now to FIG. 20, the patterned cylinder 322 may be configured to have a cylindrical surface 352, and a plurality of pins, nubs, or other protuberances, collectively referred to as pattern of elements 351, which extend outwardly from the surface 352. As shown in FIG. 20, the patterned cylinder 322 may have a saw-tooth shape pattern of elements 351, which may extend circumferentially about each end of the patterned cylinder 322. Such a patterned cylinder 322 may be configured, for example, to laminate, lap-seam, or otherwise mechanically bond together the laminate 341 and the laminate 342. In one embodiment, the patterned cylinder 322 may be comprised of steel and may have a diameter of 11.4 inches (about 29 cm.), for example. While the illustrated embodiment shows two sets of pattern of elements 351 extending circumferentially around the patterned cylinder 322, in other embodiments, the patterned cylinder 322 may have more or less patterns of elements 351 and the overall width of the patterned cylinder 322 may vary accordingly. The anvil cylinder 324 (FIG. 19) may be smooth surfaced, right circular cylinder of steel. In one embodiment, the anvil cylinder 324 may have a 4.5 inch (about 11.4 cm.) diameter and may be independently power rotated by a speed controlled direct current motor, for example, although the embodiments are not limited to such configurations.

Figure 21:
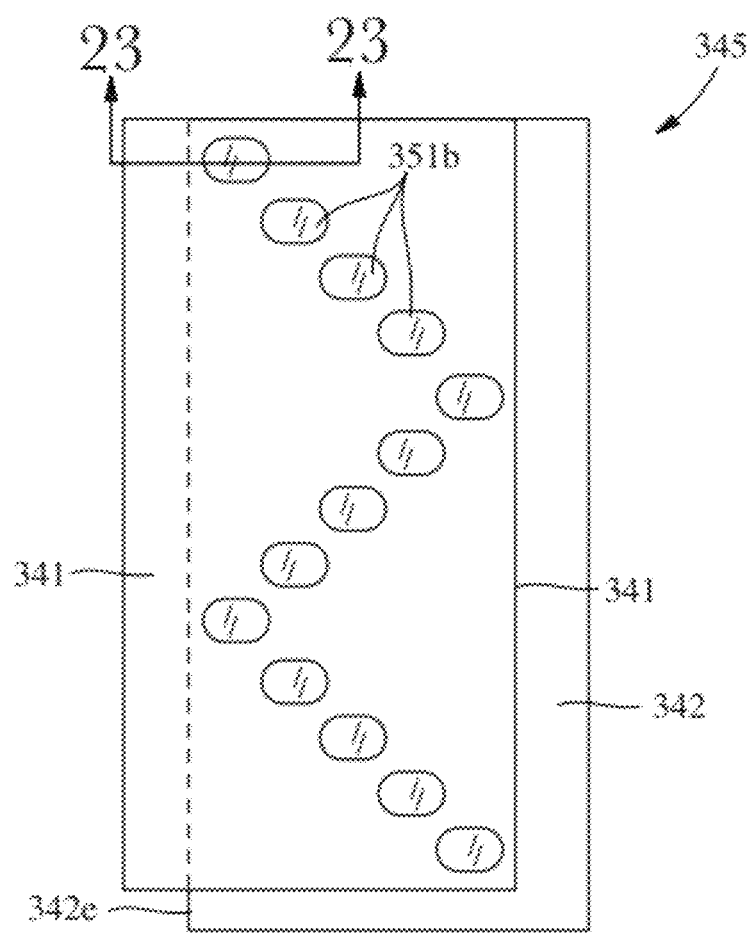
FIG. 21 is a plan view of a fragmentary portion of a bonded web of material in accordance with one non-limiting embodiment of the present disclosure.

FIG. 21 is a plan view of a fragmentary portion of the laminate 345 of FIG. 20 comprising overlapping edge portions of the laminate 341 and the laminate 342 which have been mechanically bonded together by a pattern of bond sites 351b: the pattern being the pattern of pattern elements which extends circumferentially about one end of patterned cylinder 322 (FIG. 20). The bond sites 351b (e.g., bond points, bond areas, dimples, nubs, land areas, cells, or elements) on the laminate 345 may have any suitable geometric shape (e.g., triangle, square, rectangle, diamond, other polygonal shapes, circle, ellipse, oval, oblong, and/or any combinations thereof). The shape and size of the bond pattern may be selected to yield bond sites 351b having predetermined strength and elasticity characteristics in the MD and CD directions, generally referred to in the art as tensile and elongation physical properties. The bond sites' 351b arrangement may be hexagonal, rectangular, square, or any other suitable polygonal shapes, for example. Generally, compressed fibers at the bond sites 351b give strength and reinforcement to the laminate 345, such a barrier cuff nonwoven web comprising an SNS web and/or SMNS web bonded to a spunbond topsheet of an absorbent article, for example. For clarity, the MD oriented edges of the laminate 341 and the laminate 342 are designated as 341e and 342e, respectively, in FIG. 21.

As is to be appreciated, the pattern of elements 351 on the patterned cylinder 322 may be configured to generate a variety of bond site patterns. FIGS. 22A-D illustrate patterns of bond sites in accordance with various non-limiting embodiments. In certain embodiments, the arrangement of the bond sites 351b may be staggered to reduce or eliminate the stress concentration of a "straight" line in the MD. The width (illustrated as "W") of the pattern may vary. For example, in certain embodiments the width may be less than 10 mm, alternatively, less than 5 mm, alternatively, less than 4 mm, and, alternatively, less than 3 mm. Some patterns, for example, may comprise bond sites 351b having different shapes and/or cross sectional areas. In one embodiment, individual bond sites 351b may be 2 mm long and 1 mm wide, and, in one embodiment, individual bond sites 351b may be 4 mm long and 1 mm wide, although other bond site sizing may be used in other embodiments. Furthermore, the area of individual bond sites 351b may vary. In one embodiment the bond area may be 4 $mm^2$, alternatively, alternatively, 2 $mm^2$, and, alternatively, 1.5 $mm^2$ or less. The bond density per square cm may vary based on the particular application. For example, in one embodiment, there may be 15 bonds per $cm^2$, alternatively, 10 bonds per $cm^2$, and, alternatively, less than 10 bonds per $cm^2$. Based on the bond density, the relative bond area (which is the bond density multiplied by the bond area per pin) may be 50% or less in some embodiments and, alternatively, may be 30% or less in other embodiments.

As the nonwoven web, such as the SNS web and the SMNS web, for example, is compressed during the mechanical bonding process, without intending to be bound by any particular theory, it is believed that the rapid compression of the materials beneath the protuberances 351 causes the respective materials to be rapidly deformed and at least partially expressed from beneath the pattern of elements 351. As a result, structures of entangled or otherwise combined material are formed beneath and/or around the protuberances to create mechanical bonds in the nonwoven web. In various embodiments, the mechanical bonds may be created without the use of adhesives, heat sources for a thermal welding process, or an ultrasonic wave source.

Figure 23:
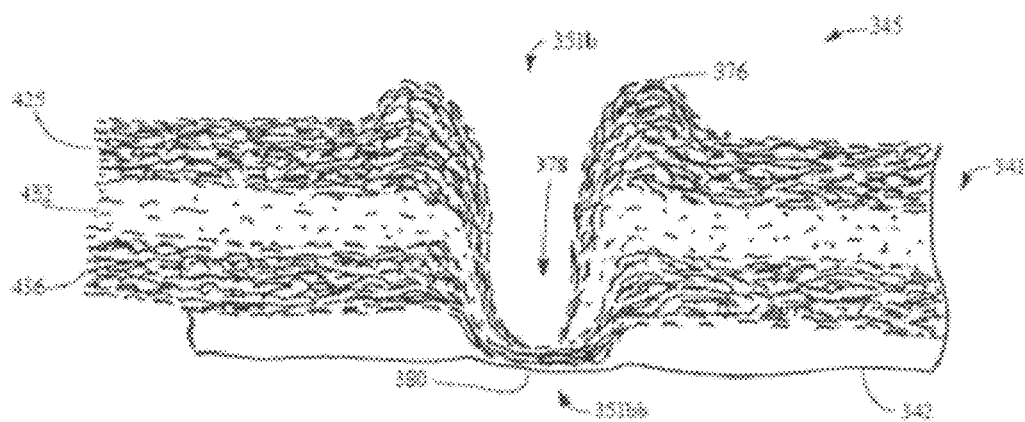
FIG. 23 is a cross-sectional view taken along line 19-19 of FIG. 21, which illustratively shows a bond site in accordance with one non-limiting embodiment of the present disclosure.

FIG. 23 is a sectional view taken along line 19-19 of FIG. 21, which illustratively shows a bond site 351b which mechanically bonds the web 341 and the web 342 together to form the laminate 345. In the illustrated embodiment, the web 341 may be an SNS web material, with an N-fiber layer 432 positioned intermediate a first nonwoven component layer 425 and a second nonwoven component layer 436. The web 342 may comprise any suitable materials, such as a topsheet of an absorbent article, a spunbond or another SNS web, or a second portion of the web 341, for example. In some embodiments, one or both of the web 341 and the web 342 may comprise an SMNS web, comprising both a meltblown layer and a N-fiber layer, in addition to two spunbond layers. In some embodiments, at least one of the webs 341, 342 may comprise a polypropylene component. In one embodiment, if an SMNS web is passing through the mechanical bonding apparatus 320 (FIG. 19), the material may be oriented such that the nubs (or pins) exert force on the N-fiber layer before exerting force on the meltblown layer. This configuration may lead to a displacement and more uniform expression of the N fibers into the underlying and surrounding fibrous structure, with a resulting higher bond strength than when the M layer (or generally coarser fiber layer) are more proximate to the nubs.

As shown in FIG. 23, the bond site 351b may have a bottom surface 351bb and a ring 376 formed substantially around the periphery of the bond side 351b, defined as the grommet ring. The grommet ring 376 may extend above the first nonwoven component layer 425 to form a ridge-like structure generally surrounding each bond site 351b. Without intending to be bound by any particular theory, it is believed that that compression forces applied to the laminate 341 and the laminate 342 during the mechanical bonding process cause material flow (e.g., fiber flow) from a bond center 378 toward the bond's periphery thereby forming the grommet ring 376. In some embodiments, the thickness of the bond site 351b at the bond center 378 may be less than 50 micrometers and, alternatively, less than 15 micrometers. Despite the formation of a robust bond using the aforementioned techniques, the bond site 351b may and should still maintain a material barrier 380 across the entire bottom surface 351bb. If the material barrier 380 across the bottom surface 351bb is breached, the laminate 345 may undesirably leak through the breach when a fluid is introduced to the bond site 351b.

Compared to the bond site 351b, in a thermal bond or a calender bond most of the adhesive force comes from fusion of materials in the bond center, and formation of a grommet ring is may not occur. In fact, the average mass of material per unit area (i.e., basis weight) inside of a thermal bond point is generally the same as in the unbonded surrounding area. In contrast, the grommet ring 376, for example, is postulated to provide most of the bond strength for the mechanical bond, and the bond center 378 has a significantly reduced basis weight compared to the surrounding area. Furthermore, the use of the N-fiber layer(s) in the nonwoven webs helps to provide a significant increase in the uniformity. In some embodiments, the local basis weight variation may be less than 15%, alternatively, less than 10%, and, alternatively, in the range of 5% to 10%.

Without intending to be bound by any particular theory, with regard to performance during the mechanical bonding process, applicants believe that the N-fibers (with diameters less than 1 micron) in the nonwoven web significantly increase the surface area of the web by 4 to 5 times (inversely proportional to the diameters of the fibers that are produced) compared to SMS or spunbond nonwoven webs of same basis weight. The increase in surface area may serve to increase the number of fibers underneath the pattern of elements during the mechanical bonding process to better distribute the energy from the pattern of elements and distribute it throughout the web. Additionally, the use of the N-fibers may allow the web to be covered more densely to create a more uniform web having a relatively low basis weight variation (e.g., less than 10% local basis weight variation). As a result, the materials incorporating the N-fibers display less defects within the bond sites. In some embodiments, mechanically bonded webs comprising at least one N-fiber layer may have a defect occurrence rate of less than 0.9%, alternatively less than 0.54% and, alternatively, less than 0.25%. with the bonded nonwoven web having a basis weight (combined basis weight of two webs or more) of less than 25 gsm. Furthermore, in accordance with the embodiments of the present disclosure, webs incorporating the N-fiber layer, such as SNS webs and SMNS webs, for example, may utilize generally small bond areas as compared to other webs, such as SMS webs. Moreover, the desired performance of the webs may be achieved with lower basis weights and/or lower stock heights when the N-fiber layer is used. In some embodiments, the bonded nonwoven material may have a low basis weight (e.g., less than 25 gsm or less than 15 gsm) and achieve mechanical bonds with suitable defect occurrence rates.

Figure 24:
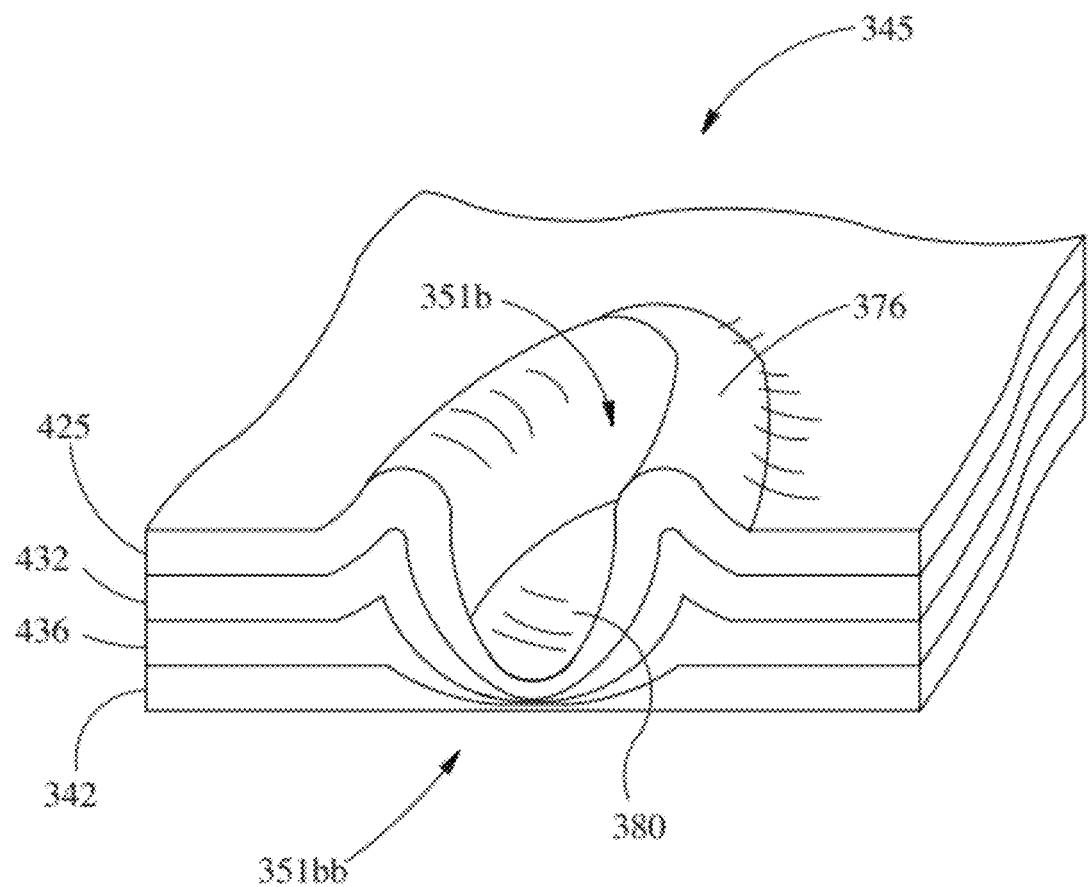
FIG. 24 is a cross-sectional perspective view of the bond site of FIG. 23.

FIG. 24 is a sectional perspective view of the bond site 351b shown in FIG. 23. As illustrated, the grommet ring 376 extends generally around the periphery of the bond site 351b. Additionally, the material barrier 380, such as a membrane, extends across the bond site 351b in order to substantially "seal" the bond to maintain the bond's fluid barrier characteristics.

Utilizing the aforementioned mechanical bonding techniques, a barrier cuff, for example, may be attached to, or otherwise integrated with, an absorbent article. Referring to FIGS. 1, 2, 3A-3B and 5, the absorbent article 10 may comprise a pair of longitudinal barrier cuffs 51, attached to a chassis 47. The chassis 47 may be any component or portion, or collection of components or portions, of the absorbent article 10, such as the topsheet 20, for example. Each longitudinal barrier cuff 51 may be comprised of a web 65, such as an SNS web or an SMNS web, having the characteristics described above. For example, the web 65 may comprise a first nonwoven component layer 125 comprising fibers having an average diameter in the range of 8 microns to 30 microns and a second nonwoven component layer 132 comprising fibers having an average diameter of less than 1 micron. The web of material 65 of the longitudinal barrier cuffs 51 may have a local basis weight variation less than 10%, alternatively, less than 8%, or alternatively, less than 6%. In fact, applicants estimated that a low defect rate of less than 10 bond defects per 5 m of a 25 gsm laminate (bond occurrence rate less than 0.35%) would require an SMS web to have an even lower local basis weight variation of 3% or less. In one embodiment, an SNS or SMNS web of 13 gsm (comprising an N and M layer of 1 gsm each) or less, when combined with a spunbond layer of 12 gsm or less is sufficient to require a local basis weight variation of 6% or less in order to achieve a defect rate of less than 10 bond defects per 5 m of laminate (bond occurrence rate less than 0.35%). The variation of 10% would suffice for an SNS or SMNS web of 13 to 15 gsm with the N layer of 1.5 gsm to 3 gsm, or combining two layers of SNS or SMNS webs of 12 gsm to 13 gsm each. Each of the longitudinal barrier cuffs 51 may comprise a longitudinal zone of attachment 49 where the longitudinal barrier cuff 51 attaches to the chassis 47. In some embodiments, the longitudinal zone of attachment 49 may extend generally parallel to the central longitudinal axis 59 (FIG. 1). In some embodiments, the zone of attachment 49 may be generally linear or may be curved, or a combination. Furthermore, the zone of attachment 49 may be substantially continuous along the absorbent article or, alternatively, discontinuous. Furthermore, each longitudinal barrier cuffs 51 may have a longitudinal free edge 64 and a plurality of mechanical bonds 68 disposed between the zone of attachment 49 and the free edge 64. In one embodiment, the plurality of mechanical bonds 68 forms a hem proximate to the longitudinal free edge 64. For example, the plurality of mechanical bonds 68 may attach, for example, a first portion of the web material 59 to a second portion 61 of the web 65, which may be referred to as a hem fold bond. In some embodiments, the mechanical bonds 68 may attach the web 65 to a portion of the absorbent article 10. The mechanical bonds 68 may be similar to the bond site 351b illustrated in FIGS. 23-24, for example. The mechanical bonds 68 may, for example, bond the topsheet 20 to the longitudinal barrier cuffs 51. Furthermore, the mechanical bonds 68 may be disposed in any suitable pattern or configuration, such as the patterns illustrated in FIGS. 22A-22D, for example.

In another embodiment, referring to FIG. 3B, longitudinal barrier cuffs 51 of the absorbent article 10 may each comprises a first layer of the web of material 65a and a second layer of the web of material 65b. The first and second layers of web material 65a and 65b, may each comprise an SNS web or an SMNS web, for example. Furthermore, as illustrated, the longitudinal barrier cuff 51 may be folded in order to form to two layers of web material 65a and 65b. In other embodiments, two separate webs of material 65a and 65b may be joined, bonded, or otherwise attached to form the longitudinal barrier cuff 51. The longitudinal barrier cuffs 51 may comprise a longitudinal zone of attachment 49 where the longitudinal barrier cuff attaches to the chassis 47 and a longitudinal free edge 64. A plurality of mechanical bonds 68 may attach the first and second layers of the web of material 65a and 65b. In some embodiments, the plurality of mechanical bonds 68 attach at least on of the first and second layers of the web of material 65a and 65b to the chassis 47. In one embodiment, the plurality of mechanical bonds 68 have a defect occurrence rate of less than 0.9%, alternatively, less than 0.5% and, alternatively, less than 0.25%. In some embodiments, the plurality of mechanical bonds 68 may be disposed along, or generally proximate to, the longitudinal zone of attachment 49.

In one embodiment, the SNS web and/or the SMNS web may comprise, or may comprise a portion of, a component of an absorbent article other than a longitudinal barrier cuff, such as a backsheet of a diaper, for example, owing to the webs' superior properties of air permeability, low surface tension fluid strikethrough time, basis weight, and local basis weight variation. Likewise, the SNS web and/or the SMNS web may also be used to comprise any other suitable portions of various consumer absorbent articles or other suitable non-absorbent articles or portions thereof. Some non-limiting examples of non-absorbent articles that may be formed of, or formed partially of, the SNS web and/or the SMNS web are consumer disposable water filtration components, air freshener components using perfume release for odor elimination, and surfactant release components in detergents and detergent capsules.

In other embodiments, the SNS web and/or the SMNS web may be formed with, attached to, and/or used with a film, such as microporous or micro-apertured films (or films with risk of pin holes), for example, to increase the low surface tension fluid strikethrough times of the webs for desired applications, such as when used as a backsheet of a diaper, for example. In still other embodiments, the SNS web and/or the SMNS web may comprise or be coated with a hydrophobic melt additive and/or a hydrophobic surface coating to again increase the low surface tension fluid strikethrough times of the webs for desired applications. In one embodiment, the SNS web and/or the SMNS web may comprise both a film and a hydrophobic melt additive and/or a hydrophobic surface coating, for example. Such web embodiments with the film, the hydrophobic melt additive, and/or the hydrophobic surface coating may comprise or may be used as components of any suitable absorbent or non-absorbent articles, such as diaper backsheets, catamenial pad topsheets or backsheets, for example.

Test Methods

Air Permeability Test

The air permeability is determined by measuring the flow rate of standard conditioned air through a test specimen driven by a specified pressure drop. This test is particularly suited to materials having relatively high permeability to gases, such as nonwovens, apertured films and the like.

A TexTest FX3300 instrument or equivalent is used. (Available by Textest AG in Switzerland (www.textest.ch), or from Advanced Testing Instruments ATI in Spartanburg S.C., USA.) The Test Method conforms to ASTM D737. The test is operated in a laboratory environment at 23±2° C. and 50±5% relative humidity. In this test, the instrument creates a constant differential pressure across the specimen which forces air through the specimen. The rate of air flow through the specimen is measured in $m^3/m^2/min$, which is actually a velocity in m/min, and recorded to three significant digits. The test pressure drop is set to 125 Pascal and the 5 $cm^2$ area test head is used. After getting the system operational, the 1 $cm^2$ insert is installed (also available from Textest or from ATI). The sample of interest is prepared and specimens cut out to fit into the 1 $cm^2$ head insert. After making the measurement of a specimen according to operating procedure, the result is recorded to three significant digits accounting for the area difference between the 1 $cm^2$ test area insert and the 5 $cm^2$ head. If the FX3300 instrument is not accounting for this automatically, then each specimen's result is manually recalculated to reflect the actual air permeability by accounting for the area difference between the 1 $cm^2$ test area insert and the 5 $cm^2$ head. The average of 10 specimens' air permeability data of this sample is calculated and reported.

Surface Tension of a Liquid

The surface tension of a liquid is determined by measuring the force exerted on a platinum Wilhelmy plate at the air-liquid interface. A Kruss tensionmeter K11 or equivalent is used. (Available by Kruss USA (www.kruss.de)). The test is operated in a laboratory environment at 23±2° C. and 50±5% relative humidity. The test liquid is placed into the container given by the manufacturer and the surface tension is recorded by the instrument and its software.

Surface Tension of a Fiber

Basis Weight Test

A 9.00 cm2 large piece of web, i.e. 1.0 cm wide by 9.0 cm long, is cut out of the product, and it needs to be dry and free from other materials like glue or dust. Samples are conditioned at 23° Celsius (±2° C.) and at a relative humidity of about 50% (±5%) for 2 hours to reach equilibrium. The weight of the cut web pieces is measured on a scale with accuracy to 0.0001 g. The resulting mass is divided by the specimen area to give a result in $g/m^2$ (gsm). Repeat for at least 20 specimens for a particular sample from 20 identical products, If the product and component is large enough, more than one specimen can be obtained from each product. An example of a sample is the left diaper cuff in a bag of diapers, and 10 identical diapers are used to cut out two 9.00 $cm^2$ large specimens of cuff web from the left side of each diaper for a total of 20 specimens of "left-side cuff nonwoven." If the local basis weight variation test is done, those same samples and data are used for calculating and reporting the average basis weight.

Mechanical Bond Defect Occurrence Rate Test

Figure 25A:
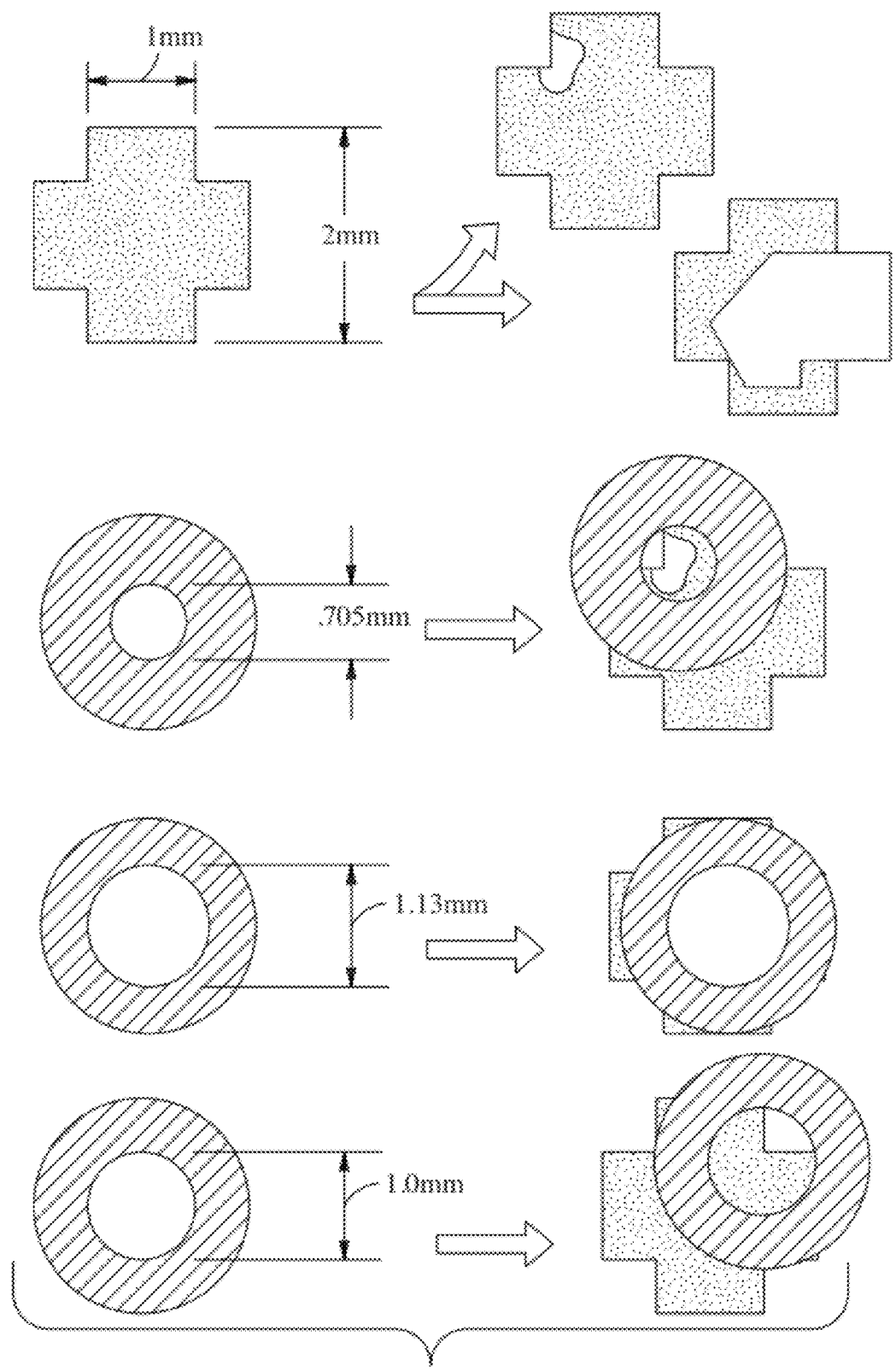
FIG. 25A illustrates mechanical bond quality and the templates for determining defects.
Figure 25B:
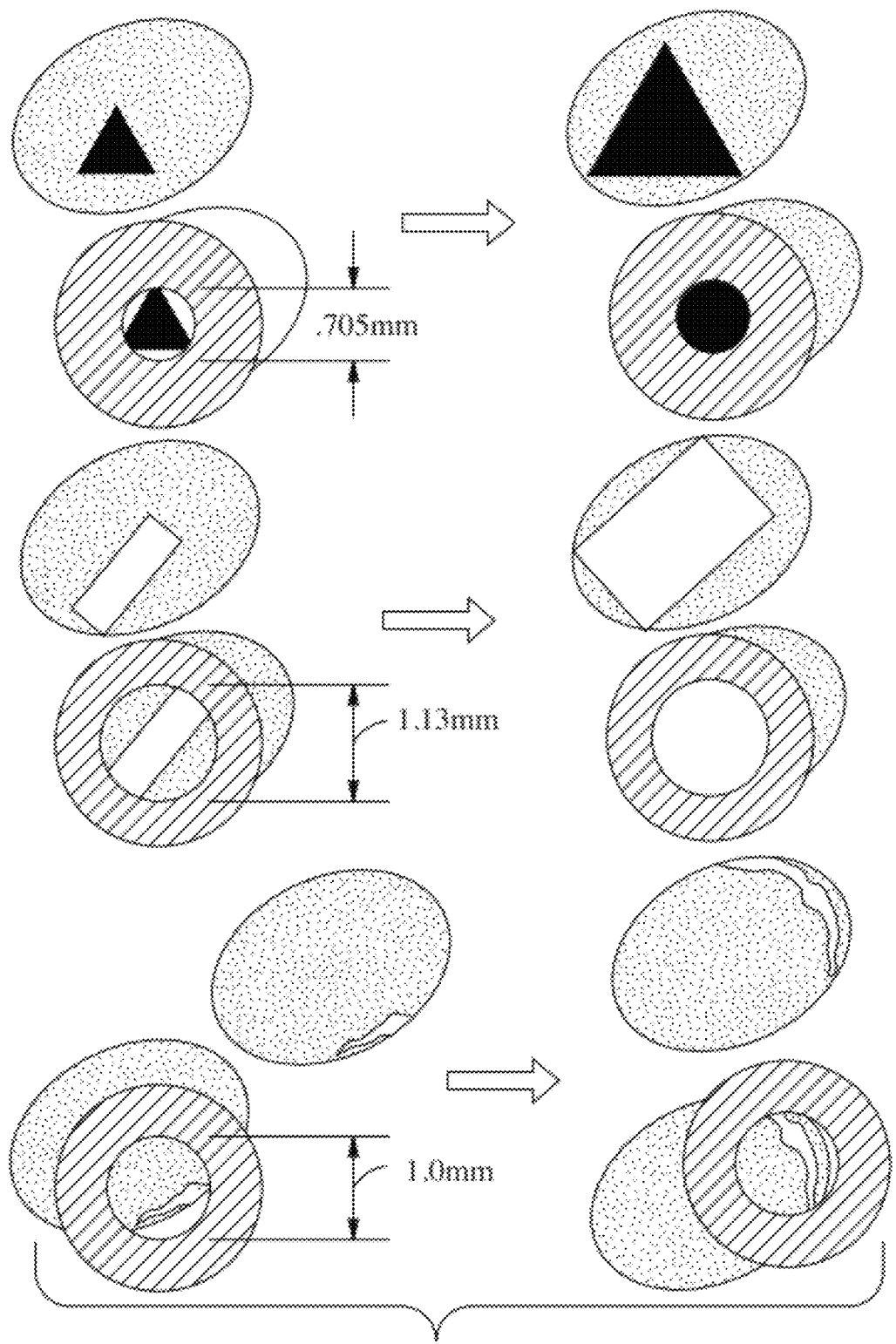
FIG. 25B illustrates the use of defect area templates for defects of holes, skips and tears.

The defect occurrence rate of a mechanical bonding pattern is determined by. determining the percentage of defective bonds in 5.0 meters of bonded material. Defects are holes or skips or tears. Holes are defined as an area of at least 0.39 $mm^2$ that is apertured or missing from the film-like membrane formed at the bond site material Skips are defined as an area of at least 1.00 $mm^2$ where the intended mechanical bond site does not visually show a film-like membrane. The third type of defect, a tear, is the result of a broken perimeter of the membrane where at least 1.0 mm of the membrane's perimeter is torn or broken. See FIG. 24 for illustration of an example material barrier 380 (or "membrane") within a mechanical bond grommet. FIG. 25 illustrates what constitutes a good mechanical bond, a bad, but not defective mechanical bond, and a defective mechanical bond during a Mechanical Bond Defect Occurrence Rate Test.

A visual procedure is used to measure the defect occurrence rate from a produced web of two or more webs, or from a web that is cut out of a product or product feature. First, take 5 m of the nonwoven web or equivalent number of products (e.g., 10 consecutive diapers of 0.5 m pad cuff length) and inspect one side (e.g., the left longitudinal side or the right longitudinal side of the diaper of the bond sites on the nonwoven webs for defects. Care is taken not to disrupt and damage the bonds and to select the section where the mechanical bonds have not been overbonded with a mechanical bond a second time or more.

If the component with the bonds of interest cannot be removed by simply cutting without disrupting and damaging the bonds, another method for disintegration may be used, such as use of a THF bath to dissolve the adhesives. After carefully cutting out the component with the bonds of interest, label the specimens for tracking and later analysis.

Figure 22A:
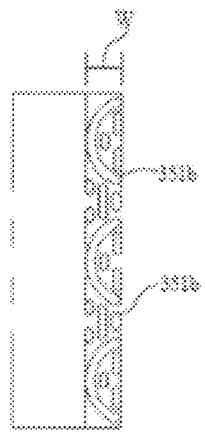
FIG. 22A-D illustrate patterns of bond sites in accordance with various non-limiting embodiments of the present disclosure.
Figure 22B:
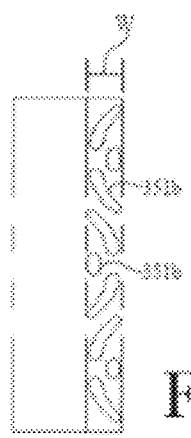
Figure 22C:
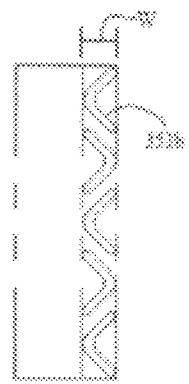
Figure 22D:
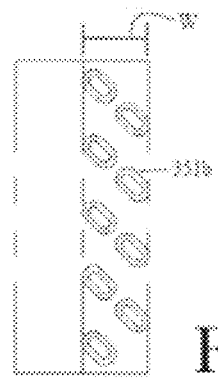

Each mechanical bond pattern has a certain repeat length. The total target number of bonds in the 5 m laminate web is obtained by multiplying the 5 m length (5000 mm) with the number of bonds per repeat length (#bonds/mm). If the mechanical bonds of the bond pattern of interest are so large as to extend the whole diaper length, the diaper length is defined as repeat length. Cut out an extra (per example 18$^{th}$) section according to above from the sample of interest, tape its ends to a flat surface so the section is fully extended (manually extended to full length with reasonable force without damaging the web and to remove winkles and extend any elastomeric contraction) then slide a thin black piece of cardboard under the taped sample. Find a repeat length of the bond pattern over at least a 100 mm section, which means for repeat lengths less than 100 mm long, that multiple individual repeat lengths are selected. For example the bond pattern of FIG. 22A, when measuring the length from the top to the bottom of the shown pattern and it gives 200 mm, then the repeat length of the pattern in FIG. 22A is from the top edge of the C-shaped bond on the very top, to the top edge of the third C-shaped bond from the top, and in this example would give 142 mm. All the bonds, even if of multiple shapes, are counted and added up in this overall repeat length. In the example of 22A, the overall repeat length is 142 mm, from top of first C-shaped bond to top of third. The number of bonds in this 142 mm repeat length is 16 bonds. The total number of bonds within the 5000 mm length is thus 5000 mm multiplied by 16 bonds divided by 142 mm, which is 563 bonds.

Each bond site is examined under a microscope at 25× magnification. The lens is used in conjunction with a the respective defect determination templates; i.e. for holes template with a 0.39 mm² large circle (0.705+/−0.005 mm diameter), for skips the template with a 1.00 mm² large circle (mm diameter), and for tears the template with a 1.0 mm diameter circle, which can be seen on the specimen when viewed through the eyepiece. See illustration in FIG. 25B, and outlined here further for a hole defect. If the circle can fit within the hole, then the hole is counted as a hole defect. (see FIG. 25B) After one bond site is inspected, the next consecutive bond to be inspected is in the lengthwise direction of the diaper.

Holes are classified as H1, H2, . . . or H5, with the number reflecting the number of consecutive mechanical bonds with a hole. Consecutive defects in the same row in the diaper length direction are counted as a single defect, i.e., five consecutive holes are counted as one H5 defect. Record the results of the analysis in a data table like below, where for each specimen and each image the number of holes and skips is recorded.

the number of consecutive missing mechanical bonds. Consecutive defects in the same row in the diaper length direction are counted as a single defect, i.e., 5 consecutive skips is counted as one S5 defect. Tear failures are classified with the respective template and recorded. as T1, T2 . . . or T5 with the number reflecting the number of consecutive missing mechanical bonds. Consecutive defects in the same row in the diaper length direction are counted as a single defect i.e. five consecutive tears are counted as one T5 defect. The total number of defects of all holes, skips and tears are added up to obtain the number of defects per 5.0 m of web. Dividing this by the theoretical number of mechanical bonds (mechanical bond density in number of mechanical bonds/cm times the length of the laminate (500 cm)) and multiplied by 100% yields the defect occurrence rate in %. The theoretical number includes all mechanical bonds that would be on the 5 m laminate regardless of whether material is properly bonded or not.

See FIGS. 25A, 25B, and 37A to 37G for illustration of identifying the defects with this test.

Fiber Diameter and Denier Test

The diameter of fibers in a sample of a web is determined by using a Scanning Electron Microscope (SEM) and image analysis software. A magnification of 500 to 10,000 times is chosen such that the fibers are suitably enlarged for measurement. The samples are sputtered with gold or a palladium compound to avoid electric charging and vibrations of the fibers in the electron beam. A manual procedure for determining the fiber diameters is used. Using a mouse and a cursor tool, the edge of a randomly selected fiber is sought and then measured across its width (i.e., perpendicular to fiber direction at that point) to the other edge of the fiber. A scaled and calibrated image analysis tool provides the scaling to get actual reading in micrometers (μm). Several fibers are thus randomly selected across the sample of the web using the SEM. At least two specimens from the web (or web inside a product) are cut and tested in this manner. Altogether at least 100 such measurements are made and then all data are recorded for statistic analysis. The recorded data are used to calculate average (mean) of the fiber diameters, standard deviation of the fiber diameters, and median of the fiber diameters. Another useful statistic is the calculation of the amount of the population of fibers that is below a certain upper limit. To determine this statistic, the software is programmed to count how many results of the fiber diameters are below an upper limit and that count (divided by total number of data and multiplied by 100%) is reported in percent as percent below the upper limit, such as percent below 1 micrometer diameter or %-submicron, for example.

If the results are to be reported in denier, then the following calculations are made.

| Image | H1 | H2 | H3 | H4 | H5 | S1 | S2 | S3 | S4 | S5 | T1 | T2 | T3 | T4 | T5 | Defects per specimen |
|---|---|---|---|---|---|---|---|---|---|---|---|---|---|---|---|---|
| Spec 1 - image 1 S1-i2 Etc. | | | | | | | | | | | | | | | | |

If there are more bond shapes not yet analyzed for holes, repeat this step for those and determine the number of its defects like above using this bond shape's hole defect limit.

Skip failures are classified with the respective template and recorded . . . as S1, S2, . . . , or S5, with the number reflecting Fiber Diameter in denier=Cross-sectional area (in m²)*density (in kg/m³)*9000 m*1000 g/kg.

The cross-sectional area is π*diameter²/4. The density for polypropylene, for example, may be taken as 910 kg/m³.

Given the fiber diameter in denier, the physical circular fiber diameter in meters (or micrometers) is calculated from these relationships and vice versa. We denote the measured diameter (in microns) of an individual circular fiber as $d_i$.

In case the fibers have non-circular cross-sections, the measurement of the fiber diameter is determined as and set equal to the hydraulic diameter which is four times the cross-sectional area of the fiber divided by the perimeter of the cross of the fiber (outer perimeter in case of hollow fibers).

Fiber Diameter Calculations

The number-average diameter, alternatively average diameter, $$d_{num} = \frac{\sum_{i=1}^{n} d_i}{n}$$

The mass-average diameter is calculated as follows: mass average diameter, $$d_{mass} = \frac{\sum_{i=1}^{n}(m_i \cdot d_i)}{\sum_{i=1}^{n} m_i} = \frac{\sum_{i=1}^{n}(\rho \cdot V_i \cdot d_i)}{\sum_{i=1}^{n}(\rho \cdot V_i)} = \frac{\sum_{i=1}^{n}\left(\rho \cdot \frac{\pi d_i^2 \cdot \partial x}{4} \cdot d_i\right)}{\sum_{i=1}^{n}\left(\rho \cdot \frac{\pi d_i^2 \cdot \partial x}{4}\right)} = \frac{\sum_{i=1}^{n} d_i^3}{\sum_{i=1}^{n} d_i^2}$$

where
fibers in the sample are assumed to be circular/cylindrical,
$d_i$=measured diameter of the $i^{th}$ fiber in the sample,
$\partial x$=infinitesimal longitudinal section of fiber where its diameter is measured, same for all the fibers in the sample,
$m_i$=mass of the $i^{th}$ fiber in the sample,
n=number of fibers whose diameter is measured in the sample
$\rho$=density of fibers in the sample, same for all the fibers in the sample
$V_i$=volume of the $i^{th}$ fiber in the sample.

The polydispersity of fiber diameter distribution=

$$\frac{\text{(mass average fiber diameter)}}{\text{(number average fiber diameter)}}$$

Low Surface Tension Fluid Strikethrough Time Test

The low surface tension fluid strikethrough time test is used to determine the amount of time it takes a specified quantity of a low surface tension fluid, discharged at a prescribed rate, to fully penetrate a sample of a web (and other comparable barrier materials) which is placed on a reference absorbent pad. As a default, this is also called the 32 mN/m Low Surface Tension Fluid Strikethrough Test because of the surface tension of the test fluid and each test is done on two layers of the nonwoven sample simply laid on top of each other.

For this test, the reference absorbent pad is 5 plies of Ahlstrom grade 989 filter paper (10 cm×10 cm) and the test fluid is a 32 mN/m low surface tension fluid.

Scope

This test is designed to characterize the low surface tension fluid strikethrough performance (in seconds) of webs intended to provide a barrier to low surface tension fluids, such as runny BM, for example.

Equipment

Lister Strikethrough Tester: The instrumentation is like described in EDANA ERT 153.0-02 section 6 with the following exception: the strike-through plate has a star-shaped orifice of 3 slots angled at 60 degrees with the narrow slots having a 10.0 mm length and a 1.2 mm slot width. This equipment is available from Lenzing Instruments (Austria) and from W. Fritz Metzger Corp (USA). The unit needs to be set up such that it does not time out after 100 seconds.

Reference Absorbent Pad: Ahlstrom Grade 989 filter paper, in 10 cm×10 cm areas, is used. The average strikethrough time is 3.3+0.5 seconds for 5 plies of filter paper using the 32 mN/m test fluid and without the web sample. The filter paper may be purchased from Empirical Manufacturing Company, Inc. (EMC) 7616 Reinhold Drive Cincinnati, Ohio 45237.

Test Fluid The 32 mN/m surface tension fluid is prepared with distilled water and 0.42+/−0.001 g/liter Triton-X 100. All fluids are kept at ambient conditions.

Electrode-Rinsing Liquid: 0.9% sodium chloride (CAS 7647-14-5) aqueous solution (9 g NaCl per 1 L of distilled water) is used.

Test Procedure

Ensure that the surface tension is 32 mN/m+/−1 mN/m. Otherwise remake the test fluid.

Prepare the 0.9% NaCl aqueous electrode rinsing liquid.

Ensure that the strikethrough target (3.3+/−0.5 seconds) for the Reference Absorbent Pad is met by testing 5 plies with the 32 mN/m test fluid as follows:

Neatly stack 5 plies of the Reference Absorbent Pad onto the base plate of the strikethrough tester.

Place the strikethrough plate over the 5 plies and ensure that the center of the plate is over the center of the paper. Center this assembly under the dispensing funnel.

Ensure that the upper assembly of the strikethrough tester is lowered to the pre-set stop point.

Ensure that the electrodes are connected to the timer.

Turn the strikethrough tester "on" and zero the timer.

Using the 5 mL fixed volume pipette and tip, dispense 5 mL of the 32 mN/m test fluid into the funnel.

Open the magnetic valve of the funnel (by depressing a button on the unit, for example) to discharge the 5 mL of test fluid. The initial flow of the fluid will complete the electrical circuit and start the timer. The timer will stop when the fluid has penetrated into the Reference Absorbent Pad and fallen below the level of the electrodes in the strikethrough plate.

Record the time indicated on the electronic timer.

Remove the test assembly and discard the used Reference Absorbent Pad. Rinse the electrodes with the 0.9% NaCl aqueous solution to "prime" them for the next test. Dry the depression above the electrodes and the back of the strikethrough plate, as well as wipe off the dispenser exit orifice and the bottom plate or table surface upon which the filter paper is laid.

Repeat this test procedure for a minimum of 3 replicates to ensure the strikethrough target of the Reference Absorbent Pad is met. If the target is not met, the Reference Absorbent Pad may be out of spec and should not be used.

After the Reference Absorbent Pad performance has been verified, nonwoven web samples may be tested.

Cut the required number of nonwoven web specimens. For web sampled off a roll, cut the samples into 10 cm by 10 cm sized square specimens. For web sampled off of a product, cut the samples into 15 by 15 mm square specimens. The fluid flows onto the nonwoven web specimen from the strike through plate. Touch the nonwoven web specimen only at the edge.

Neatly stack 5 plies of the Reference Absorbent Pad onto the base plate of the strikethrough tester.

Place the nonwoven web specimen on top of the 5 plies of filter paper. Two plies of the nonwoven web specimen are used in this test method. If the nonwoven web sample is sided (i.e., has a different layer configuration based on which side is facing in a particular direction), the side facing the wearer (for an absorbent product) faces upwards in the test.

Place the strikethrough plate over the nonwoven web specimen and ensure that the center of the strikethrough plate is over the center of the nonwoven web specimen. Center this assembly under the dispensing funnel.

Ensure that the upper assembly of the strikethrough tester is lowered to the pre-set stop point.

Ensure that the electrodes are connected to the timer. Turn the strikethrough tester "on" and zero the timer.

Run as described above.

Repeat this procedure for the required number of nonwoven web specimens. A minimum of 5 specimens of each different nonwoven web sample is required. The average value is the 32 mN/m low surface tension strikethrough time in seconds.

35 mN/m Low Surface Tension Fluid Strikethrough Test

This test is done as described above with two exceptions. First, the testing is done with one layer of the nonwoven web sample. Second, the test fluid has a surface tension of 35 mN/m. The test fluid is created by mixing 2 parts of the 32 mN/m fluid and 5 parts of deionized water. Before testing, the actual surface tension of the fluid needs to be checked to ensure that it is 35+/−1 mN/m. If this fluid is not 35+/−1 mN/m, it should be discarded and another fluid should be prepared.

Local Basis Weight Variation Test

Purpose

The local basis weight variation test is intended to measure variability of mass distribution of 9 cm² areas throughout a lot of a nonwoven web. The local basis weight variation parameter describes a lack of desirable uniformity through a nonwoven web. Lower local basis weight variation is desirable since it helps in consistency of most other qualities, such as barrier properties, strength, and bonding, for example.

Principle

The mass of 1 cm by 9 cm area nonwoven web samples are measured and analyzed to determine the local basis weight variation (i.e., mass distribution) throughout a lot of a web production. All individual data of the lot, or of a portion of the lot, of interest is analyzed as standard deviation and average and then the quotient is taken to provide the local basis weight variation. Stated another way, this gives a relative standard deviation (RSD) or coefficient of variation (COV) of the small area basis weight distribution.

The size of 1 cm by 9 cm for each replicate was selected such that the mass of each replicate may be measured with sufficient digits and accuracy on the specified scale. Mass is measured in grams.

Grammage and basis weight are synonymous and are measured in g/m² (also written gsm) units.

Samples of the nonwoven web are taken in the machine direction (the web needs to be at least 1 cm wide such that it may be cut into specimens).

Equipment

Scale with a 0.0001 g sensitivity (alternatively, a scale with 0.00001 g sensitivity or with accuracy to within 0.1% of a target basis weight) (e.g., 13 gsm in 1 cm by 9 cm area weighs 0.0117 g; 0.1% of this mass is 0.00001 g)

Die with 1.0 cm by 9.0 cm or 9 cm² area rectangular cut area optionally with soft foam for easier sample removal. The die areas need to be within about 0.05 mm side length.

Hydraulic press: The hydraulic press is used to stamp out the nonwoven web samples with the die.

Test Procedure

Sampling:

At least 40 data points are needed to assess the local basis weight variation of a defined nonwoven web sample. These data points are to be sampled evenly throughout the nonwoven web sample.

Test specimens should be free of wrinkles and free from contaminants such as dust or glue.

Conditioning:

Use only clean and dry nonwoven web samples, at normal lab conditions (50+/−5% relative humidity and 23+/−2 degrees C.).

Procedure:

Cut out the replicate with the prepared die 9 cm² and the hydraulic press. One layer is cut out. Paper may be put between the cutting board and the sample for easier removal after cutting.

Be sure that the scale reads exactly zero (0.0000 g), or tare the scale to 0.0000 g.

Measure the cut out replicate on the scale to the nearest 0.0001 g (alternatively, to the nearest 0.00001 g).

Record the lot, nonwoven web sample, replicate and result.

Continue the above steps for all selected replicates.

When the analysis is done for absorbent articles (e.g., diapers) then identical products are used, preferably consecutive diapers are tested within one bag, package, or case. Either the right of the left leg barrier cuff may be selected for the samples. For purposes of this description, we assume that the right leg barrier cuff has been selected.

Carefully cut the leg barrier cuffs out of the absorbent articles and number the cuffs sequentially (e.g., right leg barrier cuff of absorbent article 1). Proceed with doing the same for the remaining absorbent articles in the bag, package or case.

Beginning with the cut out leg barrier cuff from absorbent article 1, fasten (e.g., tape) the leg barrier cuff to a piece of cardboard or plastic sheeting and put the die with the cut area (1 cm by 9 cm) onto the barrier cuff and cut out a specimen. If there is still enough sample length left, repeat this procedure one or two more times for two or three more specimens out of the barrier cuff.

Weigh the cut out parts to the nearest 0.0001 g and record the result.

Proceed with the other cut out right side leg barrier cuffs from the other absorbent articles and measure the mass of the die cut 1 cm by 9 cm sized pieces and record the data.

Repeat this procedure for as many absorbent articles as needed and, if necessary, several bags of absorbent articles, until the right side barrier cuff of the absorbent articles is characterized with 40 data points. Since a package of absorbent articles typically holds over twenty absorbent articles, it is possible to cut out and measure 40 or more replicates per side (in this case the right side) for each sample package of absorbent articles.

Repeat the whole procedure for the other side of the product (in this case the left side). The local basis weight variation should be calculated for each side.

Calculations
- Calculate the average weight of the nonwoven web sample (40 individual replicates)
- Calculate the standard deviation of the nonwoven web sample
- Calculate the Local Basis Weight Variation (standard deviation/average weight).

Reporting

Report the local basis weight variability to the nearest first decimal point 0.1%, e.g., 7.329% becomes 7.3%.

Surface Tension Measurement of Fluid

The measurement is done with a video-based optical contact angle measuring device, OCA 20, by DataPhysics Instrument GmbH, or equivalent. Choose a clean glass syringe and dosing needle (with 1.65~3.05 mm size) before filling the syringe with liquid to test; and then remove the bubble from the syringe/needle; adjust the position of the syringe, dosing needle and stage; a drop of the test liquid with known volume will be formed at the lower end of the dosing needle. The detection of the drop shape is done by the software SCA20 and the surface tension is calculated according to the Young-Laplace equation. The measurement is carried out on an anti-vibration table in a closed hood.

The surface energy of fibers is also determined with this instrument following the Sessile Drop Technique.

Thickness or Caliper Test

The thickness test is done according to EDANA 30.5-99 normal procedure with a foot of 15 mm diameter pushing down at 500 Pascal (i.e., a force of 0.0884N). Start the test, wait for 5 seconds so the result stabilizes, and record the result in millimeters to the nearest 0.01 mm. The sample analysis should include at least 20 measurements from different locations spread throughout the available sample.

Pore Size Distribution Test

The pore size distribution of nonwoven web samples is measured with the Capillary Flow Porometer, the APP 1500 AEXi from Porous Materials, Inc. or equivalent. The available pressure of the clean and dry air supply should be at least 100 psi so that pores down to 0.08 microns may be detected. A nonwoven web sample is first cut and fully soaked in a low surface tension fluid, namely Galwick with a surface tension of 15.9 mN/m. The nonwoven web sample size is 7 mm diameter. The soaked nonwoven web sample is placed into the sample chamber of the instrument and the chamber is then sealed. Upon starting the automatic measurement cycle, gas flows into the sample chamber behind the nonwoven web sample and then the gas pressure is slowly increased via the computer to a value sufficient to overcome the capillary action of the fluid in the pore having the largest diameter in the nonwoven web sample. This is the bubble point. The pressure inside the chamber is further increased in small increments resulting in a flow of gas that is measured until all of the pores in the nonwoven web sample are empty of the low surface tension fluid. The gas flow versus pressure data represents the "wet curve." When the curve continues to rise linearly, the sample is considered to be dry (i.e., the pores are emptied of the low surface tension fluid). The pressure is then decreased in steps producing the "dry curve." From the relationships of the "wet" and "dry" curves, the computer calculates the pore parameters including the mean-flow pore diameter and a histogram of pore diameters across the tested range (e.g., from the bubble point down to about 0.08 microns or even less with higher gas pressure) as is known to those of skill in the porous media field.

Some key parameters for the test procedure with the capillary flow porometer are the following: the test fluid is Galwick with 15.9 mN/m surface tension; the test area opening size is 7 mm; and the tortuosity parameter is set to 1. Other parameters of the instrument are set to max flow: 100,000 cc/min, bubble flow 3 cc/min, F/PT parameter 1000, zero time 2 s, v2incr 25 cts*3, preginc 25 cts*50, pulse delay 0s, maxpres 1 bar, pulsewidth 0.2 s, mineqtime 10 s, presslew 10 cts*3, flowslew 30 cts*3, equiter 10*0.1 s, aveiter 10*0.1 s, max press diff 0.01 bar, max flow diff 40 cc/min, starting press 0.1 bar, and starting flow 500 cc/min.

Nonwoven Tensile Strength (in CD)

The nonwoven tensile strength (in CD) is measured using an Instron MTS 3300 tensile tester, or equivalent according to WSP 110.4(05)B. A nonwoven web sample of 15 mm×50 mm, where the 50 mm length is along the length of the diaper product. The sample width is 50 mm, The gauge length is 5 mm, allowing for 5 mm to be placed in each sample clamp. The test speed is 100 mm/min. A stress-strain curve is measured until the sample breaks. The nonwoven tensile strength is defined as the maximum stress value observed of the curve.

Bond Peel Strength

The bond peel strength is defined as the force required to separate the two bonded layers of barrier leg cuff and the topsheet in the longitudinal direction. The test is measured using an MTS 3300 tensile tester or equivalent. A nonwoven laminate specimen of 15 mm×170 mm is removed from the product. A free end is created in the last 20 mm by manually peeling apart the topsheet from the barrier leg cuff layer, thus obtaining a free end with a cuff face and a topsheet face. The test speed is 305 mm/min. The specimens are obtained from the product as described in the Mechanical Bond defect occurrence rate test.

Procedure
- Insert the free end of the barrier leg cuff layer of the specimen into the lower jaw with the length axis of the sample perpendicular to the upper edge of the jaw, and close the jaw. Align the specimen between the lower and upper jaws. Insert the free end of the topsheet layer of the specimen into the upper jaw with the length axis of the sample perpendicular to the lower edge of the jaw and close the jaw with enough tension to eliminate any slack, but less than 5 grams of force on the load cell. Do NOT zero the instrument after the specimen has been loaded.
- Start the tensile tester and data collection device simultaneously as described by the manufacturer's instructions.
- Remove the specimen from the clamps and return the crosshead to the starting position in preparation for the next specimen.
- If tearing has occurred during testing, cut another specimen from the same general area of the sample. If tearing occurs during testing of this second specimen also, record the bond strength for the specimen as "total bond".
- Disregard results for the first 2.5 cm of peel. If the tensile tester is computer interfaced, set the program to calculate the average peel force in grams for the specimen.

The amount of elemental silicon coated on a surface is determined by a silicon analysis performed at an external accredited laboratory (e.g., Advanced Testing Laboratory, Cincinnati, Ohio) using compendial methods. HSC coated samples, as described herein, that are submitted for Silicon Analysis primarily include siloxane polymers, which contain elemental silicon, as the hydrophobic active component and nonwoven material, which may be coated or uncoated. Thus, an elemental silicon analysis on the HSC coated nonwoven substrates can detect and quantify the amount of silicone present, which can then be correlated to the amount of HSC present on the coated substrate.

Liquid Strike-Through

The barrier performance of the coated substrates is determined by measuring the time in which a liquid added to the surface of the substrate penetrates the surface of the substrate. The test method conforms to the European Disposables And Nonwovens Association ("EDANA") method No. 150.3-96 using a Lister SN L5725 Model 1998 and an aqueous solution of 0.042% Triton-X-100, which is commercially available through Aldrich Chemicals. The surface tension of the solution should be approximately 30 mN/m-32 mN/m). The test solution is prepared by the following procedure:

Materials Needed: 2.6 g Triton-X-100
- 1.0 L Beaker
- 6.0 L Erlenmeyer Flask
- 1.0 L Graduated Cylinder
- Stir Bar
- Distilled Water
- Analytical Balance (at least 1 kg capacity/2-place)
- Foil Procedure to Prepare 5.0 L:
1. Thoroughly clean and rinse a 6.0 L flask and 1.0 L beaker.
2. Zero the Analytical Balance with doors/lid closed.
3. Place the clean, dry 1.0 L beaker onto the balance, and tare the balance.
4. Using a disposable pipette, carefully add 2.10 g of Triton-X-100 directly to the beaker that is on the balance. Ensure that as you are adding the Triton-X-100 to the flask, you are not getting it on the neck or sides of the beaker.
5. Using a 1.0 L graduated cylinder, add 998 mL of distilled water to the beaker.
6. Pour the contents of the beaker into the 6.0 L flask.
7. Add 1000 mL of distilled water to the beaker to rinse the Triton-X-100.
8. Pour the distilled water into the 6.0 L flask, combining the contents.
9. Repeat steps 6.-8. three additional times.
10. Place a stir bar into the flask.
11. Cover the flask with foil.
12. Place a Safety Label onto the flask (see example below). Use a piece of masking tape to denote the date of preparation and the initials of the person who prepared the solution.
13. Place the flask of solution onto a stir plate to thoroughly mix (approximately 30 minutes should be sufficient).
14. Measure the surface tension of the solution according to the Interfacial Tension Measurement method below to ensure that it is 32±2 dyne/cm.

Dry Migration Test

This method is used to verify the surface modification of a nonwoven material or test for dry migration of surfactants onto neighboring materials by measuring the dry migration of hydrophilic surfactants from a hydrophilic nonwoven raw material to a hydrophobic nonwoven raw material.

Procedure: Alternating pieces of hydrophobic and hydrophilic nonwovens are placed in a stack in the oven at 60° C. A weight is placed on the stack to maximize physical contact among the nonwovens. The stack plus the weight is left in the oven for 48 hours. After the time, the hydrophobic nonwovens are then analyzed by time-of-flight secondary ion mass spectrometry ("TOF-SIMMS"), which measures the surfactant content that has migrated. TOF-SIMMS can be used as a tool to identify chemical materials on the sample surface and is accomplished by comparison of the mass spectra obtained from the sample to reference spectra obtained from the materials deposited on the sample.

Interfacial Tension Measurement and Contact Angle Measurement

The Interfacial Tension Measurement measures the surface tension of a fluid in units of Dyne per centimeter. This test is performed according to ASTM D-1331, titled "Standard Test Method for Surface and Interfacial Tension of Solutions of Surface Active Agents." The Contact Angle Measurement measures the surface energy of a fluid on a surface. This test is according to ASTM D-7334, titled "Standard Practice for Surface Wettability of Coatings, Substrates and Pigments by Advancing Contact Angle Measurement." Lower advanced contact angle values are indicative of wetting and fluids having lower advanced contact angles tend spread faster on a particular nonwoven material, which may be undesirable, for example, when the material is a barrier material.

EXAMPLES

Example 1

In this example, the second nonwoven component layer 132 comprises N-fibers having fiber diameters (measured per the Fiber Diameter and Denier Test set forth herein), polydispersity, fiber diameter ranges (minimum-maximum measured), and amounts of submicron diameter fibers (less than 1 micron) illustrated in Table 1A below:

TABLE 1A

| Sample No. | Number Average Diameter (microns) | Mass Average Diameter (microns) | Polydispersity Ratio | Standard Deviation (microns) | Fiber Diameter Range (microns) | Amount of Submicron Fibers (%) |
|---|---|---|---|---|---|---|
| N1 | 0.34 | 0.39 | 1.14 | 0.09 | 0.15-0.55 | >99% |
| N2 | 0.33 | 0.45 | 1.36 | 0.09 | 0.08-0.78 | >99% |
| N3 | 0.38 | 0.48 | 1.27 | 0.14 | 0.17-0.77 | >99% |
| N4 | 0.68 | 0.73 | 1.08 | 0.14 | 0.40-0.98 | >99% |
| N5 | 0.57 | 0.95 | 1.66 | 0.31 | 0.11-2.23 | 92% |
| N6 | 0.84 | 0.96 | 1.13 | 0.22 | 0.25-1.55 | 74% |
| N7 | 0.85 | 1.02 | 1.19 | 0.27 | 0.26-1.60 | 79% |
| N8 | 0.69 | 1.12 | 1.63 | 0.37 | 0.23-1.84 | 85% |
| N9 | 1.03 | 1.21 | 1.18 | 0.33 | 0.28-1.98 | 43% |
| N10 | 0.78 | 1.23 | 1.59 | 0.39 | 0.29-2.31 | 80% |

Comparative Example 1

A nonwoven component layer comprises meltblown fibers having fiber diameters (measured per the Fiber Diameter and Denier Test set forth herein), polydispersity, fiber diameter ranges (minimum-maximum measured), and amounts of submicron diameter fibers (less than 1 micron) illustrated in Table 1B below.

TABLE 1B

| Sample No. | Number Average Diameter (microns) | Mass Average Diameter (microns) | Polydispersity Ratio | Standard Deviation (microns) | Fiber Diameter Range (microns) | Amount of Submicron Fibers (%) |
|---|---|---|---|---|---|---|
| M1 | 0.69 | 1.64 | 2.39 | 0.58 | 0.15-2.68 | 80% |
| M2 | 0.45 | 1.97 | 4.35 | 0.44 | 0.10-5.55 | 93% |
| M3 | 0.61 | 2.99 | 4.91 | 0.65 | 0.07-8.44 | 86% |
| M4 | 1.36 | 1.86 | 1.37 | 0.56 | 0.41-3.32 | 21% |
| M5 | 1.78 | 2.15 | 1.21 | 0.55 | 0.84-3.99 | 4% |
| M6 | 1.44 | 2.25 | 1.56 | 0.71 | 0.46-4.40 | 26% |
| M7 | 1.71 | 2.62 | 1.54 | 0.82 | 0.70-4.76 | 10% |
| M8 | 3.16 | 4.16 | 1.32 | 1.23 | 1.80-6.80 | 0% |
| M9 | 1.85 | 4.10 | 2.22 | 1.39 | 0.67-6.44 | 23% |
| M10 | 1.54 | 4.60 | 2.99 | 1.47 | 0.20-8.18 | 38% |
| M11 | 2.27 | 6.17 | 2.72 | 1.85 | 0.55-12.17 | 10% |

In Table 1B, the samples identified by the numbers M1 through M3 represent ultra-fine meltblown fibers, the samples identified by the numbers M4 through M7 represent fine meltblown fibers, and the samples identified by the numbers M8 through M11 represent intermediate meltblown fibers.

Figure 26:
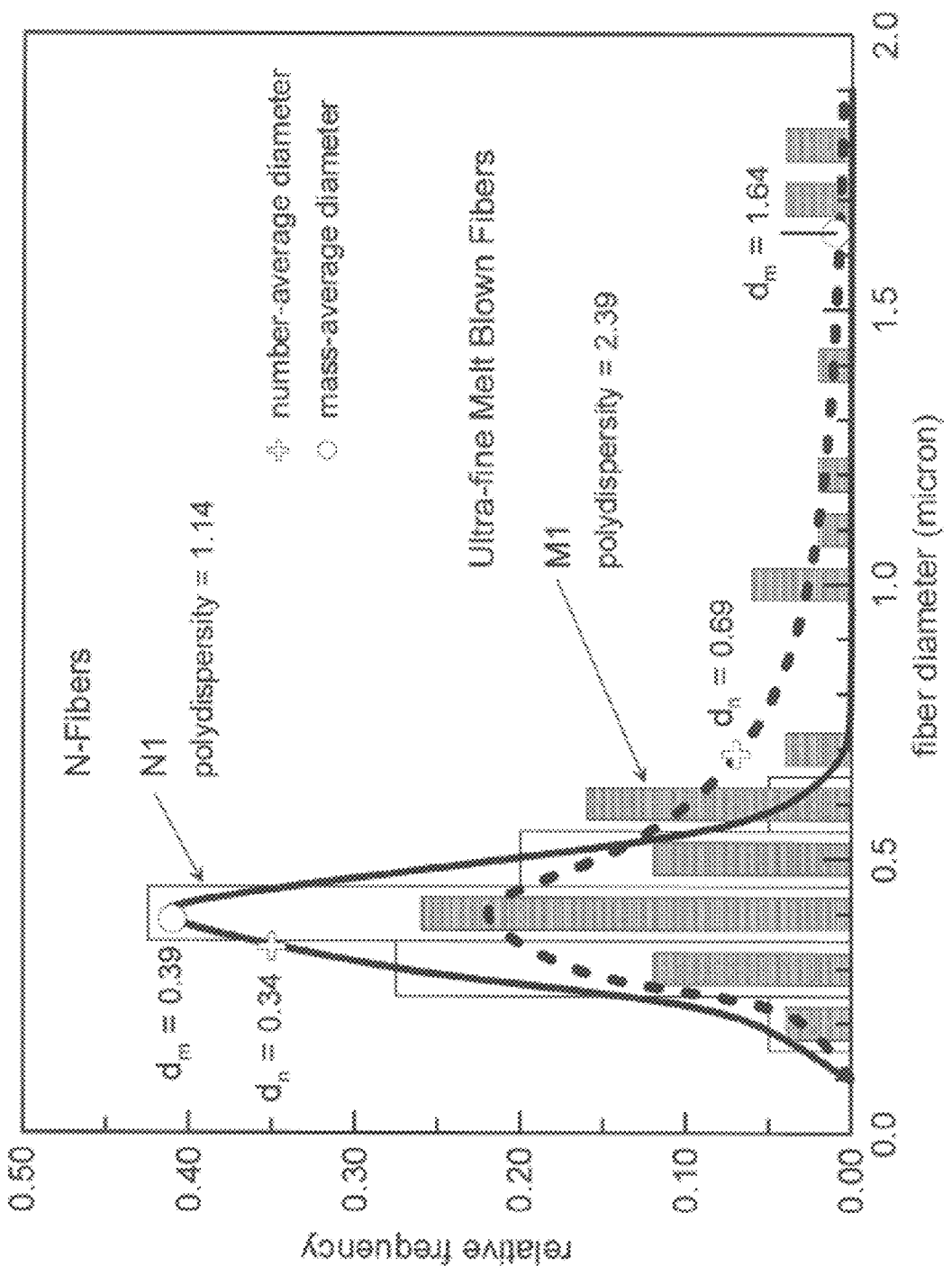
FIGS. 26-29 graphically illustrate data from Tables 1A and 1B of Example 1.
Figure 27:
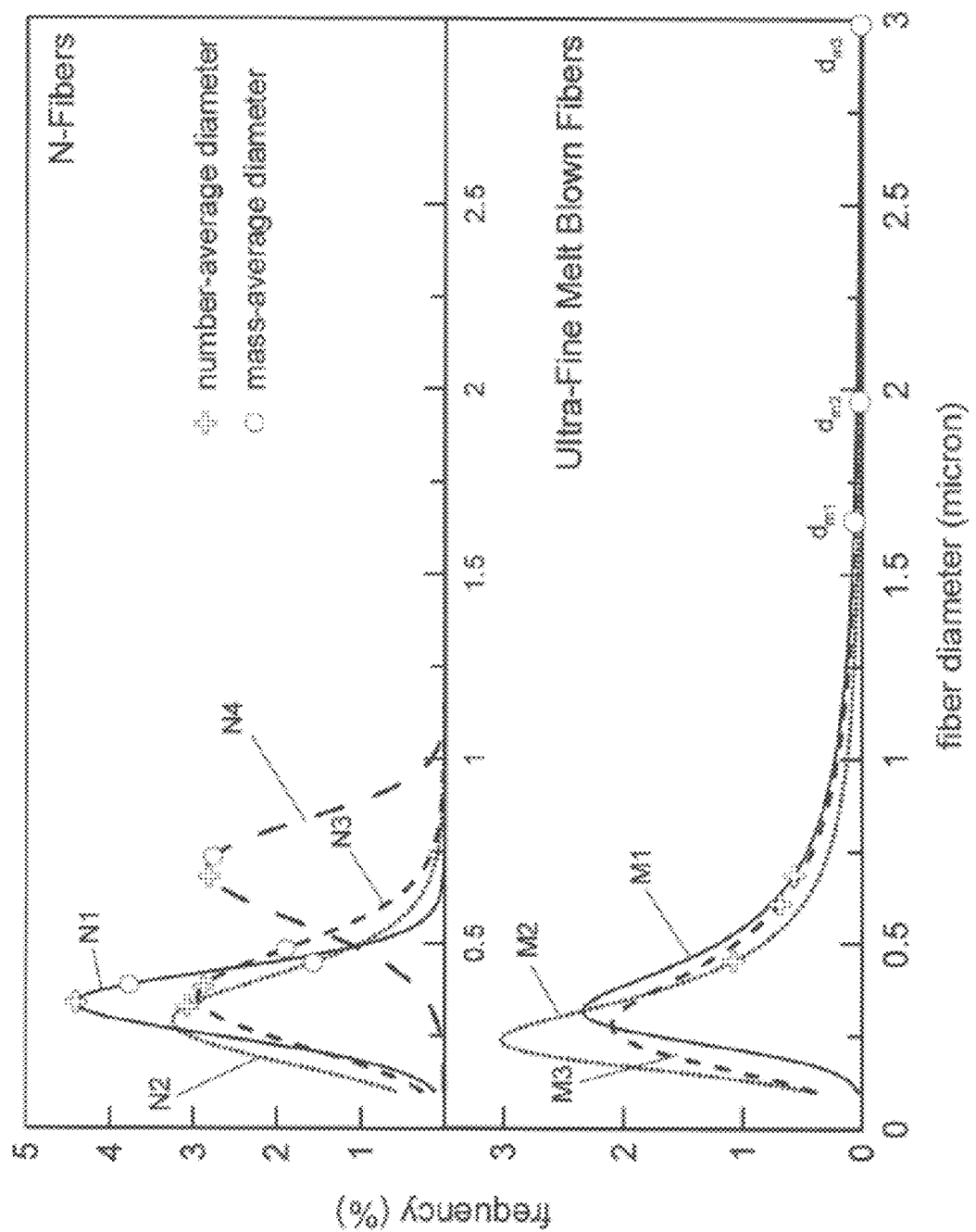
Figure 28:
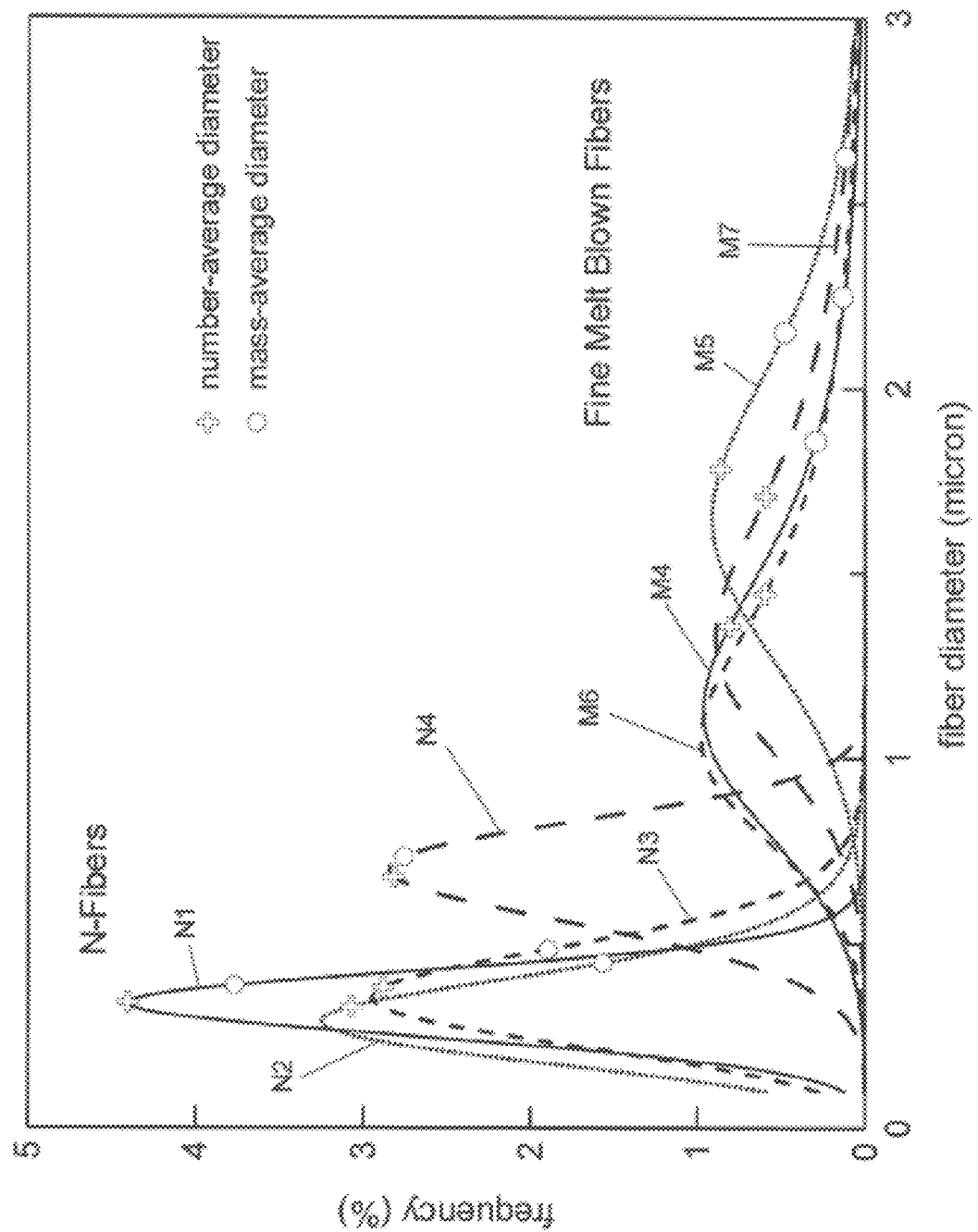
Figure 29:
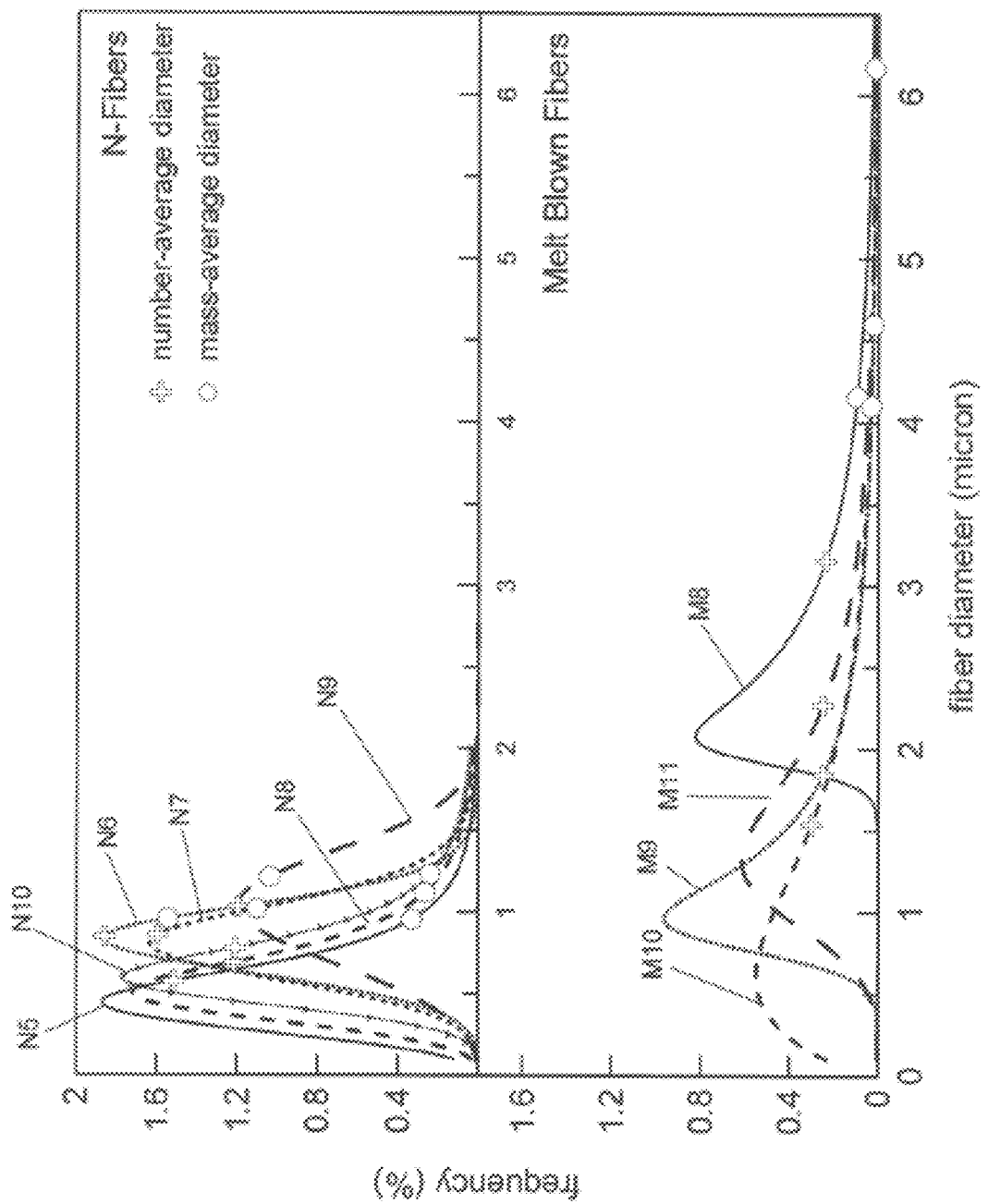

The data set forth in Table 1A and Table 1B is illustrated in FIGS. 26 through 29. The number average diameter and the mass average diameter values, shown in the Tables 1A and 1B, are depicted on the statistically fitted curves to the fiber diameter distributions in FIGS. 26 through 29. FIG. 26 compares the fiber diameter distribution of the N-Fibers sample N1 with the fiber diameter distribution of the ultra-fine meltblown fibers sample M1. Similarly, FIG. 27 compares the fiber diameter distribution of the N-Fibers samples N1 through N4 with the fiber diameter distribution of the ultra-fine meltblown fibers samples M1 through M3. The comparison of N-Fibers and ultra-fine meltblown fibers shows that even though ultra-fine meltblown fibers samples comprise significant number of fibers (at least 80%) with diameters less than 1 micron, they also comprise finite number of fibers (about 6% to 20%) with diameters greater than 1 micron (to up to 8.4 microns), making the fiber distributions with long tails on the large diameter end. The long large diameter end tails of fiber distributions are well-described by the mass average diameters, which range between 1.64 and 2.99 along with a polydispersity ratio ranging between 2.39 and 4.91. FIGS. 28 and 29 compare the fiber diameter distributions of N-Fibers samples N1 through N4 with the fine and intermediate size meltblown fiber samples, respectively. The meltblown fiber samples are labeled in FIGS. 28 and 29. The fiber diameter distributions of the meltblown samples in FIGS. 28 and 29, and Table 1B depict that fiber diameters range from submicron (<1 micron) to as large as 12 microns, making the fiber distribution significantly wide with long tails on the large fiber diameter end. Owing to the presence of large diameter fibers (illustrated by the long tails of the fiber distributions on the large fiber diameter end) in the measured samples, listed in Table 1B, both the mass average and the number average diameters for all the measured meltblown samples lie on the distribution tails, and the mass average diameters are more than about 1 standard deviation greater than the number average diameters. In comparison, the N-fibers have a very small number of large diameter fibers in the measured samples. Therefore, the fiber diameter distributions of N-Fibers have short tails, and both the number average and the mass average diameters are tended towards the center of the fiber distributions, and are within about 1 standard deviation of the number average diameters.

Example 2A

Figure 30:
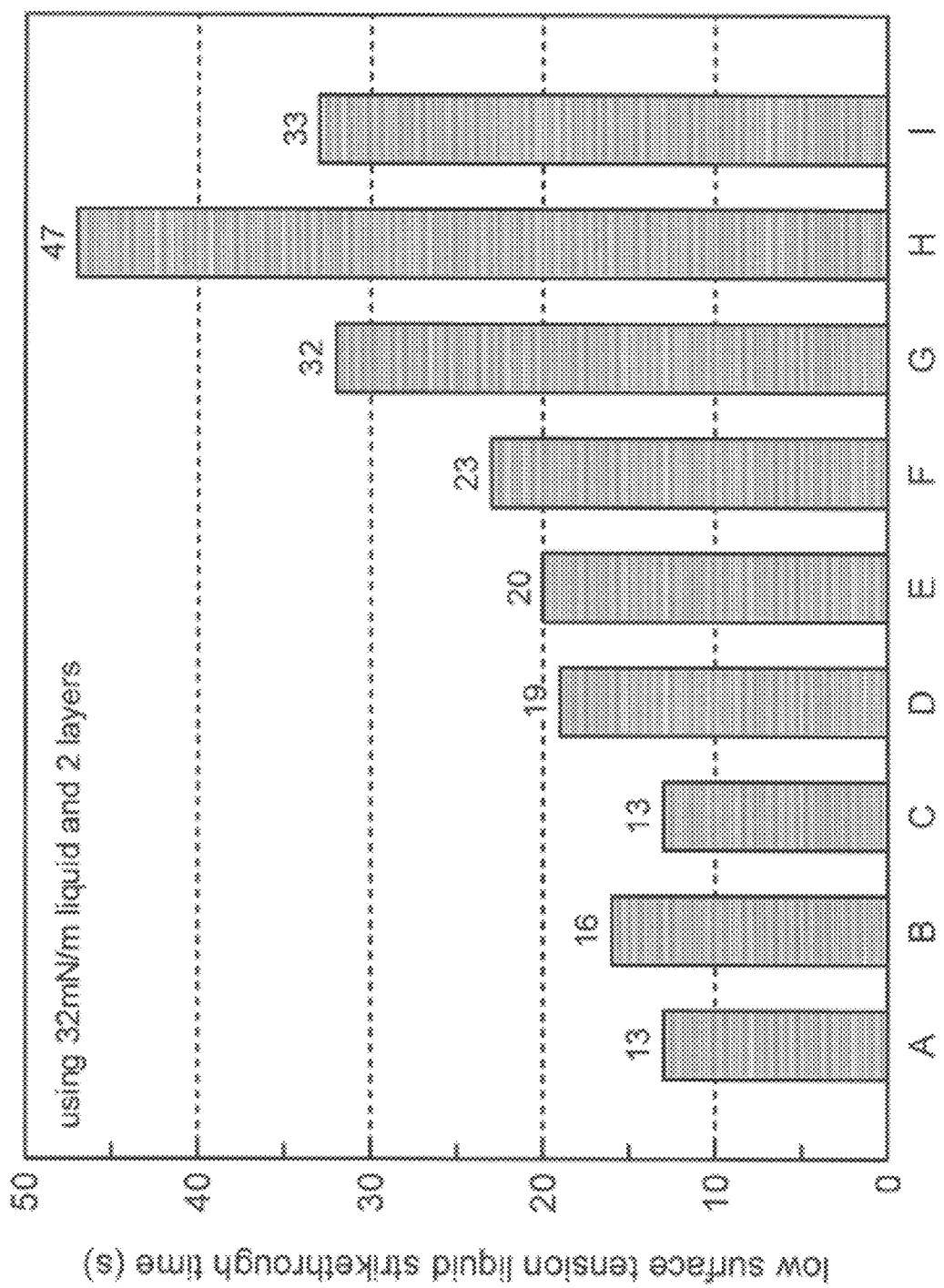
FIG. 30 graphically illustrates the low surface tension fluid strikethrough times of various samples of Table 2A of Example 2A.

In this example, various samples of nonwoven web materials A-i are tested. Their various properties are displayed in Table 2A. Samples G-i are embodiments of nonwoven web materials of the present disclosure, while SMS samples A-F are provided merely for comparison purposes. The low surface tension fluid strikethrough times of the various samples are illustrated graphically in FIG. 30 (with the exception of sample J to provide a graph with a better scale). As can be seen from FIG. 30, the low surface tension fluid strikethrough times of samples G-I of the present disclosure are significantly higher than SMS samples A-F, even when the SMS webs are coated with a hydrophobic coating (see SMS samples D-F). The low surface tension fluid strikethrough values are determined using two plies of each sample and a 32 mN/m low surface tension fluid.

TABLE 2A

| Sample No. | Material Type | Total Basis Weight (g/m$^2$) | Fine Fiber Basis Weight (g/m$^2$) | Low Surface Tension Fluid Strikethrough (s) | Air Permeability (m/min) |
|---|---|---|---|---|---|
| A | SMS | 15.7 | 1 | 13 | 91 |
| B | SMS | 16.9 | 3 | 16 | 72 |
| C | SMS | 13.3 | 1.5 | 13 | 80 |
| D | SMS + Hydrophobic Coating 1 | 15.2 | 1 | 19 | 96 |
| E | SMS + Hydrophobic Coating 1 | 17.1 | 3 | 20 | 84 |
| F | SMS + Hydrophobic Coating 2 | 15.1 | 1 | 23 | 70 |
| G | SNS | 15.5 | 1.5 | 32 | 52 |
| H | SNS + Hydrophobic Coating 1 | 15.6 | 1.5 | 47 | 50 |
| I | SMNS | 13.3 | 1 (M) + 1 (N) | 33 | 59 |

Example 2B

Figure 31:
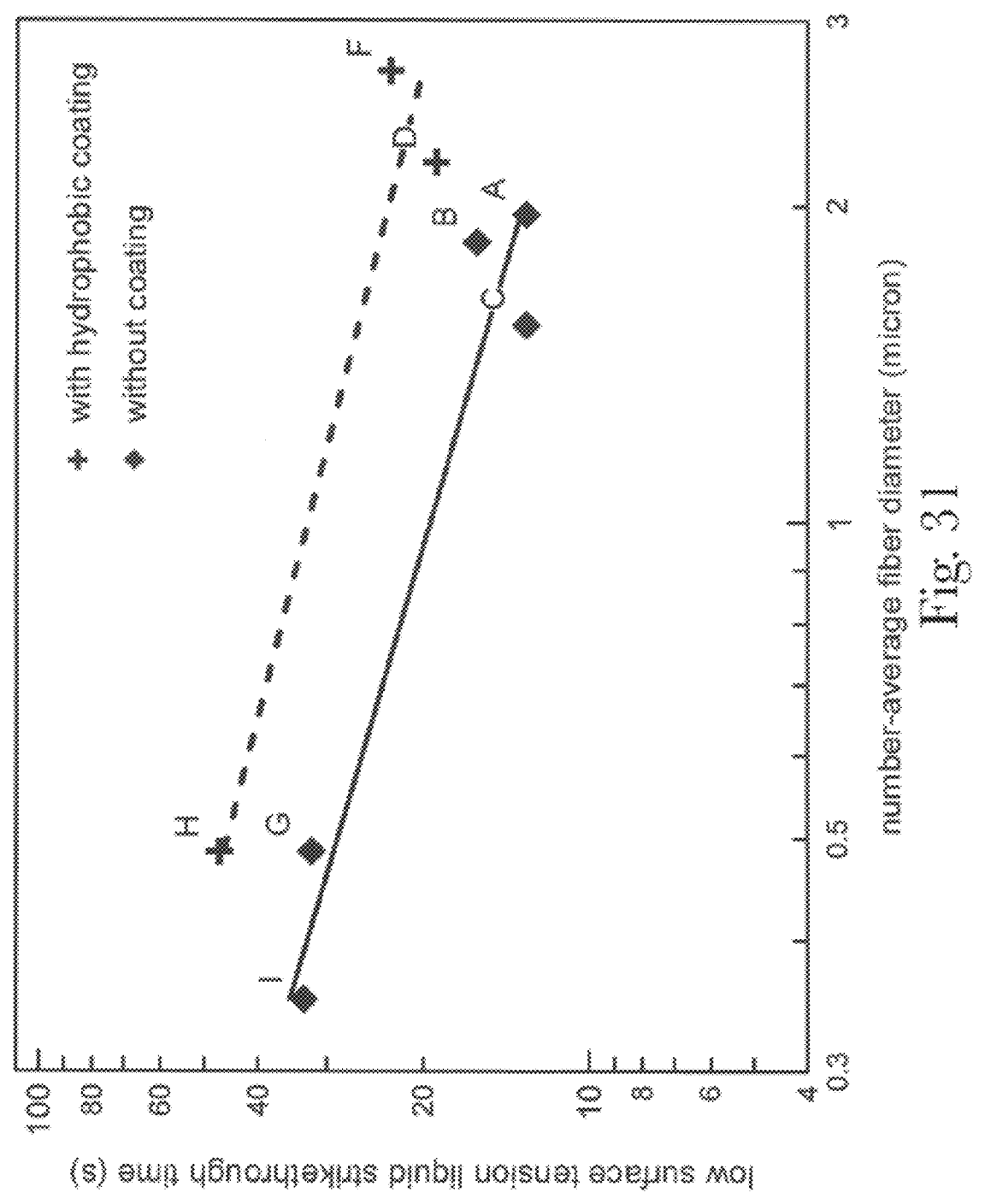

In this example, various samples of nonwoven web materials A-I (same as Example 2A) are tested. Their various properties are displayed in Table 2B. Samples G-I are embodiments of nonwoven web materials of the present disclosure, while SMS samples A-F are provided merely for comparison purposes. The low surface tension fluid strikethrough times of the various samples are plotted against their number average diameter (microns) in FIG. 31. As is illustrated in FIG. 31, the low surface tension fluid strikethrough time increases based on the smaller number average diameter of the fibers in the sample. The low surface tension fluid strikethrough values are determined using two plies of each sample and a 32 mN/m low surface tension fluid.

TABLE 2B

| | Sample ID | | | | | | |
|---|---|---|---|---|---|---|---|
| | A | B | D | F | G | H | I |
| Material Type | SMS | SMS | SMS | SMS | SNS | SNS | SMNS |
| Hydrophobic Coating | — | — | Type 1 | Type 2 | — | Type 1 | — |
| Total Basis Weight (g/m$^2$) | 15.7 | 16.9 | 15.2 | 15.1 | 15.5 | 15.6 | 13.3 |
| MeltBlown Fiber Basis Weight (g/m$^2$) | 1 | 3 | 1 | 1 | — | — | 1 |
| N-Fiber Basis Weight (g/m$^2$) | — | — | — | — | 1.5 | 1.5 | 1 |
| Spunbond Number Average Diameter (micron) | 14.85 | 15.57 | 15.95 | 18.40 | 16.98 | 16.98 | 15.61 |

TABLE 2B-continued

| Material Type | Sample ID | | | | | | |
|---|---|---|---|---|---|---|---|
| | A SMS | B SMS | D SMS | F SMS | G SNS | H SNS | I SMNS |
| Spunbond Mass Average Diameter (micron) | 15.03 | 15.71 | 16.10 | 18.47 | 16.99 | 16.99 | 15.67 |
| MeltBlown Number Average Diameter (micron) | 1.96 | 1.85 | 2.20 | 2.69 | — | — | 2.04 |
| MeltBlown Mass Average Diameter (micron) | 2.46 | 4.10 | 2.93 | 3.10 | — | — | 3.72 |
| Submicron M Fibers (%) | 8% | 23% | 2% | 0% | — | — | 11% |
| N-Fibers Number Average Diameter (micron) | — | — | — | — | 0.49 | 0.49 | 0.35 |
| N-Fibers Mass Average Diameter (micron) | — | — | — | — | 0.54 | 0.54 | 0.43 |
| Submicron N Fibers (%) | — | — | — | — | >99% | >99% | >99% |
| Low Surface Tension Fluid Strikethrough (s) | 13 | 16 | 19 | 23 | 32 | 47 | 33 |
| Air Permeability (m/min) | 91 | 72 | 96 | 70 | 52 | 50 | 59 |

Example 2C

Figure 32:
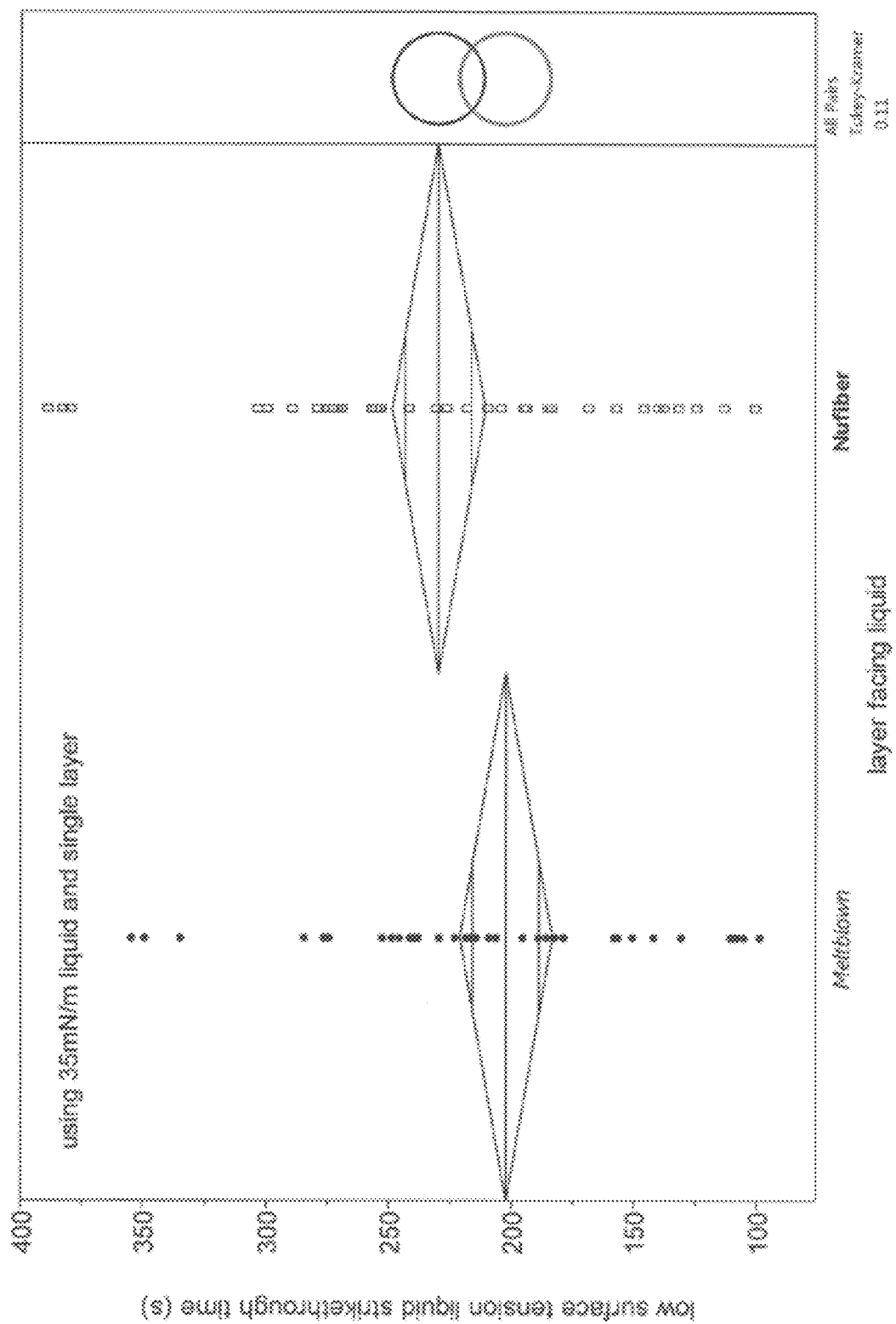
FIG. 32 graphically illustrates the sidedness of an SMNS web of the present disclosure having the properties specified in Table 2C.

In this example, the sidedness (i.e., which layer, the meltblown layer or the N-fiber layer, is positioned more proximal to the source of the low surface tension fluid) of the SMNS nonwoven webs of the present disclosure is illustrated against the low surface tension fluid strikethrough times of the SMNS webs. Referring to FIG. 32, in the data set on the left, the meltblown layer (i.e., the fourth nonwoven component layer) was positioned more proximal to the low surface tension fluid than the N-fiber layer in an SMNS web sample. In the data set on the right, the N-fiber layer (i.e., the second nonwoven component layer) was positioned more proximal to the low surface tension fluid than the meltblown layer of the SMNS sample. As illustrated in FIG. 32, when the N-fiber layer is positioned closer to the source of the fluid, the SMNS web provides a higher low surface tension fluid strikethrough time.

Turning to Table 2C below, a single layer of the SMNS web is tested using the 35 mN/m Low Surface Tension Fluid Strikethrough Test.

TABLE 2C

| | M facing liquid | N facing liquid |
|---|---|---|
| LSTST at 35 mN/m, 1 layer | Liquid → SMNS | Liquid → SNMS |
| Average | 202 | 230 |
| StDev | 69.1 | 76.8 |

The single layer SMNS web has a basis weight of 13 gsm (for more specifics, see sample I in Example 2A and 2B). The variation in this Example 2C is which side of the SMNS material is facing the source of the fluid (i.e., is the material positioned fluid-SMNS or fluid-SNMS). In the set of data on the left side of FIG. 32, the sample is positioned fluid-SMNS and in the data set on the right side of FIG. 32 is positioned fluid-SNMS.

Statistical analysis shows that when the N-layer is positioned most proximal to the low surface tension fluid source, a statistically significant benefit of greater low surface tension fluid strikethrough times (with 89% certainty) is provided. Therefore, in one embodiment, an absorbent article of the present disclosure, using the SMNS web as a barrier to fluid penetration, may have the N-layer of the SMNS web facing inwards, towards the wearer of the absorbent article (i.e., wearer-SNMS). This concept is illustrated in FIG. 3A, where the N-layer of the longitudinal barrier cuff 51 is positioned more proximal to the central longitudinal axis 59 than the than the M-layer.

Example 2D

In this example, a single layer of a nonwoven web is tested using the 35 mN/m Low Surface Tension Fluid Strikethrough Test. Table 2D shows the results of some comparative samples (SMS) and a sample of an SMNS web of the present disclosure.

TABLE 2D

| Material | LSTST 1 layer at 35 mN/m (Average, s) |
|---|---|
| 15 gsm SMS (1 gsm M, 7 + 1 + 7 gsm total) (= sample A) | 81.0 |
| 15 gsm SMS (3 gsm M, 6 + 3 + 6 gsm total) (= sample B) | 133.9 |
| Hydrophobic surface coated 15 gsm SMS (1 gsm M; additive is PDMS with surface energy 20 mN/m) (= sample D) | 311.7 |
| SMNS* 13 gsm (5.5 + 1 + 1 + 5.5 gsm total) (= sample I) | 229.6 |

The first sample in this table is equal to sample A of Example 2A and 2B. The second sample is similar to sample B of Example 2A and 2B, but has a lower overall basis weight (i.e., less spunbond basis weight) the fiber diameters of sample B's meltblown layer have a number average diameter between 2 and 3 micrometers and a mass-average diameter of about 4 micrometers. The third sample in Table 2D is sample D from Example 2A and 2B and is coated with a hydrophobic surface additive according to Catalan in U.S. Pat. Publ. No. 2006/0189956 A1 in the following manner: a 3% solution of a vinyl terminated PDMS (commercially available from Momentive as SM3200) and a methyl hydrogen PDMS (commercially available from Momentive as SM3010) is prepared and mixed for 30 minutes. The SMS web is dipped into the solution and the excess liquid is squeezed out such that at least about 400 μg/g of the aqueous silicone mixture is deposited on the SMS web. The SMS web is then dried in a convective oven at 120° C. for 1 minute and then cooled and stored in a dry and clean location until the SMS web is ready for testing. The weight gain of the SMS web (i.e., the dry coating amount per square meter) needs to be less than 1%. The fourth sample in Table 2D is sample I from Example 2A and 2B.

Figure 33:
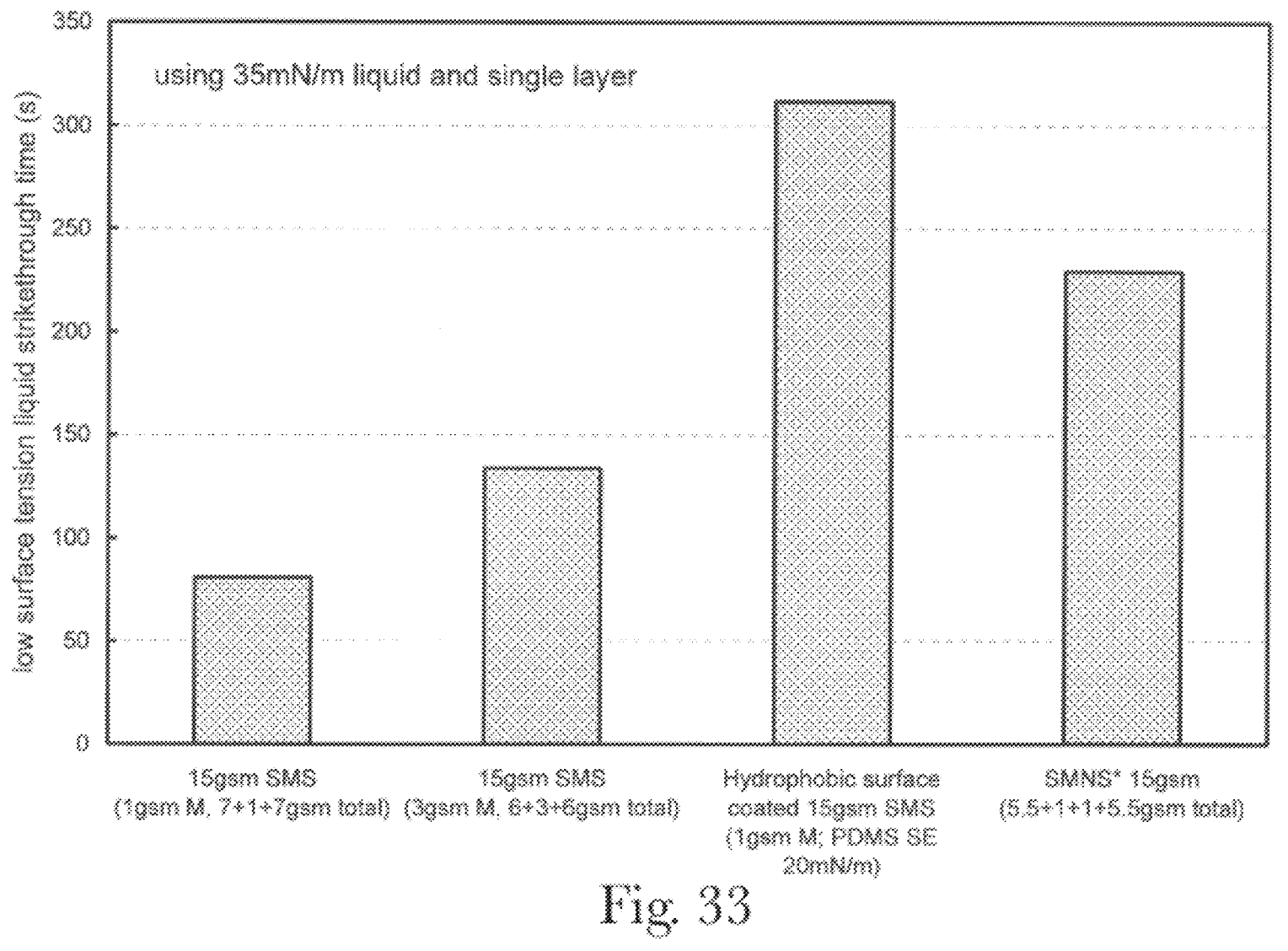
Figure 34:
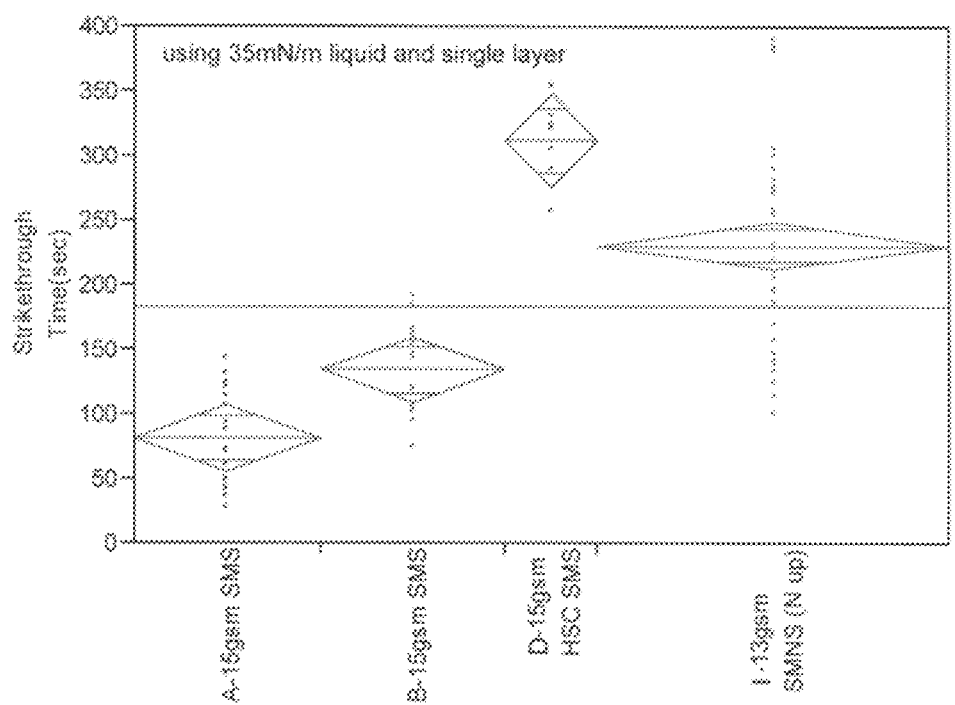

Referring to FIGS. 33 and 34, sample I shows a surprisingly large advantage in low surface tension fluid strikethrough times compared to the SMS samples (the first three samples of Table 2D) and is more than halfway to the performance of a hydrophobic-coated SMS in this single layer 35 mN/m Low Surface Tension Fluid Strikethrough Test. The SMNS sample (sample I) has a lower total basis weight than any of the other SMS samples (the first three samples of Table 2D), and does not have the advantage of the PDMS coating which has a low surface energy of 20 mN/m to provide a higher contact angle. Sample I, even with having such a low basis weight and such a low fine fiber basis weight, and without hydrophobic chemical modification, still is capable of producing very high low surface tension fluid strikethrough times (e.g., above 150 seconds or even above 200 seconds).

Example 3

Figure 35:
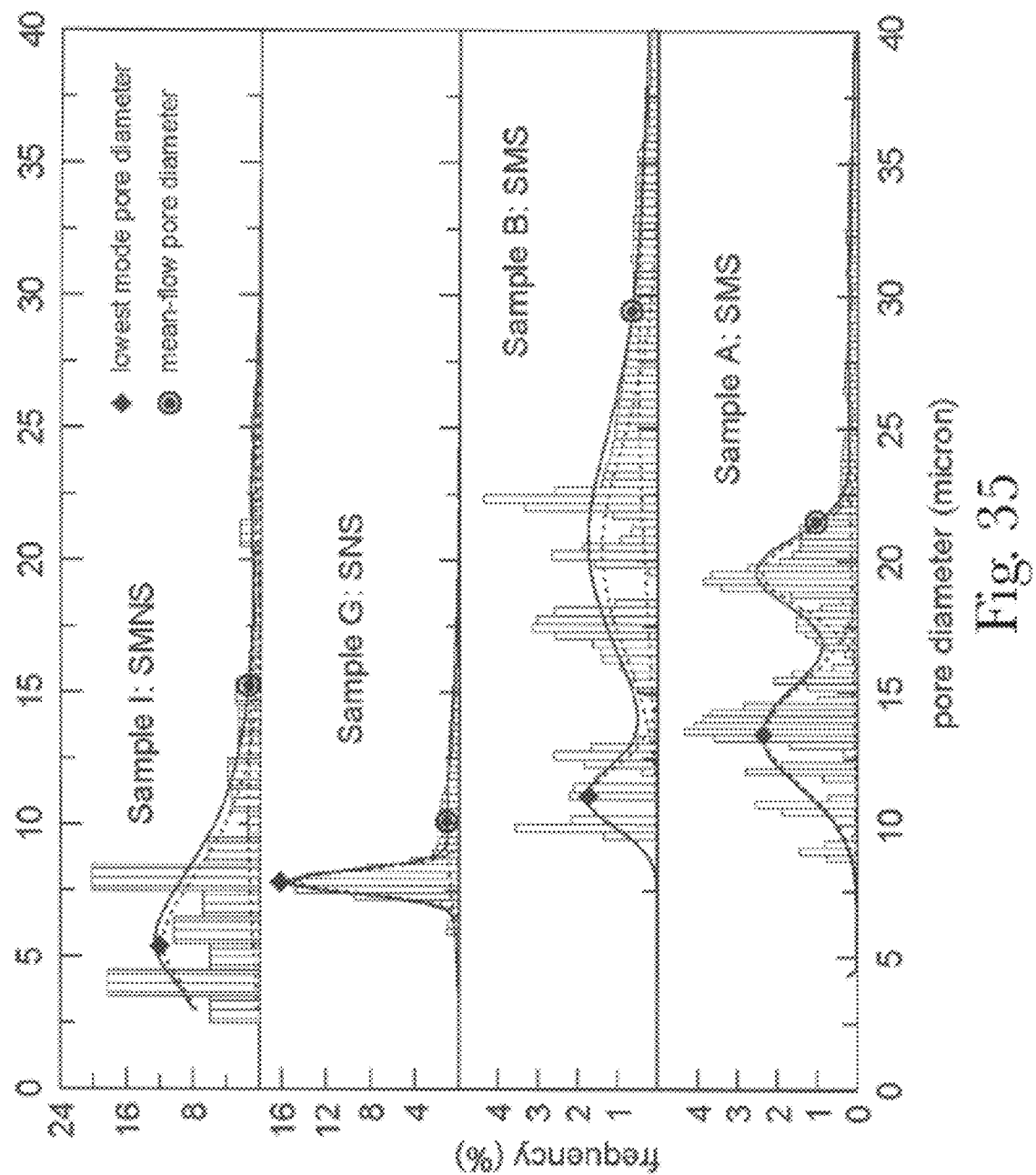
FIG. 35 graphically illustrates the pore size distribution of Samples G, B, and A with respect to Example 3.

In this example, pore size distribution of the SMS samples A and B from Example 2A are compared with the SNS sample G and the SMNS sample I from Example 2A. The pore size distribution of the embodiment of samples G and I comprising N-fibers as the finest fiber layer is significantly different and much narrower than the SMS samples A and B comprising meltblown fibers as the finest fiber layer, as illustrated in FIG. 35. The pore size distributions for all the samples have been statistically fitted with a mixture of constituent distributions (shown as dotted lines in the FIG. 35) corresponding to fine fiber and spunbond layers, with the largest pores corresponding to the spunbond layer because of larger fiber diameters than the fine fibers. While the largest mode corresponds to the largest frequency of the thick spunbond fibers, the lowest mode corresponds to the largest frequency of the fine fibers, and the intermediate mode (for the samples A, B, and I) corresponds to the largest frequency of intermediate size fibers. The lowest mode value, mean flow, and bubble point pore diameters describing the pore size distribution are listed in Table 3 below for the samples A, B, G, and I along with their respective basis weights, fiber size distributions, low surface tension fluid strikethrough times, and air permeability values. The percent flow blocked by the lowest mode diameter is calculated from intersection of the "wet flow" and "dry flow" curves (set forth in the Pore Size Distribution Test) at the pressure corresponding to the lowest mode diameter. Table 3 also shows that the mean flow pore diameter correlates with the mass-average diameter. Additionally, the low surface tension fluid strikethrough time and air permeability correlate with the mean flow and the lowest mode pore diameters. Clearly, samples G and I of the present disclosure have significantly smaller pores and significantly longer low surface tension fluid strikethrough times when compared to SMS samples A and B.

TABLE 3

| | Sample ID | | | |
|---|---|---|---|---|
| Material Type | A SMS | B SMS | G SNS | I SMNS |
| Total Basis Weight (g/m²) | 15.7 | 16.9 | 15.5 | 13.3 |
| MeltBlown Fiber Basis Weight (g/m²) | 1 | 3 | — | 1 |
| N-Fiber Basis Weight (g/m²) | — | — | 1.5 | 1 |
| MeltBlown Number-Average Diameter (microns) | 1.96 | 1.85 | — | 2.04 |
| MeltBlown Mass-Average Diameter (microns) | 2.46 | 4.10 | — | 3.72 |
| Submicron M Fibers (%) | 8% | 23% | — | 11% |
| N-Fibers Number-Average Diameter (microns) | — | — | 0.49 | 0.35 |
| N-Fibers Mass-Average Diameter (microns) | — | — | 0.54 | 0.43 |
| Submicron N Fibers (%) | — | — | >99% | >99% |
| Lowest Mode Pore Diameter (microns) | 13.5 | 11.1 | 7.8 | 5.2 |
| Flow Blocked by the Lowest Mode Pore Diameter (microns) | 7% | 1% | 19% | 9% |
| Mean Flow Pore Diameter (microns) | 21.4 | 29.5 | 10.1 | 15.1 |
| Bubble Point Pore Diameter (microns) | 67.2 | 79 | 69.1 | 110.1 |
| Low Surface Tension Fluid Strikethrough Time (secs) | 13 | 16 | 32 | 33 |
| Air Permeability (m/min) | 91 | 72 | 52 | 59 |

Surprisingly, the mean flow pore diameter appears to be more important than the bubble point in order to obtain low surface tension fluid strikethrough times above 12 seconds with untreated (no hydrophobic additive) nonwoven webs having a basis weight of 15 gsm or less with 3 gsm or less fine fibers (i.e., less than 1 micron). Thus, in one embodiment, a mean flow pore diameter of 15 microns or less, alternatively of 12 microns or less, alternatively of 10 microns or less is provided. A mean flow pore diameter greater than 1 micron, alternatively greater than 3 microns, and alternatively greater than 5 microns, is provided for breathability.

Example 4

In this example, the mechanical bonds of various nonwoven webs are evaluated using the basis weight coefficient of variation (COV) of 900 mm² samples. 5 m samples of the same materials are bonded to a 12 gsm topsheet in a docking station using a hem bond pattern at 3.5 bar and a linear speed of ~300 m/min. Various samples of web materials BLC1-BLC6 are tested. Their various properties are displayed in Table 4.

TABLE 4

| Sample No. | Material Type |
|---|---|
| BLC1 | 13 gsm SSMMMS (with 4 gsm M) |
| BLC2 | 13 gsm SMMMS (with 1 gsm M) |
| BLC3 | 13 gsm SMMMS #2 (with 1 gsm M) |
| BLC4 | 13 gsm SSMS (with 1 gsm M) |
| BLC5 | 15 gsm SNS (1.5 gsm N, sample G) |
| BLC6 | 15 gsm SMS (1 gsm M) |

The mechanical bond defects are characterized using the following criteria:

"Hole": an aperture with a size of at least 0.39 mm² in the bond area (hole defect limit). Hole failures are classified as H1, H2, . . . , or H5, with the number reflecting the number of consecutive mechanical bonds with a hole. Consecutive defects are counted as a single defect, i.e., 5 holes are counted as one H5 defect.

"Skip": a mechanical bond is missing at least an area of 1.00 mm² (skip defect limit). Skip failures are classified as S1, S2, . . . , or S5, with the number reflecting the number of consecutive missing mechanical bonds. Consecutive defects are counted as a single defect, i.e., 5 skips are counted as one S5 defect.

"Tear": a tearing of the perimeter such that 1.0 mm or greater of the perimeter of the grommet ring has been torn (tear defect limit). Tear failures are classified as T1, T2, . . . , or T5, with the number reflecting the number of consecutive missing mechanical bonds. Consecutive defects are counted as a single defect, i.e., 5 tears are counted as one T5 defect.

The total number of defects was added up of each kind of defect.

It should be noted that a SSMMMS 13 gsm (sample BLC1) barrier leg cuff shows a significant increase in the number of mechanical bond defects. Extrapolation of a linear fit of BLC1, BLC2, BLC3, and BLC4 leads to an intersection with the horizontal line of BLC6 at a basis weight COV of 0.03 (3%). Therefore, a basis weight COV (local basis weight variation) of 0.03 would be needed in order to attain the current levels of defects found for the 15 gsm barrier leg cuff when using a 13 gsm barrier leg cuff.

Figure 36:
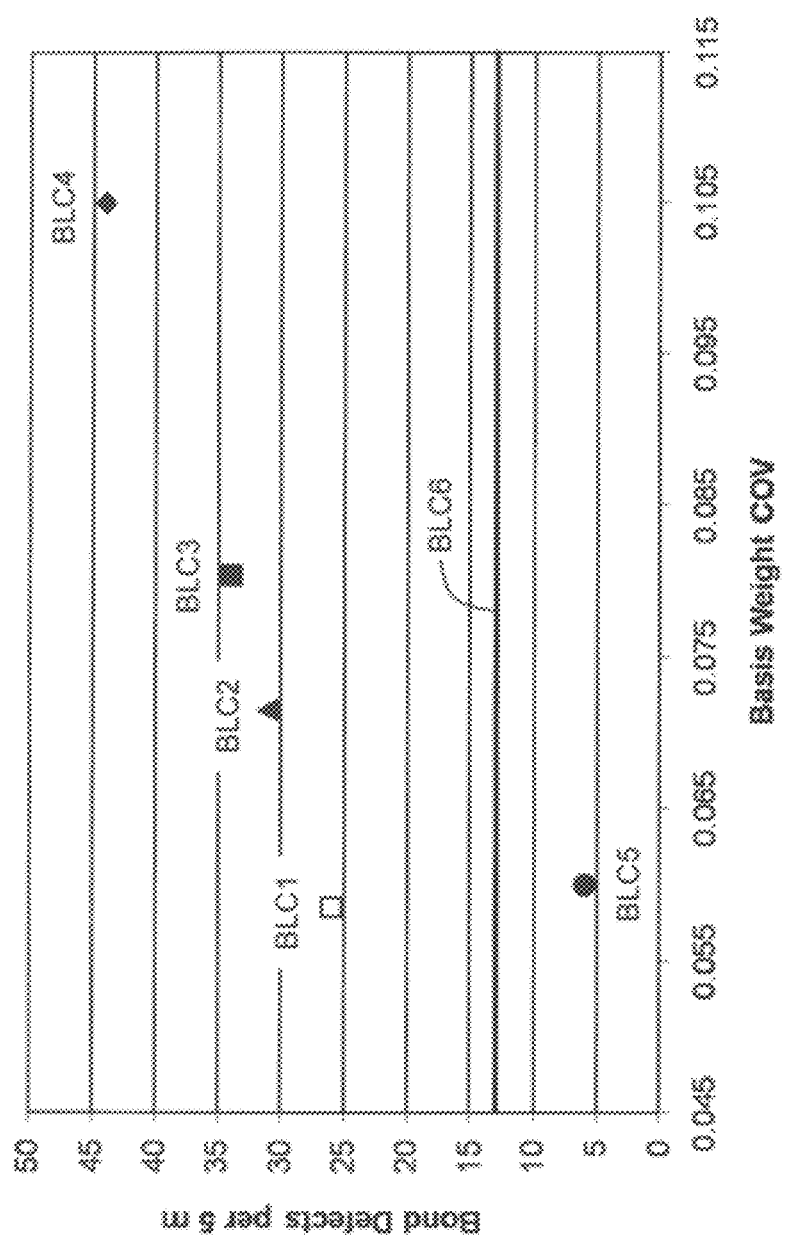
FIG. 36 graphical illustrates the bond defects of various samples of Table 4 as a function of basis weight COV.
Figure 37A:
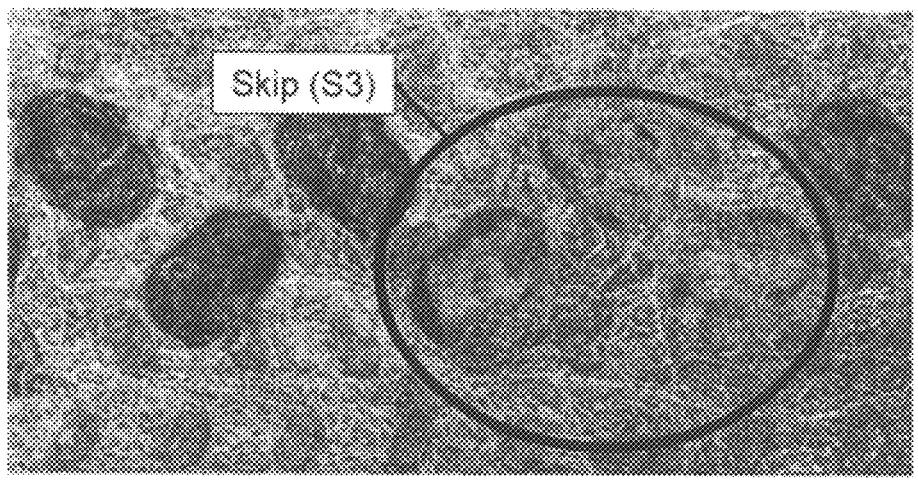
FIGS. 37A-37G illustrate examples of various mechanical bonds.
Figure 37B:
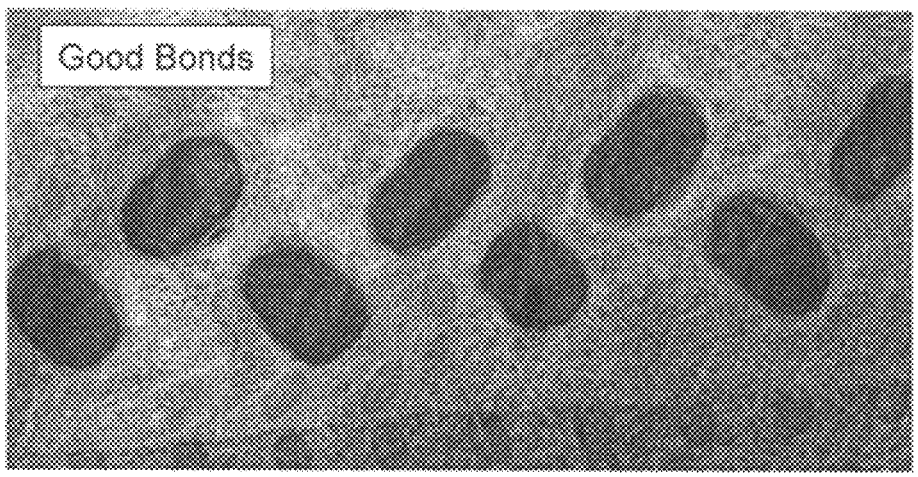
Figure 37C:
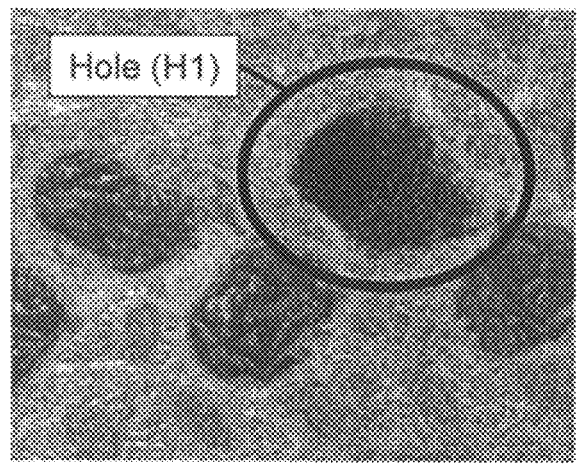
Figure 37D:
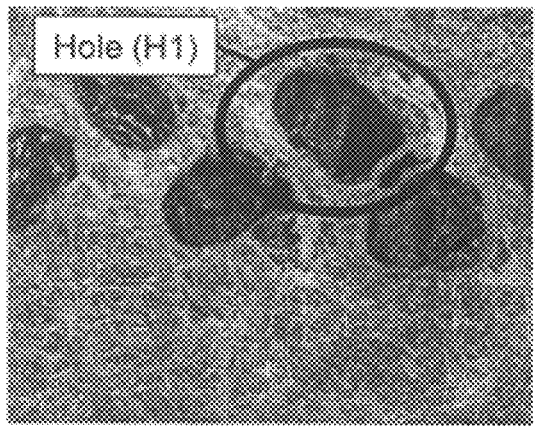
Figure 37E:
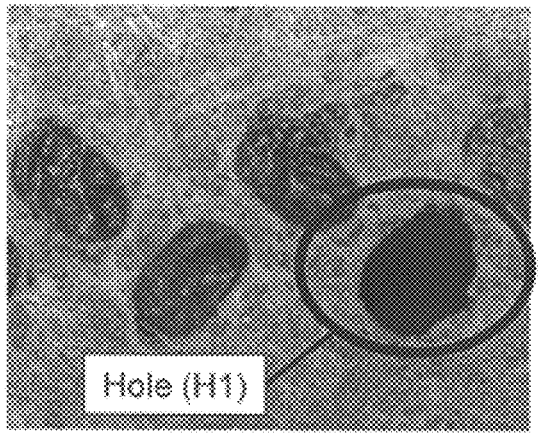
Figure 37F:
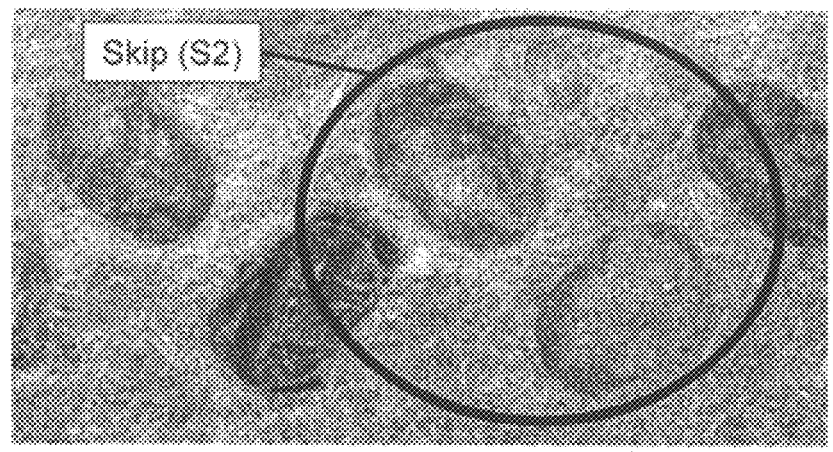
Figure 37G:
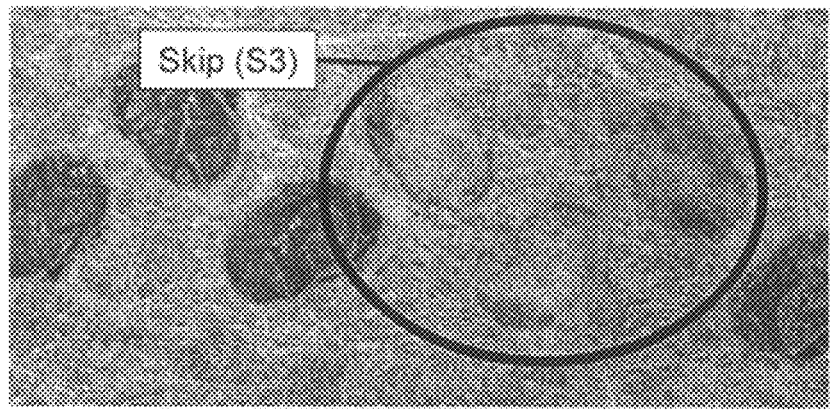

FIG. 36 is graphical illustration of the bond defects of samples BLC1-BLC6 of Table 4 as a function of basis weight COV. The line BLC6 represents the average number of defects observed over the range of basis weight COV values observed in current 15 gsm barrier leg cuffs. Previous manufacturer trials have shown that the basis weight uniformity may be increased through increasing the amount of the meltblown basis weight. The results suggests that if 13 gsm barrier leg cuff could achieve a basis weight COV value of 0.03, it would be theoretically possible to attain the current levels of bond defects and bond strength observed in the 15 gsm barrier leg cuff Example 5

A multicomponent, silicone, non-aqueous and solventless HSC composition is prepared by mixing a vinyl terminated polydimethyl siloxane, methylhydrogen polydimethyl siloxane and cross-linker and catalyst. The mixture is mixed in a ratio of 92% SylOFF 9110 brand silicone polymer, 5% SylOFF 7682 brand cross-linker and 3% SylOFF 4000 brand catalyst. 400 µg/g of the HSC is deposited on the substrate. Suitable substrates for use in this example include the lightweight nonwoven laminates having a spunbond/meltblown/ spunbond laydown in gsm of 6/1/6, 7/1/7, and 8/1/8. The HSC also contains a transition metal catalyst to facilitate the self-cross-linking of the PDMS polymers. The coated substrate is thermally cured at a temperature range of from 80° C. to 120° C. for 0.5-1.0 minute and then stored in a suitable container for later use. After the thermal curing process, the cross-linker is substantially removed from the HSC.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited herein, including any cross referenced or related patent or application, is hereby incorporated by reference in its entirety unless expressly excluded or otherwise limited. The citation of any document is an admission that it is prior art with respect to any invention disclosed or claimed herein or that it alone, or in any combination with any other reference or references, teaches, suggests, or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article to be worn about the lower torso, the absorbent article comprising a chassis comprising a topsheet, a backsheet, and an absorbent core disposed between the topsheet and the backsheet; and
a pair of longitudinal barrier cuffs attached to the chassis, each longitudinal cuff formed of a web of material, the web of material having first and second opposing surfaces, the web of material comprising a nonwoven component layer comprising fibers having a number-average diameter of less than about 1 micron, a mass-average diameter of less than about 1.5 microns, and a ratio of the mass-average diameter to the number-average diameter less than about 2; and
a hydrophobic coating disposed on at least one surface of the web of material such that a coated web of material is formed, the hydrophobic surface coating comprising a solventless, non-aqueous, multicomponent silicone composition including at least two silicone polymers and being substantially free of aminosilicones.

2. The article of claim 1, wherein the web of material has a low surface tension fluid strikethrough time of at least about 19 seconds.

3. The article of claim 1, wherein the air permeability of the web of material is at least about 20 m³/m²/min.

4. The article of claim 1, wherein the web of material has a low surface tension fluid strikethrough time of at least about 23 seconds and an air permeability of at least about 40 m³/m²/min.

5. The article of claim 1, wherein the web of material comprises a nonwoven material.

6. The article of claim 1, wherein the web of material comprises polyolefins.

7. The article of claim 1, wherein the web of material surface having the hydrophobic surface coating thereon is a skin-contacting surface of the web of material.

8. The article of claim 1, wherein at least one of the silicone polymers is cross-linked.

9. The article of claim 8, wherein at least one of the silicone polymers is selected from the group consisting of silicone MQ resins, polydimethylsiloxanes, epoxy silicones, amido silicones, silicone liquid elastomers, and combinations thereof.

10. The article of claim 1, wherein at least one of the silicone polymers is a polydimethylsiloxane selected from the group consisting of vinyl-terminated polydimethylsiloxanes, methyl hydrogen dimethylsiloxanes, organo-modified polydimethylsiloxanes, hydroxyl-terminated polydimethylsiloxanes, and combinations thereof.

11. The article of claim 1, wherein at least one of the silicone polymers has a molecular weight of at least 4000 MW.

12. The article of claim 1, wherein the hydrophobic surface coating is present in an amount of at least 1 microgram per gram of surface.

13. The article of claim 1, wherein the web of material comprises:
two additional nonwoven component layers, each comprising fibers having an average diameter in the range of about 8 microns to about 30 microns;
wherein the nonwoven component layer comprising fibers having a number-average diameter of less than about 1 micron, a mass-average diameter of less than about 1.5 microns, and a ratio of the mass-average diameter to the number-average diameter less than about 2 is disposed intermediate the two additional nonwoven component layers, and wherein each of the three nonwoven component layers are intermittently bonded to each other.

14. The article of claim 13, wherein the three nonwoven component layers together have a total basis weight less than about 15 gsm.

15. The article of claim 1, wherein the web of material comprises:
a first nonwoven component layer comprising fibers having an average diameter in the range of about 8 microns to about 30 microns;
a second nonwoven component layer that is the nonwoven component layer comprising fibers having a number-average diameter of less than about 1 micron, a mass-average diameter of less than about 1.5 microns, and a ratio of the mass-average diameter to the number-average diameter less than about 2;
a third nonwoven component layer comprising fibers having an average diameter in the range of about 8 microns to about 30 microns; and
a fourth nonwoven component layer comprising fibers having an average diameter in the range of about 1 micron to about 8 microns;
wherein the second and fourth nonwoven component layers are both disposed intermediate the first nonwoven component layer and the third component nonwoven layer, and wherein the first, second, third, and fourth nonwoven component layers are intermittently bonded to each other.

16. The article of claim 15, wherein the first, second, third, and fourth nonwoven component layers together have a total basis weight less than about 15 gsm.

17. The article of claim 15, wherein the chassis defines a first end and a second end, wherein a central longitudinal axis is defined in the chassis and extends from the first end to the second end, wherein the third nonwoven component layer is positioned most proximal to the central longitudinal axis, wherein the first nonwoven component layer is positioned most distal from the central longitudinal axis, and wherein the second nonwoven component layer is disposed intermediate the third nonwoven component layer and the fourth nonwoven component layer; and
wherein the hydrophobic surface coating is disposed on the first nonwoven component layer.

18. An absorbent article comprising:
a. a liquid pervious first topsheet;
b. a backsheet joined to at least a portion of the topsheet;
c. an absorbent core disposed between the topsheet and the backsheet;
d. at least one barrier member comprising a web of material, the web of material having first and second opposing surfaces and having:
a low surface tension fluid strikethrough time of at least about 19 seconds; and an air permeability of at least about 20 $m^3/m^2$/min; and
e. a hydrophobic coating disposed on at least one surface of the web of material such that a coated web of material is formed, the hydrophobic surface coating comprising a solventless, non-aqueous, multicomponent silicone composition including at least two silicone polymers and being substantially free of aminosilicones.

19. The article of claim 18, wherein the basis weight of the web of material is in the range of about 7 gsm to about 15 gsm.

20. The article of claim 18, wherein the barrier member is selected from the group consisting of a core cover, an outer cover, a gasketing cuff, a barrier cuff, an elasticized topsheet, and combinations thereof.

* * * * *